US006994854B1

(12) United States Patent
Betsou et al.

(10) Patent No.: US 6,994,854 B1
(45) Date of Patent: Feb. 7, 2006

(54) PROTECTIVE EPITOPES OF ADENYL CYCLASE-HAEMOLYSIN (AC-HLY), THEIR APPLICATION TO THE TREATMENT OR TO THE PREVENTION OF BORDETELLA INFECTIONS

(75) Inventors: Fotini Betsou, Amiens (FR); Peter Sebo, Prague (CZ); Nicole Gutso, Paris (FR)

(73) Assignee: Institut Pasteur, Paris (FR)

( * ) Notice: Subject to any disclaimer, the term of this patent is extended or adjusted under 35 U.S.C. 154(b) by 403 days.

(21) Appl. No.: 09/907,951

(22) Filed: Jul. 19, 2001

Related U.S. Application Data

(62) Division of application No. 08/669,785, filed on Jun. 27, 1996, now Pat. No. 6,309,648.

(30) Foreign Application Priority Data

Jun. 30, 1995 (FR) .................................. 95 07945

(51) Int. Cl.
A61K 39/40 (2006.01)
(52) U.S. Cl. .............................. 424/150.1; 424/139.1; 424/140.1; 424/141.1; 424/163.1; 424/164.1; 530/387.1; 530/388.1; 530/388.4
(58) Field of Classification Search ............. 424/139.1, 424/140.1, 141.1, 150.1, 163.1, 164.1; 530/387.1, 530/388.1, 388.4
See application file for complete search history.

(56) References Cited

U.S. PATENT DOCUMENTS

| 5,095,094 | A |   | 3/1992 | Brezin et al. |         |
|-----------|---|---|--------|---------------|---------|
| 5,183,745 | A | * | 2/1993 | Danchin et al.| 435/232 |
| 5,595,901 | A |   | 1/1997 | Rocancourt et al. |     |

FOREIGN PATENT DOCUMENTS

| EP | 0162639     | 11/1985 |
| EP | 0 235 474   | 9/1987  |
| EP | 0 275 689   | 7/1988  |
| EP | 0338 170    | 10/1989 |
| FR | 2 606 789   | 5/1988  |
| WO | WO 90/13312 | 11/1990 |

OTHER PUBLICATIONS

Greenspan et al. (Nature Biotechnology 17: 936-937, 1999).*
Campbell (Monoclonal Antibody Technology, Elsevier, N.Y. 1984; chapter 1, pp. 1-32).*
Glaser et al (EMBO Journal, 1988, vol. 7, pp. 3997-4004).*
Munier et al. (European Journal and Biochemistry, 1991, vol. 196, pp. 469-474).*
Beattie et al., Repressor Binding to a Regulator Site in the DNA Coding Sequence is Sufficient to Confer Transcriptional Regulation of the virr-Repressed Genes (vrg Genes) in *Bordetella pertussis, Journal of Bacteriology*, vol. 175, No. 2, pp. 519-527 (Jan. 1993).
Betsou, "Cyac-Mediated Activation is Important Not Only for Toxic but for Protective Activities of *Bordetella pertussis* Adenylate Cyclase-Hemolysin", *Infection and Imminity*, vol. 61, No. 9, pp. 3583-3589 (sep. 1993).
Gross et al., "Targeted Mutation that Ablate Either the Adenylate Cylase or Hemolysin Function of the Bifunctional cyaA toxin of *Bordetella pertussis* Abolish Virulence", *Proc. Nat'l Acad. Sci.*, vol. 89, pp. 4898-4902 (Jun. 1992).
Hackett et al., "Internal Lysine Palmitoylation in Adenylate Cyclase Toxin from *Bordetella pertussis*", *Science*, vol. pp. 433-435 (Oct. 1994).
Bartoloni et al., *Tokai J. Exp. Clin. Med.*, 13 (Suppl.), pp. 217-222 (1988).
Beattie et al., "A vir-Repressed Gene of *Bordetella pertussis* is Required for Virulence," *Infect. & Immun.*, vol. 60, No. 2, pp. 571-577 (1992).
Beattie et al., *J. Bacteriol.*, vol. 172, No. 12, pp. 6997-7004 (1990).
de Rossi et al., *Vet. Microbiol*, vol. 56, pp. 65-77 (1997).
Goldman et al., *EMBO Journal*, vol. 3, No. 6 1353-1356 (1984).
Grimprel et al. *Clin. & Diagn. Lab. Immunol.*, vol. 3, No. 1, pp. 93-97 (1996).
Gueirard et al., *Scand. J. Immunol.*, No. 43, pp. 181-192 (1996).
Gueirard et al., *J. Clin. Microbiol.*, vol. 33, No. 8, pp. 2002-2006 (1995).
Gierard et al., IN: Bacterial Protein Toxins ed. Freer et al., pp. 152-153 (1994).
Gueirard et al., "Virulence of Bordetella bronchiseptica: Role of Adenylate Cyclase-Hemolysin," *Infect. & Immun.*, vol. 61, No. 10, pp. 4072-4078 (1993).
Guiso et al., *Microbiol. Pathogenesis*, vol. 11, pp. 423-431 (1991).
Hausman et al., *Inf. & Imm.*, vol. 64, No. 10, pp. 4020-4026 (1996).
Horiguchi et al., *Inf. & Imm.*, vol. 59, No. 3, pp. 1112-1116 (1991).
Khelef et al., *Inf. & Imm.*, vol. 62, No. 7, pp. 2893-2900 (1994).
Khelef et al., IN: Bacterial Protein Toxins ed. Freer et al., pp. 514-515 (1994).

(Continued)

*Primary Examiner*—Lynette R. F. Smith
*Assistant Examiner*—Robert A. Zeman
(74) *Attorney, Agent, or Firm*—Finnegan, Henderson, Farabow, Garrett & Dunner LLP

(57) ABSTRACT

The subject of the invention is amino acid sequences of the AC-Hly from *B. pertussis, B. parapertussis* and/or *B. bronchiseptica*, carrying epitopes capable of inducing a protective immune response against infection by *Bordetella*. The subject of the invention is antibodies, especially monoclonal antibodies, directed against these epitopes.

3 Claims, 22 Drawing Sheets

OTHER PUBLICATIONS

Figure 1:
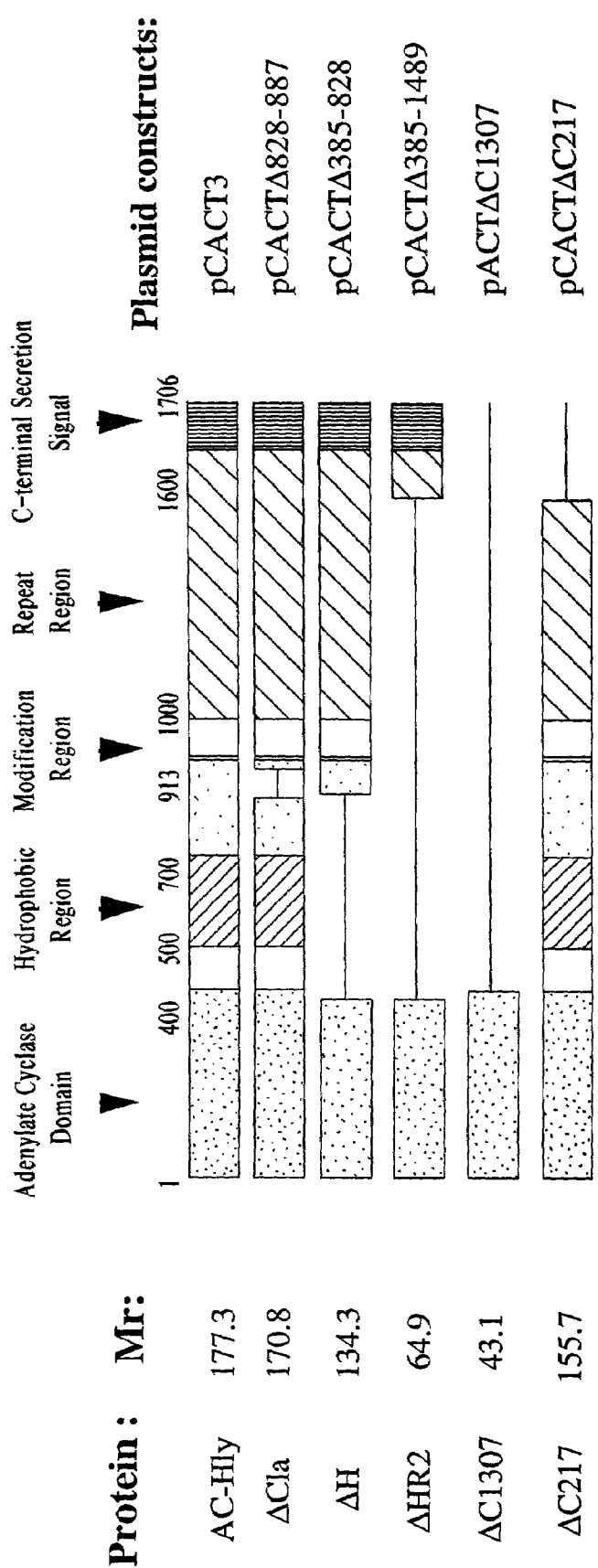

Khelef et al., *Microbiol. Pathogenesis*, vol. 12, pp. 227-235 (1992).
Khelef et al., *Infection & Immunity*, vol. 61, No. 2, pp. 486-490 (1993).
Knapp et al., "Two trans-Acting Regulatory Genes (vir and mod) Control Antigenic Modulatio in *Bordetella pertuss*," *J. Bacteriol.*, vol. 170, No. 11, pp. 5059-5066 (1988).
LeBlay et al., *Microbiology*, vol. 143, pp. 1433-1441 (1997).
Munoz et al., *Infection & Immunity*, vol. 32, No. 1, pp. 243-250 (1981).
Nakase et al., "Bestandteile von Bordetella Pertussis. Besonders Über Die Schutzsubstanz," *Chem. Zentralblatt NR*, 8-1284, p. 2576 (1966).
Pittman, *Rev. Infectious Disease*, vol. No. 3, pp. 401-412 (1979).
Glaser et al., *Molecular Microbiology*, vol. 2, No. 1, pp. 19-30 (1988).
Novotny et al., "Adenylate Cyclase Activity of a 68,000-Molecular-Weight Protein Isolated from the Outer Membrane of Bordetella bronchiseptica", *Infection & Immunity*, vol. 50, No. 1, pp. 199-206 (Oct. 1985).
Brennan et al., "Identification of a 69-Kilodalton Nonfimoral protein As an Aggulutinogen of *Bordetella pertussis*", *Infection & Immunity*, vol. 56, No. 12, pp. 3189-3195 (Dec. 1988).
Charles et al., "Molecular cloning and characterization of protective outer membrane protein P.69 from *Bordetella pertussis*", *Proc. Nat'l Acad. Sci. USA*, vol. 86, pp. 3554-3558 (May 1989).
Novotny et al., "Biologic and Protective Properties of the 69-kDa Outer Membrane Protein of *Bordetella pertussis*: A Novel Formulation for an Acellular Pertussis Vaccine", *J. Infectious Diseases*, pp. 114-122 (1991).
S. Karger, Basel, "Bordetella Adenylate Cyclase: A Genus Specific Protective Antigen and Virulence Factor", Proceedings of the Fourth International Symposium on Pertussis, *Dev. Biol. Standard*, vol. 61, pp. 27-41 (1985).
Kessin et al., "Secreted Adenylate Cyclase of *Bordetella pertussis*: Calmodulin Requirements and Partial Purification of Two Forms", *J. Bacteriology*, pp. 290-296 (Apr. 1986).
Friedman, "*Bordetella pertussis* Adenylate Cyclase: Isolation and Purification by Calmodulin-Sepharose 4B Chromatography", *Infection & Immunity*, pp. 129-134 (Jan. 1987).
Ladant et al., "*Bordetella pertussis* Adenylate Cyclase: Purification, Characterization and radioimmunoassy", *The Journal of Biological Chemistry*, vol. 261, No. 34, pp. 16264-16269 (Dec. 1986).
Hewlett et al., "Adenylate Cyclase Toxin from *Bordetella pertussis* Identification and Purification of Holotoxin Molecule", *The Journal of Biological Chemistry*, vol. 264, No. 32, pp. 19379-19384 (Nov. 1989).
Shattuck et al., "Purification and Characterization of a Calmodulin-Sensitive Adenylate Cycle from *Bordetella pertissis*", *Biochemistry*, vol. 24, pp. 6356-6362 (1985).
Hackett et al., "Hemolytic, but Not Cell-Invasive Activity, of Adenylate Cyclase Toxin Is Selectively Affected by Differential Fatty-acylation in *Escherichia coil*", *The Journal of Biological Chemistry*, vol. 270, No. 35, pp. 20250-20253 (Sep. 1995).
Iwaki et al., "Identification by in vitro complementation of regions required for cell-invasive activity of Bordetella pertussis adenylate cyclase toxin", *Molecular Microbiology*, vol. 17, No. 6, pp. 1015-1024 (1995).
Immunization Practices Advisory Committee, Clinical Pharmacy, col. 8, pp. 839-851 (1989).

Munier et al., *Eur. J. Biochem.*, vol. 196, No. 2, pp. 469-474 (1991).
Gross et al., *Proc. Nat'l. Acad. Sci. USA*, vol. 89, No. 11, pp. 4898-4902 (1992).
Sakamoto et al., *J. Biological Chemistry*, vol. 267, No. 19, pp. 13598-13602 (1992).
Heveker et al., *J. Biological Chemistry*, vol. 269, No. 52, pp. 32844-32847 (1994).
Guiso et al., Proc. of the 6th Int'l. Symposium on Pertussis, pp. 207-211 (1990).
Guiso et al., Zentralblatt fur Bakteriologie, Supp. 23, pp. 268-271 (1992).
Ladant et al., *J. Biological Chemistry*, vol. 264, No. 7, pp. 4015-4020 (1989).
Ladant et al., *J. Biological Chemistry*, vol. 267, No. 4, pp. 2244-2250 (1992).
Ballalou et al., *Infection & Immunity*, vol. 58, No. 10, pp. 3242-3247 (1990).
Peter Sobo et al., "Repeat Sequence in the *Bordetella pertussis* Adenylate Cyclase Toxin Can Be Recognized as Alternative Carboxyproximal Secretion Signals by the *Escherichia coli* α-haemolysin translocator", *Molecular Microbiology*, vol. 9, No. 5, pp. 999-1009 (1993).
Betsou et al., "The C-Terminal Domain is Essential for Protective Activity of the *Bordetella pertussis* Adenylate Cyclase-Hemolysin," *Infection and Immunity*, pp. 3309-3315 (1995).
Burnette et al., "Pertussis Toxin S1 Mutant with Reduced Enzyme Activity and a Conserved Protective Epitope," Science, 242:72-74 (1988).
Tippetts et al., "Molecular Cloning and Expression of the Bacillus anthracis Ederna Factor Toxin Gene: a Calmodulin-Dependent Adenylate Cyclase," J. Bacteriol. 170(5): 2263-2266 (1988).
Weiss et al., "Tn5-Induced Mutations Affecting Virulence Factors of *Bordetella pertussis*," Infection and Immunity, 42:33-41 (1983).
Glaser et al., "Identification of Residues Essential for Catalysis and Binding of Calmodulin in *Bordetella pertussis* Adenylate Cyclase by Site-directed Mutagenesis," EMBO J. 8(3):967-972 (1989).
Au et al., "Site-Directed Mutagenesis of Lysine 58 in a Putative ATP-Binding Domain of the Calmodulin-Sensitive Adenylate Cyclase from *Bordetella pertussis* Abolishes Catalytic Activity," Biochemistry, 28:2772-2776 (1989).
N. Guiso, et al., "Bordetella adenylate cyclase in a virulence associated factor and an immunoprotective antigen," Microbial Pathogenesis 1989: 7:373-380.
D. Landant, "Interaction of *Bordetella pertussis* Adenylate Cyclase with Calmodulin," The Journal of Biology Chemistry, vol. 263, No. 6, Issue of Feb. 25, pp. 2612-2618, 1988.
M. M. Holland, "Isolation and Characterization of a Small Catalytic Domain Released from the Adenylate Cyclase from *Eschericha coli* by Digestion with Trypsin," the Journal of Biological Chemistry, vol. 263, Issue of Oct. 15, pp. 14661-14668, 1988.
Abstract. P. Glaser et al., "The calmodulin-sensitive adenylate cyclase of *Bordetella pertussis*: cloning and expression in *Escherichia coli*," Chemical Abstracts, vol. 112,1990.
European Search Report dated feb. 22, 1990, for EP 89 40 2948.

* cited by examiner 1 2 3 4 5 6 7

1 2 3 4 5 6 7

1 2 3 4 5 6 7

1 2 3 4 5 6 7

1 2 3 4 5 6 7

1 2 3 4 5 6 7

Bordetella pertussis *adenylate cyclase*

```
CGATCATTCG GCATGTACGG TCCAGCTGCG CGCGAGCGGC GGCCGCGTCC AGCGCGCGGC      60
CTCGGTACTC CTTGACGCGC GCGGTGTCGC CGCCGCGCCG AACGCGCAGC GAACGGCCCA     120
CGCTGTCGGG GTGCCGTTCG GCCAGCGCGC GGCGCAGCGC ACGATTGTCG TCGCGCGAGA     180
ATGGCGCGAT CCAGTCGATG ATCCACAGTC GGTCGCCGCA GTTCCAGGCA TTCCCGCCCA     240
GCGACGAGGG CGCCATGACA TAGGAGAGTT CGGTGTCGGC GTCCATTAGG GCCCAGCTGC     300
AGTATGCAAC CGGCACGTCA TTGCATCGCA GCAGAATGTA TTGGCCCAGT TGAATCGGCG     360
CGAGCGCTGT TGCGTGCGAG CAGATGCACC GGCCAGTCGC GGTGCATGGG AGAGTTCATC     420
CACAGCCAGG CAATATTGCC CAGTGCCGCG AAGTCGTCGG TGGGATTGAG GAGGGAGGGC     480
GCTTGGGCGG ACGGAAGCAT GACATCGGTG CATGGTGGAG CGGGGGGCAT ATTCCGTGTT     540
GGGTGCGCGC ATGGCAAGCC GCCGGCGCAT CATGGTTGCG CCGGAATGGC TTTTCTTACA     600
TGTTTCCAGG ATATGTCCGT ATTTCGGGCG ATGCCTCGGT CGCGGCGCCT GCTTTTGTCG     660
AACATGTGCA ATGTTGTTGT CGCGATCGCG TTGGCGCTTG CTCGCTTATT TATCTCCCTT     720
GAAGCCTTGT TCTTCTTTTC ATTAGAAAGA AATATGCGCT TTGTGTTTAG GATGATTTTC     780
CTGTCCGAGT AGGGTGGATC CAAATTTTCC GGATTGGTGG GAATTTGTGC ATTTTCACTG     840
CGAATGTTGG AATAATTTCG CCCATCGTCA TACGACATGC TGGATGTTTG GTTCTTGCAG     900
AAGGATGAGG TTCTGAGCGC TACACACCGG TTGCGTCGGT GCGAATCCGT TCAATCGACT     960
```

| | | | | | | | | | |
|---|---|---|---|---|---|---|---|---|---|
| ACTTATCGAC AGATCCAC | ATG | CAG | CAA | TCG | CAT | CAG | GCT | GGT | TAC GCA AAC | 1011 |
| | Met | Gln | Gln | Ser | His | Gln | Ala | Gly | Tyr Ala Asn | |
| | 1 | | | 5 | | | | | 10 | |

```
GCC GCC GAC CGG GAG TCT GGC ATC CCC GCA GCC GTA CTC GAT GGC ATC       1059
Ala Ala Asp Arg Glu Ser Gly Ile Pro Ala Ala Val Leu Asp Gly Ile
            15                  20                  25

AAG GCC GTG GCG AAG GAA AAA AAC GCC ACA TTG ATG TTC CGC CTG GTC       1107
Lys Ala Val Ala Lys Glu Lys Asn Ala Thr Leu Met Phe Arg Leu Val
        30                  35                  40

AAC CCC CAT TCC ACC AGC CTG ATT GCC GAA GGG GTG GCC ACC AAA GGA       1155
Asn Pro His Ser Thr Ser Leu Ile Ala Glu Gly Val Ala Thr Lys Gly
    45                  50                  55

TTG GGC GTG CAC GCC AAG TCG TCC GAT TGG GGG TTG CAG GCG GGC TAC       1203
Leu Gly Val His Ala Lys Ser Ser Asp Trp Gly Leu Gln Ala Gly Tyr
60                  65                  70                  75

ATT CCC GTC AAC CCG AAT CTT TCC AAA CTG TTC GGC CGT GCG CCC GAG       1251
Ile Pro Val Asn Pro Asn Leu Ser Lys Leu Phe Gly Arg Ala Pro Glu
                80                  85                  90

GTG ATC GCG CGG GCC GAC AAC GAC GTC AAC AGC AGC CTG GCG CAT GGC       1299
Val Ile Ala Arg Ala Asp Asn Asp Val Asn Ser Ser Leu Ala His Gly
            95                  100                 105
```

FIG. 5A

```
CAT ACC GCG GTC GAC CTG ACG CTG TCG AAA GAG CGG CTT GAC TAT CTG        1347
His Thr Ala Val Asp Leu Thr Leu Ser Lys Glu Arg Leu Asp Tyr Leu
        110             115                 120

CGG CAA GCG GGC CTG GTC ACC GGC ATG GCC GAT GGC GTG GTC GCG AGC        1395
Arg Gln Ala Gly Leu Val Thr Gly Met Ala Asp Gly Val Val Ala Ser
        125             130                 135

AAC CAC GCA GGC TAC GAG CAG TTC GAG TTT CGC GTG AAG GAA ACC TCG        1443
Asn His Ala Gly Tyr Glu Gln Phe Glu Phe Arg Val Lys Glu Thr Ser
140             145                 150                 155

GAC GGG CGC TAT GCC GTG CAG TAT CGC CGC AAG GGC GGC GAC GAT TTC        1491
Asp Gly Arg Tyr Ala Val Gln Tyr Arg Arg Lys Gly Gly Asp Asp Phe
                160                 165                 170

GAG GCG GTC AAG GTG ATC GGC AAT GCC GCC GGT ATT CCA CTG ACG GCG        1539
Glu Ala Val Lys Val Ile Gly Asn Ala Ala Gly Ile Pro Leu Thr Ala
            175                 180                 185

GAT ATC GAC ATG TTC GCC ATT ATG CCG CAT CTG TCC AAC TTC CGC GAC        1587
Asp Ile Asp Met Phe Ala Ile Met Pro His Leu Ser Asn Phe Arg Asp
        190                 195                 200

TCG GCG CGC AGT TCG GTG ACC AGC GGC GAT TCG GTG ACC GAT TAC CTG        1635
Ser Ala Arg Ser Ser Val Thr Ser Gly Asp Ser Val Thr Asp Tyr Leu
205                 210                 215

GCG CGC ACG CGG CGG GCC GCC AGC GAG GCC ACG GGC GGC CTG GAT CGC        1683
Ala Arg Thr Arg Arg Ala Ala Ser Glu Ala Thr Gly Gly Leu Asp Arg
220                 225                 230                 235

GAA CGC ATC GAC TTG TTG TGG AAA ATC GCT CGC GCC GGC GCC CGT TCC        1731
Glu Arg Ile Asp Leu Leu Trp Lys Ile Ala Arg Ala Gly Ala Arg Ser
                240                 245                 250

GCA GTG GGC ACC GAG GCG CGT CGC CAG TTC CGC TAC GAC GGC GAC ATG        1779
Ala Val Gly Thr Glu Ala Arg Arg Gln Phe Arg Tyr Asp Gly Asp Met
            255                 260                 265

AAT ATC GGC GTG ATC ACC GAT TTC GAG CTG GAA GTG CGC AAT GCG CTG        1827
Asn Ile Gly Val Ile Thr Asp Phe Glu Leu Glu Val Arg Asn Ala Leu
        270                 275                 280

AAC AGG CGG GCG CAC GCC GTC GGC GCG CAG GAC GTG GTC CAG CAT GGC        1875
Asn Arg Arg Ala His Ala Val Gly Ala Gln Asp Val Val Gln His Gly
        285                 290                 295

ACT GAG CAG AAC AAT CCT TTC CCG GAG GCA GAT GAG AAG ATT TTC GTC        1923
Thr Glu Gln Asn Asn Pro Phe Pro Glu Ala Asp Glu Lys Ile Phe Val
300                 305                 310                 315

GTA TCG GCC ACC GGT GAA AGC CAG ATG CTC ACG CGC GGG CAA CTG AAG        1971
Val Ser Ala Thr Gly Glu Ser Gln Met Leu Thr Arg Gly Gln Leu Lys
                320                 325                 330

GAA TAC ATT GGC CAG CAG CGC GGC GAG GGC TAT GTC TTC TAC GAG AAC        2019
Glu Tyr Ile Gly Gln Gln Arg Gly Glu Gly Tyr Val Phe Tyr Glu Asn
            335                 340                 345

CGT GCA TAC GGC GTG GCG GGG AAA AGC CTG TTC GAC GAT GGG CTG GGA        2067
Arg Ala Tyr Gly Val Ala Gly Lys Ser Leu Phe Asp Asp Gly Leu Gly
        350                 355                 360
```

FIG. 5B

```
GCC GCG CCC GGC GTG CCG AGC GGA CGT TCG AAG TTC TCG CCG GAT GTA     2115
Ala Ala Pro Gly Val Pro Ser Gly Arg Ser Lys Phe Ser Pro Asp Val
    365                 370                 375

CTG GAA ACG GTG CCG GCG TCA CCC GGA TTG CGG CGG CCG TCG CTG GGC     2163
Leu Glu Thr Val Pro Ala Ser Pro Gly Leu Arg Arg Pro Ser Leu Gly
380                 385                 390                 395

GCA GTG GAA CGC CAG GAT TCC GGC TAT GAC AGC CTT GAT GGG GTG GGA     2211
Ala Val Glu Arg Gln Asp Ser Gly Tyr Asp Ser Leu Asp Gly Val Gly
                400                 405                 410

TCG CGA TCG TTC TCG TTG GGC GAG GTG TCC GAC ATG GCC GCC GTG GAA     2259
Ser Arg Ser Phe Ser Leu Gly Glu Val Ser Asp Met Ala Ala Val Glu
            415                 420                 425

GCG GCG GAA CTG GAA ATG ACC CGG CAA GTC TTG CAC GCC GGG GCG CGG     2307
Ala Ala Glu Leu Glu Met Thr Arg Gln Val Leu His Ala Gly Ala Arg
        430                 435                 440

CAG GAC GAT GCC GAG CCG GGC GTG AGC GGT GCG TCG GCG CAC TGG GGG     2355
Gln Asp Asp Ala Glu Pro Gly Val Ser Gly Ala Ser Ala His Trp Gly
    445                 450                 455

CAG CGG GCG CTG CAG GGC GCC CAG GCG GTG GCG GCG GCG CAG CGG CTG     2403
Gln Arg Ala Leu Gln Gly Ala Gln Ala Val Ala Ala Ala Gln Arg Leu
460                 465                 470                 475

GTT CAT GCC ATT GCC CTG ATG ACG CAA TTC GGC CGG GCC GGT TCC ACC     2451
Val His Ala Ile Ala Leu Met Thr Gln Phe Gly Arg Ala Gly Ser Thr
                480                 485                 490

AAC ACG CCG CAG GAA GCG GCC TCG TTG TCG GCG GCC GTG TTC GGC TTG     2499
Asn Thr Pro Gln Glu Ala Ala Ser Leu Ser Ala Ala Val Phe Gly Leu
            495                 500                 505

GGC GAG GCC AGC AGC GCC GTG GCC GAA ACC GTG AGC GGT TTT TTC CGC     2547
Gly Glu Ala Ser Ser Ala Val Ala Glu Thr Val Ser Gly Phe Phe Arg
        510                 515                 520

GGG TCT TCG CGC TGG GCC GGC GGT TTC GGC GTG GCT GGC GGC GCG ATG     2595
Gly Ser Ser Arg Trp Ala Gly Gly Phe Gly Val Ala Gly Gly Ala Met
    525                 530                 535

GCG CTG GGA GGC GGC ATC GCC GCG GCC GTT GGC GCC GGG ATG TCG TTG     2643
Ala Leu Gly Gly Gly Ile Ala Ala Ala Val Gly Ala Gly Met Ser Leu
540                 545                 550                 555

ACC GAT GAC GCG CCG GCC GGA CAG AAG GCC GCC GCC GGC GCC GAG ATC     2691
Thr Asp Asp Ala Pro Ala Gly Gln Lys Ala Ala Ala Gly Ala Glu Ile
                560                 565                 570

GCG CTG CAG TTG ACA GGT GGA ACG GTC GAG CTG GCT TCT TCC ATC GCG     2739
Ala Leu Gln Leu Thr Gly Gly Thr Val Glu Leu Ala Ser Ser Ile Ala
            575                 580                 585

TTG GCG CTG GCC GCG GCG CGC GGC GTG ACC AGC GGC TTG CAG GTG GCC     2787
Leu Ala Leu Ala Ala Ala Arg Gly Val Thr Ser Gly Leu Gln Val Ala
        590                 595                 600

GGG GCG TCG GCC GGG GCG GCT GCC GGC GCA TTG GCC GCG GCG CTC AGT     2835
Gly Ala Ser Ala Gly Ala Ala Ala Gly Ala Leu Ala Ala Ala Leu Ser
    605                 610                 615
```

FIG. 5C

```
CCC ATG GAG ATC TAC GGC CTG GTG CAG CAA TCG CAC TAT GCG GAT CAG    2883
Pro Met Glu Ile Tyr Gly Leu Val Gln Gln Ser His Tyr Ala Asp Gln
620             625                 630                 635

CTG GAC AAG CTG GCG CAG GAA TCG AGC GCA TAC GGT TAC GAG GGC GAC    2931
Leu Asp Lys Leu Ala Gln Glu Ser Ser Ala Tyr Gly Tyr Glu Gly Asp
                640                 645                 650

GCC TTG CTG GCC CAG CTG TAT CGC GAC AAG ACG GCC GCC GAG GGC GCC    2979
Ala Leu Leu Ala Gln Leu Tyr Arg Asp Lys Thr Ala Ala Glu Gly Ala
            655                 660                 665

GTC GCC GGC GTC TCC GCC GTC CTG AGC ACG GTG GGG GCG GCG GTG TCG    3027
Val Ala Gly Val Ser Ala Val Leu Ser Thr Val Gly Ala Ala Val Ser
        670                 675                 680

ATC GCC GCG GCG GCC AGC GTG GTA GGG GCC CCG GTG GCG GTG GTC ACT    3075
Ile Ala Ala Ala Ala Ser Val Val Gly Ala Pro Val Ala Val Val Thr
    685                 690                 695

TCC TTG CTG ACC GGG GCT CTC AAC GGC ATC CTG CGC GGC GTG CAG CAG    3123
Ser Leu Leu Thr Gly Ala Leu Asn Gly Ile Leu Arg Gly Val Gln Gln
700             705                 710                 715

CCC ATC ATC GAA AAG CTG GCC AAC GAT TAC GCT CGC AAG ATC GAC GAG    3171
Pro Ile Ile Glu Lys Leu Ala Asn Asp Tyr Ala Arg Lys Ile Asp Glu
                720                 725                 730

CTG GGC GGG CCG CAA GCG TAC TTC GAG AAA AAC CTG CAG GCG CGT CAC    3219
Leu Gly Gly Pro Gln Ala Tyr Phe Glu Lys Asn Leu Gln Ala Arg His
            735                 740                 745

GAA CAA CTG GCC AAT TCG GAC GGC CTA CGG AAA ATG CTG GCC GAC CTG    3267
Glu Gln Leu Ala Asn Ser Asp Gly Leu Arg Lys Met Leu Ala Asp Leu
        750                 755                 760

CAG GCC GGT TGG AAC GCC AGC AGC GTG ATC GGG GTG CAG ACG ACA GAG    3315
Gln Ala Gly Trp Asn Ala Ser Ser Val Ile Gly Val Gln Thr Thr Glu
    765                 770                 775

ATC TCC AAG TCG GCG CTC GAA CTG GCC GCC ATT ACC GGC AAC GCG GAC    3363
Ile Ser Lys Ser Ala Leu Glu Leu Ala Ala Ile Thr Gly Asn Ala Asp
780             785                 790                 795

AAC CTG AAA TCC GTC GAC GTG TTC GTG GAC CGC TTC GTC CAG GGC GAG    3411
Asn Leu Lys Ser Val Asp Val Phe Val Asp Arg Phe Val Gln Gly Glu
                800                 805                 810

CGG GTG GCC GGC CAG CCG GTG GTC CTC GAC GTC GCC GCC GGC GGC ATC    3459
Arg Val Ala Gly Gln Pro Val Val Leu Asp Val Ala Ala Gly Gly Ile
            815                 820                 825

GAT ATC GCC AGC CGC AAG GGC GAG CGG CCG GCG CTG ACG TTC ATC ACG    3507
Asp Ile Ala Ser Arg Lys Gly Glu Arg Pro Ala Leu Thr Phe Ile Thr
        830                 835                 840

CCG CTG GCC GCG CCA GGA GAA GAG CAG CGC CGG CGC ACG AAA ACG GGC    3555
Pro Leu Ala Ala Pro Gly Glu Glu Gln Arg Arg Arg Thr Lys Thr Gly
    845                 850                 855

AAG AGC GAA TTC ACC ACA TTC GTC GAG ATC GTG GGC AAG CAG GAC CGC    3603
Lys Ser Glu Phe Thr Thr Phe Val Glu Ile Val Gly Lys Gln Asp Arg
860             865                 870                 875
```

FIG. 5D

```
TGG CGC ATC CGG GAC GGC GCG GCC GAC ACC ACC ATC GAT CTG GCC AAG          3651
Trp Arg Ile Arg Asp Gly Ala Ala Asp Thr Thr Ile Asp Leu Ala Lys
                    880             885                 890

GTG GTG TCG CAA CTG GTC GAC GCC AAT GGC GTG CTC AAG CAC AGC ATC          3699
Val Val Ser Gln Leu Val Asp Ala Asn Gly Val Leu Lys His Ser Ile
            895                 900             905

AAA CTG GAT GTG ATC GGC GGA GAT GGC GAT GAC GTC GTG CTT GCC AAT          3747
Lys Leu Asp Val Ile Gly Gly Asp Gly Asp Asp Val Val Leu Ala Asn
                910             915                 920

GCT TCG CGC ATC CAT TAT GAC GGC GGC GCG GGC ACC AAC ACG GTC AGC          3795
Ala Ser Arg Ile His Tyr Asp Gly Gly Ala Gly Thr Asn Thr Val Ser
        925             930             935

TAT GCC GCC CTG GGT CGA CAG GAT TCC ATT ACC GTG TCC GCC GAC GGG          3843
Tyr Ala Ala Leu Gly Arg Gln Asp Ser Ile Thr Val Ser Ala Asp Gly
940             945                 950                 955

GAA CGT TTC AAC GTG CGC AAG CAG TTG AAC AAC GCC AAC GTG TAT CGC          3891
Glu Arg Phe Asn Val Arg Lys Gln Leu Asn Asn Ala Asn Val Tyr Arg
                960             965                 970

GAA GGC GTG GCT ACC CAG ACA ACC GCC TAC GGC AAG CGC ACG GAG AAT          3939
Glu Gly Val Ala Thr Gln Thr Thr Ala Tyr Gly Lys Arg Thr Glu Asn
            975             980             985

GTC CAA TAC CGC CAT GTC GAG CTG GCC CGT GTC GGG CAA GTG GTG GAG          3987
Val Gln Tyr Arg His Val Glu Leu Ala Arg Val Gly Gln Val Val Glu
        990             995             1000

GTC GAC ACG CTC GAG CAT GTG CAG CAC ATC ATC GGC GGG GCC GGC AAC          4035
Val Asp Thr Leu Glu His Val Gln His Ile Ile Gly Gly Ala Gly Asn
        1005            1010            1015

GAT TCG ATC ACC GGC AAT GCG CAC GAC AAC TTC CTA GCC GGC GGG TCG          4083
Asp Ser Ile Thr Gly Asn Ala His Asp Asn Phe Leu Ala Gly Gly Ser
1020            1025            1030            1035

GGC GAC GAC AGG CTG GAT GGC GGC GCC GGC AAC GAC ACC CTG GTT GGC          4131
Gly Asp Asp Arg Leu Asp Gly Gly Ala Gly Asn Asp Thr Leu Val Gly
            1040            1045            1050

GGC GAG GGC CAA AAC ACG GTC ATC GGC GGC GCC GGC GAC GAC GTA TTC          4179
Gly Glu Gly Gln Asn Thr Val Ile Gly Gly Ala Gly Asp Asp Val Phe
            1055            1060            1065

CTG CAG GAC CTG GGG GTA TGG AGC AAC CAG CTC GAT GGC GGC GCG GGC          4227
Leu Gln Asp Leu Gly Val Trp Ser Asn Gln Leu Asp Gly Gly Ala Gly
        1070            1075            1080

GTC GAT ACC GTG AAG TAC AAC GTG CAC CAG CCT TCC GAG GAG CGC CTC          4275
Val Asp Thr Val Lys Tyr Asn Val His Gln Pro Ser Glu Glu Arg Leu
        1085            1090            1095

GAA CGC ATG GGC GAC ACG GGC ATC CAT GCC GAT CTT CAA AAG GGC ACG          4323
Glu Arg Met Gly Asp Thr Gly Ile His Ala Asp Leu Gln Lys Gly Thr
1100            1105            1110            1115

GTC GAG AAG TGG CCG GCC CTG AAC CTG TTC AGC GTC GAC CAT GTC AAG          4371
Val Glu Lys Trp Pro Ala Leu Asn Leu Phe Ser Val Asp His Val Lys
                1120            1125            1130
```

FIG. 5E

```
AAT ATC GAG AAT CTG CAC GGC TCC CGC CTA AAC GAC CGC ATC GCC GGC                 4419
Asn Ile Glu Asn Leu His Gly Ser Arg Leu Asn Asp Arg Ile Ala Gly
            1135                1140                1145

GAC GAC CAG GAC AAC GAG CTC TGG GGC CAC GAT GGC AAC GAC ACG ATA                 4467
Asp Asp Gln Asp Asn Glu Leu Trp Gly His Asp Gly Asn Asp Thr Ile
        1150                1155                1160

CGC GGC CGG GGC GGC GAC GAC ATC CTG CGC GGC GGC CTG GGC CTG GAC                 4515
Arg Gly Arg Gly Gly Asp Asp Ile Leu Arg Gly Gly Leu Gly Leu Asp
        1165                1170                1175

ACG CTG TAT GGC GAG GAC GGC AAC GAC ATC TTC CTG CAG GAC GAC GAG                 4563
Thr Leu Tyr Gly Glu Asp Gly Asn Asp Ile Phe Leu Gln Asp Asp Glu
1180                1185                1190                1195

ACC GTC AGC GAT GAC ATC GAC GGC GGC GCG GGC CTG GAC ACC GTC GAC                 4611
Thr Val Ser Asp Asp Ile Asp Gly Gly Ala Gly Leu Asp Thr Val Asp
                1200                1205                1210

TAC TCC GCC ATG ATC CAT GCA GGC AAG ATC GTT GCG CCG CAT GAA TAC                 4659
Tyr Ser Ala Met Ile His Ala Gly Lys Ile Val Ala Pro His Glu Tyr
            1215                1220                1225

GGC TTC GGG ATC GAG GCG GAC CTG TCC AGG GAA TGG GTG CGC AAG GCG                 4707
Gly Phe Gly Ile Glu Ala Asp Leu Ser Arg Glu Trp Val Arg Lys Ala
        1230                1235                1240

TCC GCG CTG GGC GTG GAC TAT TAC GAT AAT GTC CGC AAT GTC GAA AAC                 4755
Ser Ala Leu Gly Val Asp Tyr Tyr Asp Asn Val Arg Asn Val Glu Asn
        1245                1250                1255

GTC ATC GGT ACG AGC ATG AAG GAT GTG CTC ATC GGC GAC GCG CAA GCC                 4803
Val Ile Gly Thr Ser Met Lys Asp Val Leu Ile Gly Asp Ala Gln Ala
1260                1265                1270                1275

AAT ACC CTG ATG GGC CAG GGC GGC GAC GAT ACC GTG CGC GGC GGC GAC                 4851
Asn Thr Leu Met Gly Gln Gly Gly Asp Asp Thr Val Arg Gly Gly Asp
                1280                1285                1290

GGC GAT GAT CTG CTG TTC GGC GGC GAC GGC AAC GAC ATG CTG TAT GGC                 4899
Gly Asp Asp Leu Leu Phe Gly Gly Asp Gly Asn Asp Met Leu Tyr Gly
            1295                1300                1305

GAC GCC GGC AAC GAC ACC CTC TAC GGG GGG CTG GGC GAC GAT ACC CTT                 4947
Asp Ala Gly Asn Asp Thr Leu Tyr Gly Gly Leu Gly Asp Asp Thr Leu
        1310                1315                1320

GAA GGC GGC GCG GGC AAC GAT TGG TTC GGC CAG ACG CAG GCG CGC GAG                 4995
Glu Gly Gly Ala Gly Asn Asp Trp Phe Gly Gln Thr Gln Ala Arg Glu
        1325                1330                1335

CAT GAC GTG CTG CGC GGC GGA GAT GGG GTG GAT ACC GTC GAT TAC AGC                 5043
His Asp Val Leu Arg Gly Gly Asp Gly Val Asp Thr Val Asp Tyr Ser
1340                1345                1350                1355

CAG ACC GGC GCG CAT GCC GGC ATT GCC GCG GGT CGC ATC GGG CTG GGC                 5091
Gln Thr Gly Ala His Ala Gly Ile Ala Ala Gly Arg Ile Gly Leu Gly
                1360                1365                1370

ATC CTG GCT GAC CTG GGC GCC GGC CGC GTC GAC AAG CTG GGC GAG GCC                 5139
Ile Leu Ala Asp Leu Gly Ala Gly Arg Val Asp Lys Leu Gly Glu Ala
            1375                1380                1385
```

FIG. 5F

```
GGC AGC AGC GCC TAC GAT ACG GTT TCC GGT ATC GAG AAC GTG GTG GGC      5187
Gly Ser Ser Ala Tyr Asp Thr Val Ser Gly Ile Glu Asn Val Val Gly
            1390            1395            1400

ACG GAA CTG GCC GAC CGC ATC ACG GGC GAT GCG CAG GCC AAC GTG CTG      5235
Thr Glu Leu Ala Asp Arg Ile Thr Gly Asp Ala Gln Ala Asn Val Leu
    1405            1410            1415

CGC GGC GCG GGT GGC GCC GAC GTG CTT GCG GGC GGC GAG GGC GAC GAT      5283
Arg Gly Ala Gly Gly Ala Asp Val Leu Ala Gly Gly Glu Gly Asp Asp
1420            1425            1430            1435

GTG CTG CTG GGC GGC GAC GGC GAC GAC CAG CTG TCG GGC GAC GCC GGA      5331
Val Leu Leu Gly Gly Asp Gly Asp Asp Gln Leu Ser Gly Asp Ala Gly
                1440            1445            1450

CGC GAT CGC TTG TAC GGC GAA GCC GGT GAC GAC TGG TTC TTC CAG GAT      5379
Arg Asp Arg Leu Tyr Gly Glu Ala Gly Asp Asp Trp Phe Phe Gln Asp
            1455            1460            1465

GCC GCC AAT GCC GGC AAT CTG CTC GAC GGC GGC GAC GGC CGC GAT ACC      5427
Ala Ala Asn Ala Gly Asn Leu Leu Asp Gly Gly Asp Gly Arg Asp Thr
        1470            1475            1480

GTG GAT TTC AGC GGC CCG GGC CGG GGC CTC GAC GCC GGC GCA AAG GGC      5475
Val Asp Phe Ser Gly Pro Gly Arg Gly Leu Asp Ala Gly Ala Lys Gly
    1485            1490            1495

GTA TTC CTG AGC TTG GGC AAG GGG TTC GCC AGC CTG ATG GAC GAA CCC      5523
Val Phe Leu Ser Leu Gly Lys Gly Phe Ala Ser Leu Met Asp Glu Pro
1500            1505            1510            1515

GAA ACC AGC AAC GTG TTG CGC AAT ATC GAG AAC GCC GTG GGC AGC GCG      5571
Glu Thr Ser Asn Val Leu Arg Asn Ile Glu Asn Ala Val Gly Ser Ala
                1520            1525            1530

CGT GAT GAC GTG CTG ATC GGC GAC GCA GGC GCC AAC GTC CTC AAT GGC      5619
Arg Asp Asp Val Leu Ile Gly Asp Ala Gly Ala Asn Val Leu Asn Gly
            1535            1540            1545

CTG GCG GGC AAC GAC GTG CTG TCC GGC GGC GCT GGC GAC GAT GTG CTG      5667
Leu Ala Gly Asn Asp Val Leu Ser Gly Gly Ala Gly Asp Asp Val Leu
        1550            1555            1560

CTG GGC GAC GAG GGC TCG GAC CTG CTC AGC GGC GAT GCG GGC AAC GAC      5715
Leu Gly Asp Glu Gly Ser Asp Leu Leu Ser Gly Asp Ala Gly Asn Asp
    1565            1570            1575

GAT CTG TTC GGC GGG CAG GGC GAT GAT ACT TAT CTG TTC GGG GTC GGG      5763
Asp Leu Phe Gly Gly Gln Gly Asp Asp Thr Tyr Leu Phe Gly Val Gly
1580            1585            1590            1595

TAC GGG CAC GAC ACG ATC TAC GAA TCG GGC GGC GGC CAT GAC ACC ATC      5811
Tyr Gly His Asp Thr Ile Tyr Glu Ser Gly Gly Gly His Asp Thr Ile
                1600            1605            1610

CGC ATC AAC GCG GGG GCG GAC CAG CTG TGG TTC GCG CGC CAG GGC AAC      5859
Arg Ile Asn Ala Gly Ala Asp Gln Leu Trp Phe Ala Arg Gln Gly Asn
            1615            1620            1625

GAC CTG GAG ATC CGC ATT CTC GGC ACC GAC GAT GCA CTT ACC GTG CAC      5907
Asp Leu Glu Ile Arg Ile Leu Gly Thr Asp Asp Ala Leu Thr Val His
        1630            1635            1640
```

FIG. 5G

| | |
|---|---|
| GAC TGG TAT CGC GAC GCC GAT CAC CGG GTG GAA ATC ATC CAT GCC GCC<br>Asp Trp Tyr Arg Asp Ala Asp His Arg Val Glu Ile Ile His Ala Ala<br>　　1645　　　　　　　1650　　　　　　　1655 | 5955 |
| AAC CAG GCG GTA GAC CAG GCA GGC ATC GAA AAG CTG GTC GAG GCA ATG<br>Asn Gln Ala Val Asp Gln Ala Gly Ile Glu Lys Leu Val Glu Ala Met<br>1660　　　　　　　1665　　　　　　　1670　　　　　　　1675 | 6003 |
| GCG CAG TAT CCG GAC CCC GGC GCG GCG GCG GCT GCC CCG CCG GCG GCG<br>Ala Gln Tyr Pro Asp Pro Gly Ala Ala Ala Ala Pro Pro Ala Ala<br>　　　　　　　1680　　　　　　　1685　　　　　　　1690 | 6051 |
| CGC GTG CCG GAC ACG CTG ATG CAG TCC CTG GCT GTC AAC TGG CGC<br>Arg Val Pro Asp Thr Leu Met Gln Ser Leu Ala Val Asn Trp Arg(SEQ ID NO:2)<br>　　　　　1695　　　　　　　1700　　　　　　　1705 | 6096 |
| TGAAGCGCCG TGAATCACGG CCCGCCTGCC TCGCGCGGCG GCGCCGTCTC TTTGCGTTCT | 6156 |
| TCTCCGAGGT ATTTCCCATC ATGACGTCGC CCGTGGCGCA ATGCGCCAGC GTGCCCGATT | 6216 |
| CCGGGTTGCT CTGCCTGGTC ATGCTGGCTC GCTATCACGG ATTGGCAGCC GATCCCGAGC | 6276 |
| AGTTGCGGCA TGAGTTCGCC GAGCAGGCAT TCTGTAGCGA AACGATACAG CCTGGCGGCG | 6336 |
| CGCCGGGTCG GCCTGAAAGT GCGGCGGCAC CGACCCGCGC CGGCGCGGCT GCCACGCGCG | 6396 |
| CCGCTGCCGG CCATCGCGCT GGACCGGCAG GCGGCTACT TTGTT (SEQ ID NO:1) | 6441 |

FIG. 5H

Séquence AC-Hly B. bronchiseptica

```
ATG CAG CAA TCG CAT CAG GCT GGT TAC GCA AAC GCC GCC GAC CGG GAG     48
Met Gln Gln Ser His Gln Ala Gly Tyr Ala Asn Ala Ala Asp Arg Glu

TCT GGC ATC CCC GCA GCC GTA CTC GAT GGC ATC AAG GCC GTG GCG AAG     96
Ser Gly Ile Pro Ala Ala Val Leu Asp Gly Ile Lys Ala Val Ala Lys

GAA AAA AAC GCC ACA TTG ATG TTC CGC CTG GTC AAC CCC CAT TCC ACC    144
Glu Lys Asn Ala Thr Leu Met Phe Arg Leu Val Asn Pro His Ser Thr

AGC CTG ATT GCC GAA GGG GTG GCC ACC AAA GGA TTG GGC GTG CAC GCC    192
Ser Leu Ile Ala Glu Gly Val Ala Thr Lys Gly Leu Gly Val His Ala

AAG TCG TCC GAT TGG GGG TTG CAG GCG GGC TAC ATT CCC GTC AAC CCG    240
Lys Ser Ser Asp Trp Gly Leu Gln Ala Gly Tyr Ile Pro Val Asn Pro

AAT CTT TCC AAA CTG TTC GGC CGT GCG CCC GAG GTG ATC GCG CGG GCC    288
Asn Leu Ser Lys Leu Phe Gly Arg Ala Pro Glu Val Ile Ala Arg Ala

GAC AAC GAC GTC AAC AGC AGC CTG GCG CAT GGC CAT ACC GCG GTC GAC    336
Asp Asn Asp Val Asn Ser Ser Leu Ala His Gly His Thr Ala Val Asp

CTG ACG CTG TCG AAA GAG CGG CTT GAC TAT CTG CGG CAA GCG GGC CTG    384
Leu Thr Leu Ser Lys Glu Arg Leu Asp Tyr Leu Arg Gln Ala Gly Leu

GTC ACC GGC ATG GCC GAT GGC GTG GTC GCG AGC AAC CAC GCA GGC TAC    432
Val Thr Gly Met Ala Asp Gly Val Val Ala Ser Asn His Ala Gly Tyr

GAG CAG TTC GAG TTT CGC GTG AAG GAA ACC TCG GAC GGG CGC TAT GCC    480
Glu Gln Phe Glu Phe Arg Val Lys Glu Thr Ser Asp Gly Arg Tyr Ala

GTG CAG TAT CGC CGC AAG GGC GGC GAC GAT TTC GAG GCG GTC AAG GTG    528
Val Gln Tyr Arg Arg Lys Gly Gly Asp Asp Phe Glu Ala Val Lys Val

ATC GGC AAT GCC GCC GGT ATT CCA CTG ACG GCG GAT ATC GAC ATG TTC    576
Ile Gly Asn Ala Ala Gly Ile Pro Leu Thr Ala Asp Ile Asp Met Phe

GCC ATC ATG CCG CAT CTG TCC AAC TTC CGC GAC TCG GCG CGC AGT TCG    624
Ala Ile Met Pro His Leu Ser Asn Phe Arg Asp Ser Ala Arg Ser Ser

GTG ACC AGC GGC GAT TCG GTG ACC GAT TAC CTG GCG CGC ACG CGG CGG    672
Val Thr Ser Gly Asp Ser Val Thr Asp Tyr Leu Ala Arg Thr Arg Arg

GCC GCC AGC GAG GCC ACG GGC GGC CTG GAT CGC GAA CGC ATC GAC TTG    720
Ala Ala Ser Glu Ala Thr Gly Gly Leu Asp Arg Glu Arg Ile Asp Leu

TTG TGG AAA ATC GCT CGC GCC GGC GCC CGT TCC GCA GTG GGC ACC GAG    768
Leu Trp Lys Ile Ala Arg Ala Gly Ala Arg Ser Ala Val Gly Thr Glu

GCG CGT CGC CAG TTC CGC TAC GAC GGC GAC ATG AAT ATC GGC GTG ATC    816
Ala Arg Arg Gln Phe Arg Tyr Asp Gly Asp Met Asn Ile Gly Val Ile

ACC GAT TTC GAG CTG GAA GTG CGC AAT GCG CTG AAC AGG CGG GCG CAC    864
Thr Asp Phe Glu Leu Glu Val Arg Asn Ala Leu Asn Arg Arg Ala His

GCG GTC GGC AGG CAG GAC GTG GTC CAG CAT GGC ACT GAG CAG AAC AAT    912
Ala Val Gly Arg Gln Asp Val Val Gln His Gly Thr Glu Gln Asn Asn

CCT TTC CCG GAG GCA GAT GAG AAG ATT TTC GTC GTA TCG GCC ACC GGT    960
Pro Phe Pro Glu Ala Asp Glu Lys Ile Phe Val Val Ser Ala Thr Gly

GAA AGC CAG ATG CTC ACG CGC GGG CAA CTG AAG GAA TAC ATT GGC CAG   1008
Glu Ser Gln Met Leu Thr Arg Gly Gln Leu Lys Glu Tyr Ile Gly Gln
```

FIG. 6A

| | |
|---|---|
| CAG CGC GGC GAG GGC TAT GTC TTC TAC GAG AAC CGT GCG TAC GGC GTG<br>Gln Arg Gly Glu Gly Tyr Val Phe Tyr Glu Asn Arg Ala Tyr Gly Val | 1056 |
| GCG GGG AAA AGC CTG TTC GAC GAT GGG CTG GGA GCC GCG CCC GGC GTG<br>Ala Gly Lys Ser Leu Phe Asp Asp Gly Leu Gly Ala Ala Pro Gly Val | 1104 |
| CCG GGG CGA CGT TCG AAG TCC TCG CCG GAT GTA CTG GAA ACG GTG CCG<br>Pro Gly Arg Arg Ser Lys Ser Ser Pro Asp Val Leu Glu Thr Val Pro | 1152 |
| GCG TCA CCC GGA TTG CGG CGG CCG TCG CTG GGC GCA GTG GAA CGC CAG<br>Ala Ser Pro Gly Leu Arg Arg Pro Ser Leu Gly Ala Val Glu Arg Gln | 1200 |
| GAT TCC GGC TAT GAC AGC CTT GAT GGG GTG GGA TCG CGA TCG TTC TCG<br>Asp Ser Gly Tyr Asp Ser Leu Asp Gly Val Gly Ser Arg Ser Phe Ser | 1248 |
| TTG GGC GAG GTG TCC GAC ATG GCC GCC GTG GAA GCG GCG GAA CTG GAA<br>Leu Gly Glu Val Ser Asp Met Ala Ala Val Glu Ala Ala Glu Leu Glu | 1296 |
| ATG ACC CGG CAA GTC TTG CAC GCC GGG GCG CGG CAG GAC GAT GCC GAG<br>Met Thr Arg Gln Val Leu His Ala Gly Ala Arg Gln Asp Asp Ala Glu | 1344 |
| CCG GGC GTG AGC GGT GCG TCG GCG CAC TGG GGG CAG CGG GCG CTG CAG<br>Pro Gly Val Ser Gly Ala Ser Ala His Trp Gly Gln Arg Ala Leu Gln | 1392 |
| GGC GCC CAG GCG GTG GCG GCG GCG CAG CGG CTG GTT CAT GCC ATT GCC<br>Gly Ala Gln Ala Val Ala Ala Ala Gln Arg Leu Val His Ala Ile Ala | 1440 |
| CTG ATG ACG CAA TTC GGC CGG GCC GGT TCC ACC AAC ACG CCG CAG GAA<br>Leu Met Thr Gln Phe Gly Arg Ala Gly Ser Thr Asn Thr Pro Gln Glu | 1488 |
| GCG GCC TCG TTG TCG GCG GCC GTG TTC GGC TTG GGC GAG GCC AGC AGC<br>Ala Ala Ser Leu Ser Ala Ala Val Phe Gly Leu Gly Glu Ala Ser Ser | 1536 |
| GCC GTG GCC GAA ACC GTG AGC GGT TTT TTC CGC GGG TCT TCG CGC TGG<br>Ala Val Ala Glu Thr Val Ser Gly Phe Phe Arg Gly Ser Ser Arg Trp | 1584 |
| GCC GGC GGT TTC GGC GTG GCT GGC GGC GCG ATG GCG CTG GGA GGC GGC<br>Ala Gly Gly Phe Gly Val Ala Gly Gly Ala Met Ala Leu Gly Gly Gly | 1632 |
| ATC GGC GCC GTT GGC GCC GGG ATG TCG TTG ACC GAT GAC GCG CCG GCC<br>Ile Gly Ala Val Gly Ala Gly Met Ser Leu Thr Asp Asp Ala Pro Ala | 1680 |
| GGA CAG AAG GCC GCC GCC GGC GCC GAG ATC GCG CTG CAG TTG ACA GGT<br>Gly Gln Lys Ala Ala Ala Gly Ala Glu Ile Ala Leu Gln Leu Thr Gly | 1728 |
| GGA ACG GTC GAG CTG GCT TCT TCC ATC GCG TTG GCG CTG GCC GCG GCG<br>Gly Thr Val Glu Leu Ala Ser Ser Ile Ala Leu Ala Leu Ala Ala Ala | 1776 |
| CGC GGC GTG ACC AGC GGC TTG CAG GTG GCG GGG GCG TCG GCC GGG GCG<br>Arg Gly Val Thr Ser Gly Leu Gln Val Ala Gly Ala Ser Ala Gly Ala | 1824 |
| GCT GCC GGC GCA TTG GCC GCG GCG CTC AGT CCC ATG GAG ATC TAC GGC<br>Ala Ala Gly Ala Leu Ala Ala Ala Leu Ser Pro Met Glu Ile Tyr Gly | 1872 |
| CTG GTG CAG CAA TCG CAC TAT GCG GAT CAG CTG GAC AAG CTG GCG CAG<br>Leu Val Gln Gln Ser His Tyr Ala Asp Gln Leu Asp Lys Leu Ala Gln | 1920 |
| GAA TCG AGC GCA TAC GGT TAC GAG GGC GAC GCC TTG CTG GCC CAG CTG<br>Glu Ser Ser Ala Tyr Gly Tyr Glu Gly Asp Ala Leu Leu Ala Gln Leu | 1968 |
| TAT CGC GAC AAG ACG GCC GCC GAG GGC GCC GTC GCC GGC GTC TCC GCC<br>Tyr Arg Asp Lys Thr Ala Ala Glu Gly Ala Val Ala Gly Val Ser Ala | 2016 |

FIG. 6B

```
GTC CTG AGC ACG GTG GGG GCT GCG GTG TCG ATC GCC GCG GCG GCC AGC    2064
Val Leu Ser Thr Val Gly Ala Ala Val Ser Ile Ala Ala Ala Ala Ser

GTG GTA GGC GCC CCG GTG GCG GTG GTC ACT TCC TTG TTG ACC GGG GCT    2112
Val Val Gly Ala Pro Val Ala Val Val Thr Ser Leu Leu Thr Gly Ala

CTC AAC GGC ATC CTG CGC GGC GTG CAG CAG CCC ATC ATC GAA AAG CTG    2160
Leu Asn Gly Ile Leu Arg Gly Val Gln Gln Pro Ile Ile Glu Lys Leu

GCC AAT GAT TAC GCT CGC AAG ATC GAC GAG CTG GGC GGG CCG CAA GCG    2208
Ala Asn Asp Tyr Ala Arg Lys Ile Asp Glu Leu Gly Gly Pro Gln Ala

TAC TTC GAG AAA AAC CTG CAG GCG CGT CAC GAA CAA CTG GCC AAT TCG    2256
Tyr Phe Glu Lys Asn Leu Gln Ala Arg His Glu Gln Leu Ala Asn Ser

GAC GGC CTA CGG AAA ATG CTG GCC GAC CTG CAG GCC GGG TGG AAC GCC    2304
Asp Gly Leu Arg Lys Met Leu Ala Asp Leu Gln Ala Gly Trp Asn Ala

AGC AGC GTG ATC GGG GTG CAG ACG ACA GAG ATT TCC AAG TCG GCG CTC    2352
Ser Ser Val Ile Gly Val Gln Thr Thr Glu Ile Ser Lys Ser Ala Leu

GAA CTG GCC GCC ATT ACC GGC AAC GCG GAC AAC CTG AAA TCC GCC GAC    2400
Glu Leu Ala Ala Ile Thr Gly Asn Ala Asp Asn Leu Lys Ser Ala Asp

GTG TTC GTG GAC CGC TTC ATC CAG GGC GAG CGG GTG GCC GGC CAG CCG    2448
Val Phe Val Asp Arg Phe Ile Gln Gly Glu Arg Val Ala Gly Gln Pro

GTG GTA CTC GAC GTC GCC GCC GGC GGC ATC GAT ATC GCC AGC CGC AAG    2496
Val Val Leu Asp Val Ala Ala Gly Gly Ile Asp Ile Ala Ser Arg Lys

GGC GAG CGG CCG GCG CTG ACG TTC ATC ACG CCG CTG GCC GCG CCA GGA    2544
Gly Glu Arg Pro Ala Leu Thr Phe Ile Thr Pro Leu Ala Ala Pro Gly

GAA GAG CAG CGC CGG CGC ACG AAA ACG GGC AAG AGC GAA TTC ACC ACA    2592
Glu Glu Gln Arg Arg Arg Thr Lys Thr Gly Lys Ser Glu Phe Thr Thr

TTC GTC GAG ATC GTG GGC AAG CAG GAC CGC TGG CGC ATC CGG GAC GGC    2640
Phe Val Glu Ile Val Gly Lys Gln Asp Arg Trp Arg Ile Arg Asp Gly

GCG GCC GAC ACC ACC ATC GAT CTG GCC AAG GTG GTG TCG CAA CTG GTC    2688
Ala Ala Asp Thr Thr Ile Asp Leu Ala Lys Val Val Ser Gln Leu Val

GAC GCC AAT GGC GTG CTC AAG CAC AGC ATC AAA CTG GAG GTG ATC GGC    2736
Asp Ala Asn Gly Val Leu Lys His Ser Ile Lys Leu Glu Val Ile Gly

GGA GAT GGC GAT GAT GTC GTG CTT GCC AAT GCT TCG CGC ATC CAT TAC    2784
Gly Asp Gly Asp Asp Val Val Leu Ala Asn Ala Ser Arg Ile His Tyr

GAC GGC GGC GCG GGA ACC AAC ACG GTC AGC TAT GCC GCC CTG GGC CGA    2832
Asp Gly Gly Ala Gly Thr Asn Thr Val Ser Tyr Ala Ala Leu Gly Arg

CAG GAT TCC ATT ACC GTG TCC GCC GAC GGG GAA CGT TTC AAC GTG CGC    2880
Gln Asp Ser Ile Thr Val Ser Ala Asp Gly Glu Arg Phe Asn Val Arg

AAG CAG TTG AAC AAC GCC AAC GTG TAT CGC GAA GGC GTG GCT ACC CAG    2928
Lys Gln Leu Asn Asn Ala Asn Val Tyr Arg Glu Gly Val Ala Thr Gln

AAA ACC GCC TAC GGC AAG CGC ACG GAG AAT GTC CAA TAC CGC CAT GTC    2976
Lys Thr Ala Tyr Gly Lys Arg Thr Glu Asn Val Gln Tyr Arg His Val

GAG CTG GCC CGT GTC GGG CAA CTG GTG GAG GTC GAC ACG CTC GAG CAT    3024
Glu Leu Ala Arg Val Gly Gln Leu Val Glu Val Asp Thr Leu Glu His
```

FIG. 6C

```
GTG CAG CAC ATC ATC GGC GGG GCC GGC AAC GAT TCG ATC ACC GGC AAT      3072
Val Gln His Ile Ile Gly Gly Ala Gly Asn Asp Ser Ile Thr Gly Asn

GCG CAC GAC AAC TTC CTG GCC GGC GGG GCG GGC GAC GAC AGG CTG GAT      3120
Ala His Asp Asn Phe Leu Ala Gly Gly Ala Gly Asp Asp Arg Leu Asp

GGC GGC GCC GGC AAC GAC ACA CTG GTC GGC GGC GAG GGC CAC AAC ACG      3168
Gly Gly Ala Gly Asn Asp Thr Leu Val Gly Gly Glu Gly His Asn Thr

GTC GTC GGC GGC GCT GGC GAC GAC GTA TTC CTG CAG GAC CTG GGG GTA      3216
Val Val Gly Gly Ala Gly Asp Asp Val Phe Leu Gln Asp Leu Gly Val

TGG AGC AAC CAG CTC GAT GGC GGC GCG GGC GTC GAT ACC GTG AAG TAC      3264
Trp Ser Asn Gln Leu Asp Gly Gly Ala Gly Val Asp Thr Val Lys Tyr

AAC GTG CAC CAG CCT TCC GAG GAA CGC CTC GAA CGC ATG GGC GAC ACG      3312
Asn Val His Gln Pro Ser Glu Glu Arg Leu Glu Arg Met Gly Asp Thr

GGC ATC CAT GCC GAT CTT CAA AAG GGC ACG GTC GAG AAG TGG CCG GCC      3360
Gly Ile His Ala Asp Leu Gln Lys Gly Thr Val Glu Lys Trp Pro Ala

CTG AAC CTG TTC AGC GTC GAC CAT GTC AAG AAT ATC GAG AAT CTG CAC      3408
Leu Asn Leu Phe Ser Val Asp His Val Lys Asn Ile Glu Asn Leu His

GGC TCC AGC CTG AAC GAC AGC ATC GCC GGC GAC GAC CGG GAC AAC GAG      3456
Gly Ser Ser Leu Asn Asp Ser Ile Ala Gly Asp Asp Arg Asp Asn Glu

CTC TGG GGC GAC GAT GGC AAC GAC ACG ATA CAC GGC CGG GGC GGC GAC      3504
Leu Trp Gly Asp Asp Gly Asn Asp Thr Ile His Gly Arg Gly Gly Asp

GAT ATC CTG CGC GGC GGC CTG GGC CTG GAC ACG CTG TAT GGC GAG GAC      3552
Asp Ile Leu Arg Gly Gly Leu Gly Leu Asp Thr Leu Tyr Gly Glu Asp

GGC AAC GAC ATC TTC CTG CAG GAC GAC GAG ACC GTC AGC GAT GAC ATC      3600
Gly Asn Asp Ile Phe Leu Gln Asp Asp Glu Thr Val Ser Asp Asp Ile

GAC GGT GGC GCG GGA CTG GAC ACC GTC GAC TAT TCC GCC ATG ATC CAT      3648
Asp Gly Gly Ala Gly Leu Asp Thr Val Asp Tyr Ser Ala Met Ile His

GCA GGC AAG ATC GTT GCG CCG CAT GAA TAC GGC TTC GGG ATC GAG GCG      3696
Ala Gly Lys Ile Val Ala Pro His Glu Tyr Gly Phe Gly Ile Glu Ala

GAC CTG TCC GAA GGG TGG GTG CGC AAG GCG GCC CGG CGC GGC ATG GAC      3744
Asp Leu Ser Glu Gly Trp Val Arg Lys Ala Ala Arg Arg Gly Met Asp

TAC TAC GAC AGT GTC CGC AGT GTC GAA AAC GTC ATC GGC ACG AGC ATG      3792
Tyr Tyr Asp Ser Val Arg Ser Val Glu Asn Val Ile Gly Thr Ser Met

AAG GAT GTG CTC ATC GGC GAC GCG CAA GCC AAT ACC CTG ATG GGC CAG      3840
Lys Asp Val Leu Ile Gly Asp Ala Gln Ala Asn Thr Leu Met Gly Gln

GGC GGC GAC GAT ACC GTG CGC GGC GGC GAC GGC GAT GAT CTG CTG TTC      3888
Gly Gly Asp Asp Thr Val Arg Gly Gly Asp Gly Asp Asp Leu Leu Phe

GGC GGC GAC GGC AAC GAC ATG CTG TAT GGA GAC GCC GGC AAC GAC ACC      3936
Gly Gly Asp Gly Asn Asp Met Leu Tyr Gly Asp Ala Gly Asn Asp Thr

CTC TAC GGA GGG CTG GGC GAC GAT ACC CTT GAA GGC GGC GCG GGC AAC      3984
Leu Tyr Gly Gly Leu Gly Asp Asp Thr Leu Glu Gly Gly Ala Gly Asn

GAT TGG TTC GGC CAG ACG CCG GCG CGC GAG CAT GAC GTG CTG CGC GGC      4032
Asp Trp Phe Gly Gln Thr Pro Ala Arg Glu His Asp Val Leu Arg Gly
```

FIG. 6D

```
GGG GCT GGG GTG GAT ACC GTG GAT TAC AGC CAG GCG GGC GCG CAT GCC    4080
Gly Ala Gly Val Asp Thr Val Asp Tyr Ser Gln Ala Gly Ala His Ala

GGC GTT GCC ACG GGT CGC ATC GGG CTG GGT ATT CTG GCG GAC CTG GGC    4128
Gly Val Ala Thr Gly Arg Ile Gly Leu Gly Ile Leu Ala Asp Leu Gly

GCC GGC CGC GTC GAC AAG CTG GGC GAG GCC GGC AGC AGC GCC TAC GAT    4176
Ala Gly Arg Val Asp Lys Leu Gly Glu Ala Gly Ser Ser Ala Tyr Asp

ACG GTT TCC GGC ATC GAA AAT GTG GTG GGC ACG GAA CTG GCC GAC CGC    4224
Thr Val Ser Gly Ile Glu Asn Val Val Gly Thr Glu Leu Ala Asp Arg

ATC ACG GGC GAT GCG CAG GCC AAC GTA CTG CGC GGC GCG GGT GGC GCC    4272
Ile Thr Gly Asp Ala Gln Ala Asn Val Leu Arg Gly Ala Gly Gly Ala

GAC GTG CTT GCG GGC GGC GAG GGC GAC GAT GTG CTG CTG GGC GGC GAC    4320
Asp Val Leu Ala Gly Gly Glu Gly Asp Asp Val Leu Leu Gly Gly Asp

GGC GAC GAC CAG CTG TCG GGC GAC GCC GGA CGC GAC CGC TTG TAC GGC    4368
Gly Asp Asp Gln Leu Ser Gly Asp Ala Gly Arg Asp Arg Leu Tyr Gly

GAA GCC GGT GAC GAC TGG TTC TTC CAG GAT GCC GCC AAT GCC GGC AAT    4416
Glu Ala Gly Asp Asp Trp Phe Phe Gln Asp Ala Ala Asn Ala Gly Asn

CTG CTC GAC GGT GGT GAC GGC AAC GAT ACC GTG GAT TTC AGC GGC CCG    4464
Leu Leu Asp Gly Gly Asp Gly Asn Asp Thr Val Asp Phe Ser Gly Pro

GGC CGG GGC CTC GAC GCC GGC GCA AAG GGC GTA TTC CTG AGC CTG GGC    4512
Gly Arg Gly Leu Asp Ala Gly Ala Lys Gly Val Phe Leu Ser Leu Gly

AAG GGG TTC GCC AGC CTG ATG GAC GAA CCC GAA ACC AGC AAC GTG TTG    4560
Lys Gly Phe Ala Ser Leu Met Asp Glu Pro Glu Thr Ser Asn Val Leu

CGC CAT ATC GAG AAC GCC GTG GGC AGC GTG CGT GAT GAC GTG CTG ATC    4608
Arg His Ile Glu Asn Ala Val Gly Ser Val Arg Asp Asp Val Leu Ile

GGC GAC GCA GGC GCC AAC GTC CTC AAT GGC CTG GCG GGC AAC GAC GTG    4656
Gly Asp Ala Gly Ala Asn Val Leu Asn Gly Leu Ala Gly Asn Asp Val

CTG TCG GCG GCG CCG GCG GAC GAT GTG CTG CTG GGC GAC GAG GGC TCG    4704
Leu Ser Ala Ala Pro Ala Asp Asp Val Leu Leu Gly Asp Glu Gly Ser

GAC CTG CTC AGC GGC GAT GCG GGC AAC GAC GAT CTG TTC GGC GGG CAG    4752
Asp Leu Leu Ser Gly Asp Ala Gly Asn Asp Asp Leu Phe Gly Gly Gln

GGC GAT GAT ACC TAT CTG TTC GGG GCC GGG TAC GGA CAT GAC ACG ATC    4800
Gly Asp Asp Thr Tyr Leu Phe Gly Ala Gly Tyr Gly His Asp Thr Ile

TAC GAA TCG GGC GGC GGC CAT GAC ACC ATC CGT ATC AAC GCG GGG GCG    4848
Tyr Glu Ser Gly Gly Gly His Asp Thr Ile Arg Ile Asn Ala Gly Ala

GAC CAG CTG TGG TTT GCG CGC CAG GGC AAC GAC CTG GAG ATC CGC ATT    4896
Asp Gln Leu Trp Phe Ala Arg Gln Gly Asn Asp Leu Glu Ile Arg Ile

CTT GGC ACC GAC GAT GCA CTT ACC GTG CAC GAC TGG TAT CGC GAC GCC    4944
Leu Gly Thr Asp Asp Ala Leu Thr Val His Asp Trp Tyr Arg Asp Ala

GAT CAC CGG GTG GAA GCC ATC CAT GCC GCC AAC CAG GCC ATA GAC CCG    4992
Asp His Arg Val Glu Ala Ile His Ala Ala Asn Gln Ala Ile Asp Pro
```

FIG. 6E

```
GCC GGC ATC GAA AAG CTG GTC GAG GCA ATG GCG CAG TAC CCG GAC CCC        5040
Ala Gly Ile Glu Lys Leu Val Glu Ala Met Ala Gln Tyr Pro Asp Pro

GGC GCG GCG GCG GCT GCC CCG CCG GCG GCG CGC GTG CCG GAC ACG CTG        5088
Gly Ala Ala Ala Ala Ala Pro Pro Ala Ala Arg Val Pro Asp Thr Leu

ATG CAG TCC CTG GCT GTC AAC TGG CGC TGA (SEQ ID NO:3)                  5118
Met Gln Ser Leu Ala Val Asn Trp Arg     (SEQ ID NO:4)
```

FIG. 6F

SEQUENCE LISTING

```
(1) GENERAL INFORMATION:

(iii) NUMBER OF SEQUENCES: 4

(2) INFORMATION FOR SEQ ID NO: 1:

(i) SEQUENCE CHARACTERISTICS:
          (A) LENGTH: 6441 base pairs
          (B) TYPE: nucleic acid
          (C) STRANDEDNESS: double
          (D) TOPOLOGY: linear (ii) MOLECULE TYPE: DNA (genomic)

(ix) FEATURE:
          (A) NAME/KEY: CDS
          (B) LOCATION: 979..6096
          (D) OTHER INFORMATION:/note= "AMINO ACID SEQUENCE
               CORRESPONDING TO THE NUCLEOTIDE SEQUENCE OF THE GENE
               CODING FOR THE B. Pertussis AC-Hly"

(xi) SEQUENCE DESCRIPTION: SEQ ID NO: 1:

CGATCATTCG GCATGTACGG TCCAGCTGCG CGCGAGCGGC GGCCGCGTCC AGCGCGCGGC     60

CTCGGTACTC CTTGACGCGC GCGGTGTCGC CGCCGCGCCG AACGCGCAGC GAACGGCCCA    120

CGCTGTCGGG GTGCCGTTCG GCCAGCGCGC GGCGCAGCGC ACGATTGTCG TCGCGCGAGA    180

ATGGCGCGAT CCAGTCGATG ATCCACAGTC GGTCGCCGCA GTTCCAGGCA TTCCCGCCCA    240
```

-continued

```
GCGACGAGGG CGCCATGACA TAGGAGAGTT CGGTGTCGGC GTCCATTAGG GCCCAGCTGC    300

AGTATGCAAC CGGCACGTCA TTGCATCGCA GCAGAATGTA TTGGCCCAGT TGAATCGGCG    360

CGAGCGCTGT TGCGTGCGAG CAGATGCACC GGCCAGTCGC GGTGCATGGG AGAGTTCATC    420

CACAGCCAGG CAATATTGCC CAGTGCCGCG AAGTCGTCGG TGGGATTGAG GAGGGAGGGC    480

GCTTGGGCGG ACGGAAGCAT GACATCGGTG CATGGTGGAG CGGGGGGCAT ATTCCGTGTT    540

GGGTGCGCGC ATGGCAAGCC GCCGGCGCAT CATGGTTGCG CCGGAATGGC TTTTCTTACA    600

TGTTTCCAGG ATATGTCCGT ATTTCGGGCG ATGCCTCGGT CGCGGCGCCT GCTTTTGTCG    660

AACATGTGCA ATGTTGTTGT CGCGATCGCG TTGGCGCTTG CTCGCTTATT TATCTCCCTT    720

GAAGCCTTGT TCTTCTTTTC ATTAGAAAGA AATATGCGCT TTGTGTTTAG GATGATTTTC    780

CTGTCCAGT AGGGTGGATC CAAATTTTCC GGATTGGTGG GAATTTGTGC ATTTTCACTG    840

CGAATGTTGG AATAATTTCG CCCATCGTCA TACGACATGC TGGATGTTTG GTTCTTGCAG    900

AAGGATGAGG TTCTGAGCGC TACACACCGG TTGCGTCGGT GCGAATCCGT TCAATCGACT    960

ACTTATCGAC AGATCCAC ATG CAG CAA TCG CAT CAG GCT GGT TAC GCA AAC    1011
                    Met Gln Gln Ser His Gln Ala Gly Tyr Ala Asn
                     1               5                  10

GCC GCC GAC CGG GAG TCT GGC ATC CCC GCA GCC GTA CTC GAT GGC ATC    1059
Ala Ala Asp Arg Glu Ser Gly Ile Pro Ala Ala Val Leu Asp Gly Ile
            15                  20                  25

AAG GCC GTG GCG AAG GAA AAA AAC GCC ACA TTG ATG TTC CGC CTG GTC    1107
Lys Ala Val Ala Lys Glu Lys Asn Ala Thr Leu Met Phe Arg Leu Val
        30                  35                  40

AAC CCC CAT TCC ACC AGC CTG ATT GCC GAA GGG GTG GCC ACC AAA GGA    1155
Asn Pro His Ser Thr Ser Leu Ile Ala Glu Gly Val Ala Thr Lys Gly
    45                  50                  55

TTG GGC GTG CAC GCC AAG TCG TCC GAT TGG GGG TTG CAG GCG GGC TAC    1203
Leu Gly Val His Ala Lys Ser Ser Asp Trp Gly Leu Gln Ala Gly Tyr
60                  65                  70                  75

ATT CCC GTC AAC CCG AAT CTT TCC AAA CTG TTC GGC CGT GCG CCC GAG    1251
Ile Pro Val Asn Pro Asn Leu Ser Lys Leu Phe Gly Arg Ala Pro Glu
                80                  85                  90

GTG ATC GCG CGG GCC GAC AAC GAC GTC AAC AGC AGC CTG GCG CAT GGC    1299
Val Ile Ala Arg Ala Asp Asn Asp Val Asn Ser Ser Leu Ala His Gly
            95                 100                 105

CAT ACC GCG GTC GAC CTG ACG CTG TCG AAA GAG CGG CTT GAC TAT CTG    1347
His Thr Ala Val Asp Leu Thr Leu Ser Lys Glu Arg Leu Asp Tyr Leu
        110                 115                 120

CGG CAA GCG GGC CTG GTC ACC GGC ATG GCC GAT GGC GTG GTC GCG AGC    1395
Arg Gln Ala Gly Leu Val Thr Gly Met Ala Asp Gly Val Val Ala Ser
    125                 130                 135

AAC CAC GCA GGC TAC GAG CAG TTC GAG TTT CGC GTG AAG GAA ACC TCG    1443
Asn His Ala Gly Tyr Glu Gln Phe Glu Phe Arg Val Lys Glu Thr Ser
140                 145                 150                 155

GAC GGG CGC TAT GCC GTG CAG TAT CGC CGC AAG GGC GGC GAC GAT TTC    1491
Asp Gly Arg Tyr Ala Val Gln Tyr Arg Arg Lys Gly Gly Asp Asp Phe
                160                 165                 170

GAG GCG GTC AAG GTG ATC GGC AAT GCC GCC GGT ATT CCA CTG ACG GCG    1539
Glu Ala Val Lys Val Ile Gly Asn Ala Ala Gly Ile Pro Leu Thr Ala
            175                 180                 185

GAT ATC GAC ATG TTC GCC ATT ATG CCG CAT CTG TCC AAC TTC CGC GAC    1587
Asp Ile Asp Met Phe Ala Ile Met Pro His Leu Ser Asn Phe Arg Asp
        190                 195                 200

TCG GCG CGC AGT TCG GTG ACC AGC GGC GAT TCG GTG ACC GAT TAC CTG    1635
Ser Ala Arg Ser Ser Val Thr Ser Gly Asp Ser Val Thr Asp Tyr Leu
    205                 210                 215
```

| | |
|---|---|
| GCG CGC ACG CGG CGG GCC GCC AGC GAG GCC ACG GGC GGC CTG GAT CGC<br>Ala Arg Thr Arg Arg Ala Ala Ser Glu Ala Thr Gly Gly Leu Asp Arg<br>220                 225                     230                     235 | 1683 |
| GAA CGC ATC GAC TTG TTG TGG AAA ATC GCT CGC GCC GGC GCC CGT TCC<br>Glu Arg Ile Asp Leu Leu Trp Lys Ile Ala Arg Ala Gly Ala Arg Ser<br>             240                     245                     250 | 1731 |
| GCA GTG GGC ACC GAG GCG CGT CGC CAG TTC CGC TAC GAC GGC GAC ATG<br>Ala Val Gly Thr Glu Ala Arg Arg Gln Phe Arg Tyr Asp Gly Asp Met<br>               255                     260                     265 | 1779 |
| AAT ATC GGC GTG ATC ACC GAT TTC GAG CTG GAA GTG CGC AAT GCG CTG<br>Asn Ile Gly Val Ile Thr Asp Phe Glu Leu Glu Val Arg Asn Ala Leu<br>        270                     275                     280 | 1827 |
| AAC AGG CGG GCG CAC GCC GTC GGC GCG CAG GAC GTG GTC CAG CAT GGC<br>Asn Arg Arg Ala His Ala Val Gly Ala Gln Asp Val Val Gln His Gly<br>285                 290                     295 | 1875 |
| ACT GAG CAG AAC AAT CCT TTC CCG GAG GCA GAT GAG AAG ATT TTC GTC<br>Thr Glu Gln Asn Asn Pro Phe Pro Glu Ala Asp Glu Lys Ile Phe Val<br>300                 305                     310                     315 | 1923 |
| GTA TCG GCC ACC GGT GAA AGC CAG ATG CTC ACG CGC GGG CAA CTG AAG<br>Val Ser Ala Thr Gly Glu Ser Gln Met Leu Thr Arg Gly Gln Leu Lys<br>             320                     325                     330 | 1971 |
| GAA TAC ATT GGC CAG CAG CGC GGC GAG GGC TAT GTC TTC TAC GAG AAC<br>Glu Tyr Ile Gly Gln Gln Arg Gly Glu Gly Tyr Val Phe Tyr Glu Asn<br>               335                     340                     345 | 2019 |
| CGT GCA TAC GGC GTG GCG GGG AAA AGC CTG TTC GAC GAT GGG CTG GGA<br>Arg Ala Tyr Gly Val Ala Gly Lys Ser Leu Phe Asp Asp Gly Leu Gly<br>        350                     355                     360 | 2067 |
| GCC GCG CCC GGC GTG CCG AGC GGA CGT TCG AAG TTC TCG CCG GAT GTA<br>Ala Ala Pro Gly Val Pro Ser Gly Arg Ser Lys Phe Ser Pro Asp Val<br>365                 370                     375 | 2115 |
| CTG GAA ACG GTG CCG GCG TCA CCC GGA TTG CGG CGG CCG TCG CTG GGC<br>Leu Glu Thr Val Pro Ala Ser Pro Gly Leu Arg Arg Pro Ser Leu Gly<br>380                 385                     390                     395 | 2163 |
| GCA GTG GAA CGC CAG GAT TCC GGC TAT GAC AGC CTT GAT GGG GTG GGA<br>Ala Val Glu Arg Gln Asp Ser Gly Tyr Asp Ser Leu Asp Gly Val Gly<br>             400                     405                     410 | 2211 |
| TCG CGA TCG TTC TCG TTG GGC GAG GTG TCC GAC ATG GCC GCC GTG GAA<br>Ser Arg Ser Phe Ser Leu Gly Glu Val Ser Asp Met Ala Ala Val Glu<br>               415                     420                     425 | 2259 |
| GCG GCG GAA CTG GAA ATG ACC CGG CAA GTC TTG CAC GCC GGG GCG CGG<br>Ala Ala Glu Leu Glu Met Thr Arg Gln Val Leu His Ala Gly Ala Arg<br>        430                     435                     440 | 2307 |
| CAG GAC GAT GCC GAG CCG GGC GTG AGC GGT GCG TCG GCG CAC TGG GGG<br>Gln Asp Asp Ala Glu Pro Gly Val Ser Gly Ala Ser Ala His Trp Gly<br>445                 450                     455 | 2355 |
| CAG CGG GCG CTG CAG GGC GCC CAG GCG GTG GCG GCG GCG CAG CGG CTG<br>Gln Arg Ala Leu Gln Gly Ala Gln Ala Val Ala Ala Ala Gln Arg Leu<br>460                 465                     470                     475 | 2403 |
| GTT CAT GCC ATT GCC CTG ATG ACG CAA TTC GGC CGG GCC GGT TCC ACC<br>Val His Ala Ile Ala Leu Met Thr Gln Phe Gly Arg Ala Gly Ser Thr<br>             480                     485                     490 | 2451 |
| AAC ACG CCG CAG GAA GCG GCC TCG TTG TCG GCG GCC GTG TTC GGC TTG<br>Asn Thr Pro Gln Glu Ala Ala Ser Leu Ser Ala Ala Val Phe Gly Leu<br>               495                     500                     505 | 2499 |
| GGC GAG GCC AGC AGC GCC GTG GCC GAA ACC GTG AGC GGT TTT TTC CGC<br>Gly Glu Ala Ser Ser Ala Val Ala Glu Thr Val Ser Gly Phe Phe Arg<br>        510                     515                     520 | 2547 |
| GGG TCT TCG CGC TGG GCC GGC GGT TTC GGC GTG GCT GGC GGC GCG ATG<br>Gly Ser Ser Arg Trp Ala Gly Gly Phe Gly Val Ala Gly Gly Ala Met | 2595 |

```
                525                   530                    535
GCG CTG GGA GGC GGC ATC GCC GCG GCC GTT GGC GCC GGG ATG TCG TTG        2643
Ala Leu Gly Gly Gly Ile Ala Ala Ala Val Gly Ala Gly Met Ser Leu
540                 545                 550                 555

ACC GAT GAC GCG CCG GCC GGA CAG AAG GCC GCC GCC GGC GCC GAG ATC        2691
Thr Asp Asp Ala Pro Ala Gly Gln Lys Ala Ala Ala Gly Ala Glu Ile
                560                 565                 570

GCG CTG CAG TTG ACA GGT GGA ACG GTC GAG CTG GCT TCT TCC ATC GCG        2739
Ala Leu Gln Leu Thr Gly Gly Thr Val Glu Leu Ala Ser Ser Ile Ala
            575                 580                 585

TTG GCG CTG GCC GCG GCG CGC GGC GTG ACC AGC GGC TTG CAG GTG GCC        2787
Leu Ala Leu Ala Ala Ala Arg Gly Val Thr Ser Gly Leu Gln Val Ala
        590                 595                 600

GGG GCG TCG GCC GGG GCG GCT GCC GGC GCA TTG GCC GCG GCG CTC AGT        2835
Gly Ala Ser Ala Gly Ala Ala Ala Gly Ala Leu Ala Ala Ala Leu Ser
    605                 610                 615

CCC ATG GAG ATC TAC GGC CTG GTG CAG CAA TCG CAC TAT GCG GAT CAG        2883
Pro Met Glu Ile Tyr Gly Leu Val Gln Gln Ser His Tyr Ala Asp Gln
620                 625                 630                 635

CTG GAC AAG CTG GCG CAG GAA TCG AGC GCA TAC GGT TAC GAG GGC GAC        2931
Leu Asp Lys Leu Ala Gln Glu Ser Ser Ala Tyr Gly Tyr Glu Gly Asp
                640                 645                 650

GCC TTG CTG GCC CAG CTG TAT CGC GAC AAG ACG GCC GCC GAG GGC GCC        2979
Ala Leu Leu Ala Gln Leu Tyr Arg Asp Lys Thr Ala Ala Glu Gly Ala
            655                 660                 665

GTC GCC GGC GTC TCC GCC GTC CTG AGC ACG GTG GGG GCG GCG GTG TCG        3027
Val Ala Gly Val Ser Ala Val Leu Ser Thr Val Gly Ala Ala Val Ser
        670                 675                 680

ATC GCC GCG GCG GCC AGC GTG GTA GGG GCC CCG GTG GCG GTG GTC ACT        3075
Ile Ala Ala Ala Ala Ser Val Val Gly Ala Pro Val Ala Val Val Thr
    685                 690                 695

TCC TTG CTG ACC GGG GCT CTC AAC GGC ATC CTG CGC GGC GTG CAG CAG        3123
Ser Leu Leu Thr Gly Ala Leu Asn Gly Ile Leu Arg Gly Val Gln Gln
700                 705                 710                 715

CCC ATC ATC GAA AAG CTG GCC AAC GAT TAC GCT CGC AAG ATC GAC GAG        3171
Pro Ile Ile Glu Lys Leu Ala Asn Asp Tyr Ala Arg Lys Ile Asp Glu
                720                 725                 730

CTG GGC GGG CCG CAA GCG TAC TTC GAG AAA AAC CTG CAG GCG CGT CAC        3219
Leu Gly Gly Pro Gln Ala Tyr Phe Glu Lys Asn Leu Gln Ala Arg His
            735                 740                 745

GAA CAA CTG GCC AAT TCG GAC GGC CTA CGG AAA ATG CTG GCC GAC CTG        3267
Glu Gln Leu Ala Asn Ser Asp Gly Leu Arg Lys Met Leu Ala Asp Leu
        750                 755                 760

CAG GCC GGT TGG AAC GCC AGC AGC GTG ATC GGG GTG CAG ACG ACA GAG        3315
Gln Ala Gly Trp Asn Ala Ser Ser Val Ile Gly Val Gln Thr Thr Glu
    765                 770                 775

ATC TCC AAG TCG GCG CTC GAA CTG GCC GCC ATT ACC GGC AAC GCG GAC        3363
Ile Ser Lys Ser Ala Leu Glu Leu Ala Ala Ile Thr Gly Asn Ala Asp
780                 785                 790                 785

AAC CTG AAA TCC GTC GAC GTG TTC GTG GAC CGC TTC GTC CAG GGC GAG        3411
Asn Leu Lys Ser Val Asp Val Phe Val Asp Arg Phe Val Gln Gly Glu
                800                 805                 810

CGG GTG GCC GGC CAG CCG GTG GTC CTC GAC GTC GCC GCC GGC GGC ATC        3459
Arg Val Ala Gly Gln Pro Val Val Leu Asp Val Ala Ala Gly Gly Ile
            815                 820                 825

GAT ATC GCC AGC CGC AAG GGC GAG CGG CCG GCG CTG ACG TTC ATC ACG        3507
Asp Ile Ala Ser Arg Lys Gly Glu Arg Pro Ala Leu Thr Phe Ile Thr
        830                 835                 840

CCG CTG GCC GCG CCA GGA GAA GAG CAG CGC CGG CGC ACG AAA ACG GGC        3555
```

```
                Pro Leu Ala Ala Pro Gly Glu Glu Gln Arg Arg Thr Lys Thr Gly
                    845                 850                 855

AAG AGC GAA TTC ACC ACA TTC GTC GAG ATC GTG GGC AAG CAG GAC CGC          3603
Lys Ser Glu Phe Thr Thr Phe Val Glu Ile Val Gly Lys Gln Asp Arg
860                 865                 870                 875

TGG CGC ATC CGG GAC GGC GCG GCC GAC ACC ACC ATC GAT CTG GCC AAG          3651
Trp Arg Ile Arg Asp Gly Ala Ala Asp Thr Thr Ile Asp Leu Ala Lys
                880                 885                 890

GTG GTG TCG CAA CTG GTC GAC GCC AAT GGC GTG CTC AAG CAC AGC ATC          3699
Val Val Ser Gln Leu Val Asp Ala Asn Gly Val Leu Lys His Ser Ile
            895                 900                 905

AAA CTG GAT GTG ATC GGC GGA GAT GGC GAT GAC GTC GTG CTT GCC AAT          3747
Lys Leu Asp Val Ile Gly Gly Asp Gly Asp Asp Val Val Leu Ala Asn
        910                 915                 920

GCT TCG CGC ATC CAT TAT GAC GGC GGC GCG GGC ACC AAC ACG GTC AGC          3795
Ala Ser Arg Ile His Tyr Asp Gly Gly Ala Gly Thr Asn Thr Val Ser
    925                 930                 935

TAT GCC GCC CTG GGT CGA CAG GAT TCC ATT ACC GTG TCC GCC GAC GGG          3843
Tyr Ala Ala Leu Gly Arg Gln Asp Ser Ile Thr Val Ser Ala Asp Gly
940                 945                 950                 955

GAA CGT TTC AAC GTG CGC AAG CAG TTG AAC AAC GCC AAC GTG TAT CGC          3891
Glu Arg Phe Asn Val Arg Lys Gln Leu Asn Asn Ala Asn Val Tyr Arg
                960                 965                 970

GAA GGC GTG GCT ACC CAG ACA ACC GCC TAC GGC AAG CGC ACG GAG AAT          3939
Glu Gly Val Ala Thr Gln Thr Thr Ala Tyr Gly Lys Arg Thr Glu Asn
                975                 980                 985

GTC CAA TAC CGC CAT GTC GAG CTG GCC CGT GTC GGG CAA GTG GTG GAG          3987
Val Gln Tyr Arg His Val Glu Leu Ala Arg Val Gly Gln Val Val Glu
            990                 995                 1000

GTC GAC ACG CTC GAG CAT GTG CAG CAC ATC ATC GGC GGG GCC GGC AAC          4035
Val Asp Thr Leu Glu His Val Gln His Ile Ile Gly Gly Ala Gly Asn
        1005                1010                1015

GAT TCG ATC ACC GGC AAT GCG CAC GAC AAC TTC CTA GCC GGC GGG TCG          4083
Asp Ser Ile Thr Gly Asn Ala His Asp Asn Phe Leu Ala Gly Gly Ser
1020                1025                1030                1035

GGC GAC GAC AGG CTG GAT GGC GGC GCC GGC AAC GAC ACC CTG GTT GGC          4131
Gly Asp Asp Arg Leu Asp Gly Gly Ala Gly Asn Asp Thr Leu Val Gly
                1040                1045                1050

GGC GAG GGC CAA AAC ACG GTC ATC GGC GGC GCC GGC GAC GAC GTA TTC          4179
Gly Glu Gly Gln Asn Thr Val Ile Gly Gly Ala Gly Asp Asp Val Phe
                1055                1060                1065

CTG CAG GAC CTG GGG GTA TGG AGC AAC CAG CTC GAT GGC GGC GCG GGC          4227
Leu Gln Asp Leu Gly Val Trp Ser Asn Gln Leu Asp Gly Gly Ala Gly
            1070                1075                1080

GTC GAT ACC GTG AAG TAC AAC GTG CAC CAG CCT TCC GAG GAG CGC CTC          4275
Val Asp Thr Val Lys Tyr Asn Val His Gln Pro Ser Glu Glu Arg Leu
        1085                1090                1095

GAA CGC ATG GGC GAC ACG GGC ATC CAT GCC GAT CTT CAA AAG GGC ACG          4323
Glu Arg Met Gly Asp Thr Gly Ile His Ala Asp Leu Gln Lys Gly Thr
    1100                1105                1110                1115

GTC GAG AAG TGG CCG GCC CTG AAC CTG TTC AGC GTC GAC CAT GTC AAG          4371
Val Glu Lys Trp Pro Ala Leu Asn Leu Phe Ser Val Asp His Val Lys
                1120                1125                1130

AAT ATC GAG AAT CTG CAC GGC TCC CGC CTA AAC GAC CGC ATC GCC GGC          4419
Asn Ile Glu Asn Leu His Gly Ser Arg Leu Asn Asp Arg Ile Ala Gly
                1135                1140                1145

GAC GAC CAG GAC AAC GAG CTC TGG GGC CAC GAT GGC AAC GAC ACG ATA          4467
Asp Asp Gln Asp Asn Glu Leu Trp Gly His Asp Gly Asn Asp Thr Ile
            1150                1155                1160
```

```
CGC GGC CGG GGC GGC GAC GAC ATC CTG CGC GGC GGC CTG GGC CTG GAC     4515
Arg Gly Arg Gly Gly Asp Asp Ile Leu Arg Gly Gly Leu Gly Leu Asp
        1165                1170                1175

ACG CTG TAT GGC GAG GAC GGC AAC GAC ATC TTC CTG CAG GAC GAC GAG     4563
Thr Leu Tyr Gly Glu Asp Gly Asn Asp Ile Phe Leu Gln Asp Asp Glu
1180                1185                1190                1195

ACC GTC AGC GAT GAC ATC GAC GGC GGC GCG GGG CTG GAC ACC GTC GAC     4611
Thr Val Ser Asp Asp Ile Asp Gly Gly Ala Gly Leu Asp Thr Val Asp
            1200                1205                1210

TAC TCC GCC ATG ATC CAT GCA GGC AAG ATC GTT GCG CCG CAT GAA TAC     4659
Tyr Ser Ala Met Ile His Ala Gly Lys Ile Val Ala Pro His Glu Tyr
                1215                1220                1225

GGC TTC GGG ATC GAG GCG GAC CTG TCC AGG GAA TGG GTG CGC AAG GCG     4707
Gly Phe Gly Ile Glu Ala Asp Leu Ser Arg Glu Trp Val Arg Lys Ala
            1230                1235                1240

TCC GCG CTG GGC GTG GAC TAT TAC GAT AAT GTC CGC AAT GTC GAA AAC     4755
Ser Ala Leu Gly Val Asp Tyr Tyr Asp Asn Val Arg Asn Val Glu Asn
        1245                1250                1255

GTC ATC GGT ACG AGC ATG AAG GAT GTG CTC ATC GGC GAC GCG CAA GCC     4803
Val Ile Gly Thr Ser Met Lys Asp Val Leu Ile Gly Asp Ala Gln Ala
1260                1265                1270                1275

AAT ACC CTG ATG GGC CAG GGC GGC GAC GAT ACC GTG CGC GGC GGC GAC     4851
Asn Thr Leu Met Gly Gln Gly Gly Asp Asp Thr Val Arg Gly Gly Asp
            1280                1285                1290

GGC GAT GAT CTG CTG TTC GGC GGC GAC GGC AAC GAC ATG CTG TAT GGC     4899
Gly Asp Asp Leu Leu Phe Gly Gly Asp Gly Asn Asp Met Leu Tyr Gly
        1295                1300                1305

GAC GCC GGC AAC GAC ACC CTC TAC GGG GGG CTG GGC GAC GAT ACC CTT     4947
Asp Ala Gly Asn Asp Thr Leu Tyr Gly Gly Leu Gly Asp Asp Thr Leu
            1310                1315                1320

GAA GGC GGC GCG GGC AAC GAT TGG TTC GGC CAG ACG CAG GCG CGC GAG     4995
Glu Gly Gly Ala Gly Asn Asp Trp Phe Gly Gln Thr Gln Ala Arg Glu
1325                1330                1335

CAT GAC GTG CTG CGC GGC GGA GAT GGG GTG GAT ACC GTC GAT TAC AGC     5043
His Asp Val Leu Arg Gly Gly Asp Gly Val Asp Thr Val Asp Tyr Ser
1340                1345                1350                1355

CAG ACC GGC GCG CAT GCC GGC ATT GCC GCG GGT CGC ATC GGG CTG GGC     5091
Gln Thr Gly Ala His Ala Gly Ile Ala Ala Gly Arg Ile Gly Leu Gly
            1360                1365                1370

ATC CTG GCT GAC CTG GGC GCC GGC CGC GTC GAC AAG CTG GGC GAG GCC     5139
Ile Leu Ala Asp Leu Gly Ala Gly Arg Val Asp Lys Leu Gly Glu Ala
        1375                1380                1385

GGC AGC AGC GCC TAC GAT ACG GTT TCC GGT ATC GAG AAC GTG GTG GGC     5187
Gly Ser Ser Ala Tyr Asp Thr Val Ser Gly Ile Glu Asn Val Val Gly
            1390                1395                1400

ACG GAA CTG GCC GAC CGC ATC ACG GGC GAT GCG CAG GCC AAC GTG CTG     5235
Thr Glu Leu Ala Asp Arg Ile Thr Gly Asp Ala Gln Ala Asn Val Leu
1405                1410                1415

CGC GGC GCG GGT GGC GCC GAC GTG CTT GCG GGC GGC GAG GGC GAC GAT     5283
Arg Gly Ala Gly Gly Ala Asp Val Leu Ala Gly Gly Glu Gly Asp Asp
1420                1425                1430                1435

GTG CTG CTG GGC GGC GAC GGC GAC GAC CAG CTG TCG GGC GAC GCC GGA     5331
Val Leu Leu Gly Gly Asp Gly Asp Asp Gln Leu Ser Gly Asp Ala Gly
                1440                1445                1450

CGC GAT CGC TTG TAC GGC GAA GCC GGT GAC GAC TGG TTC TTC CAG GAT     5379
Arg Asp Arg Leu Tyr Gly Glu Ala Gly Asp Asp Trp Phe Phe Gln Asp
            1455                1460                1465

GCC GCC AAT GCC GGC AAT CTG CTC GAC GGC GGC GAC GGC CGC GAT ACC     5427
Ala Ala Asn Ala Gly Asn Leu Leu Asp Gly Gly Asp Gly Arg Asp Thr
        1470                1475                1480
```

```
GTG GAT TTC AGC GGC CCG GGC CGG GGC CTC GAC GCC GGC GCA AAG GGC       5475
Val Asp Phe Ser Gly Pro Gly Arg Gly Leu Asp Ala Gly Ala Lys Gly
    1485                1490                1495

GTA TTC CTG AGC TTG GGC AAG GGG TTC GCC AGC CTG ATG GAC GAA CCC       5523
Val Phe Leu Ser Leu Gly Lys Gly Phe Ala Ser Leu Met Asp Glu Pro
1500                1505                1510                1515

GAA ACC AGC AAC GTG TTG CGC AAT ATC GAG AAC GCC GTG GGC AGC GCG       5571
Glu Thr Ser Asn Val Leu Arg Asn Ile Glu Asn Ala Val Gly Ser Ala
                1520                1525                1530

CGT GAT GAC GTG CTG ATC GGC GAC GCA GGC GCC AAC GTC CTC AAT GGC       5619
Arg Asp Asp Val Leu Ile Gly Asp Ala Gly Ala Asn Val Leu Asn Gly
            1535                1540                1545

CTG GCG GGC AAC GAC GTG CTG TCC GGC GGC GCT GGC GAC GAT GTG CTG       5667
Leu Ala Gly Asn Asp Val Leu Ser Gly Gly Ala Gly Asp Asp Val Leu
        1550                1555                1560

CTG GGC GAC GAG GGC TCG GAC CTG CTC AGC GGC GAT GCG GGC AAC GAC       5715
Leu Gly Asp Glu Gly Ser Asp Leu Leu Ser Gly Asp Ala Gly Asn Asp
    1565                1570                1575

GAT CTG TTC GGC GGG CAG GGC GAT GAT ACT TAT CTG TTC GGG GTC GGG       5763
Asp Leu Phe Gly Gly Gln Gly Asp Asp Thr Tyr Leu Phe Gly Val Gly
1580                1585                1590                1595

TAC GGG CAC GAC ACG ATC TAC GAA TCG GGC GGC GGC CAT GAC ACC ATC       5811
Tyr Gly His Asp Thr Ile Tyr Glu Ser Gly Gly Gly His Asp Thr Ile
                1600                1605                1610

CGC ATC AAC GCG GGG GCG GAC CAG CTG TGG TTC GCG CGC CAG GGC AAC       5859
Arg Ile Asn Ala Gly Ala Asp Gln Leu Trp Phe Ala Arg Gln Gly Asn
            1615                1620                1625

GAC CTG GAG ATC CGC ATT CTC GGC ACC GAC GAT GCA CTT ACC GTG CAC       5907
Asp Leu Glu Ile Arg Ile Leu Gly Thr Asp Asp Ala Leu Thr Val His
        1630                1635                1640

GAC TGG TAT CGC GAC GCC GAT CAC CGG GTG GAA ATC ATC CAT GCC GCC       5955
Asp Trp Tyr Arg Asp Ala Asp His Arg Val Glu Ile Ile His Ala Ala
    1645                1650                1655

AAC CAG GCG GTA GAC CAG GCA GGC ATC GAA AAG CTG GTC GAG GCA ATG       6003
Asn Gln Ala Val Asp Gln Ala Gly Ile Glu Lys Leu Val Glu Ala Met
1660                1665                1670                1675

GCG CAG TAT CCG GAC CCC GGC GCG GCG GCG GCT GCC CCG CCG GCG GCG       6051
Ala Gln Tyr Pro Asp Pro Gly Ala Ala Ala Ala Ala Pro Pro Ala Ala
                1680                1685                1690

CGC GTG CCG GAC ACG CTG ATG CAG TCC CTG GCT GTC AAC TGG CGC            6096
Arg Val Pro Asp Thr Leu Met Gln Ser Leu Ala Val Asn Trp Arg
            1695                1700                1705

TGAAGCGCCG TGAATCACGG CCCGCCTGCC TCGCGCGGCG GCGCCGTCTC TTTGCGTTCT      6156

TCTCCGAGGT ATTTCCCATC ATGACGTCGC CCGTGGCGCA ATGCGCCAGC GTGCCCGATT      6216

CCGGGTTGCT CTGCCTGGTC ATGCTGGCTC GCTATCACGG ATTGGCAGCC GATCCCGAGC      6276

AGTTGCGGCA TGAGTTCGCC GAGCAGGCAT TCTGTAGCGA AACGATACAG CCTGGCGGCG      6336

CGCCGGGTCG GCCTGAAAGT GCGGCGGCAC CGACCCGCGC CGGCGCGGCT GCCACGCGCG      6396

CCGCTGCCGG CCATCGCGCT GGACCGGCAG GGCGGCTACT TTGTT                     6441
```

(2) INFORMATION FOR SEQ ID NO: 2:

(i) SEQUENCE CHARACTERISTICS:
        (A) LENGTH: 1706 amino acids
        (B) TYPE: amino acid
        (C) STRANDEDNESS: single
        (D) TOPOLOGY: linear (ii) MOLECULE TYPE: Protein (xi) SEQUENCE DESCRIPTION: SEQ ID NO: 2:

```
Met Gln Gln Ser His Gln Ala Gly Tyr Ala Asn Ala Asp Arg Glu
 1               5                  10                  15

Ser Gly Ile Pro Ala Ala Val Leu Asp Gly Ile Lys Ala Val Ala Lys
             20                  25                  30

Glu Lys Asn Ala Thr Leu Met Phe Arg Leu Val Asn Pro His Ser Thr
         35                  40                  45

Ser Leu Ile Ala Glu Gly Val Ala Thr Lys Gly Leu Gly Val His Ala
     50                  55                  60

Lys Ser Ser Asp Trp Gly Leu Gln Ala Gly Tyr Ile Pro Val Asn Pro
 65                  70                  75                  80

Asn Leu Ser Lys Leu Phe Gly Arg Ala Pro Glu Val Ile Ala Arg Ala
                 85                  90                  95

Asp Asn Asp Val Asn Ser Ser Leu Ala His Gly His Thr Ala Val Asp
             100                 105                 110

Leu Thr Leu Ser Lys Glu Arg Leu Asp Tyr Leu Arg Gln Ala Gly Leu
         115                 120                 125

Val Thr Gly Met Ala Asp Gly Val Val Ala Ser Asn His Ala Gly Tyr
     130                 135                 140

Glu Gln Phe Glu Phe Arg Val Lys Glu Thr Ser Asp Gly Arg Tyr Ala
145                 150                 155                 160

Val Gln Tyr Arg Arg Lys Gly Gly Asp Asp Phe Glu Ala Val Lys Val
                 165                 170                 175

Ile Gly Asn Ala Ala Gly Ile Pro Leu Thr Ala Asp Ile Asp Met Phe
             180                 185                 190

Ala Ile Met Pro His Leu Ser Asn Phe Arg Asp Ser Ala Arg Ser Ser
         195                 200                 205

Val Thr Ser Gly Asp Ser Val Thr Asp Tyr Leu Ala Arg Thr Arg Arg
     210                 215                 220

Ala Ala Ser Glu Ala Thr Gly Gly Leu Asp Arg Glu Arg Ile Asp Leu
225                 230                 235                 240

Leu Trp Lys Ile Ala Arg Ala Gly Ala Arg Ser Ala Val Gly Thr Glu
                 245                 250                 255

Ala Arg Arg Gln Phe Arg Tyr Asp Gly Asp Met Asn Ile Gly Val Ile
             260                 265                 270

Thr Asp Phe Glu Leu Glu Val Arg Asn Ala Leu Asn Arg Arg Ala His
         275                 280                 285

Ala Val Gly Ala Gln Asp Val Val Gln His Gly Thr Glu Gln Asn Asn
     290                 295                 300

Pro Phe Pro Glu Ala Asp Glu Lys Ile Phe Val Val Ser Ala Thr Gly
305                 310                 315                 320

Glu Ser Gln Met Leu Thr Arg Gly Gln Leu Lys Glu Tyr Ile Gly Gln
                 325                 330                 335

Gln Arg Gly Glu Gly Tyr Val Phe Tyr Glu Asn Arg Ala Tyr Gly Val
             340                 345                 350

Ala Gly Lys Ser Leu Phe Asp Gly Leu Gly Ala Ala Pro Gly Val
         355                 360                 365

Pro Ser Gly Arg Ser Lys Phe Ser Pro Asp Val Leu Glu Thr Val Pro
     370                 375                 380

Ala Ser Pro Gly Leu Arg Arg Pro Ser Leu Gly Ala Val Glu Arg Gln
385                 390                 395                 400

Asp Ser Gly Tyr Asp Ser Leu Asp Gly Val Gly Ser Arg Ser Phe Ser
```

-continued

```
                405                 410                 415
Leu Gly Glu Val Ser Asp Met Ala Ala Val Ala Ala Glu Leu Glu
            420                 425                 430
Met Thr Arg Gln Val Leu His Ala Gly Ala Arg Gln Asp Asp Ala Glu
            435                 440                 445
Pro Gly Val Ser Gly Ala Ser Ala His Trp Gly Gln Arg Ala Leu Gln
            450                 455                 460
Gly Ala Gln Ala Val Ala Ala Gln Arg Leu Val His Ala Ile Ala
465                 470                 475                 480
Leu Met Thr Gln Phe Gly Arg Ala Gly Ser Thr Asn Thr Pro Gln Glu
            485                 490                 495
Ala Ala Ser Leu Ser Ala Ala Val Phe Gly Leu Gly Glu Ala Ser Ser
            500                 505                 510
Ala Val Ala Glu Thr Val Ser Gly Phe Phe Arg Gly Ser Ser Arg Trp
            515                 520                 525
Ala Gly Gly Phe Gly Val Ala Gly Gly Ala Met Ala Leu Gly Gly Gly
            530                 535                 540
Ile Ala Ala Ala Val Gly Ala Gly Met Ser Leu Thr Asp Asp Ala Pro
545                 550                 555                 560
Ala Gly Gln Lys Ala Ala Gly Ala Glu Ile Ala Leu Gln Leu Thr
            565                 570                 575
Gly Gly Thr Val Glu Leu Ala Ser Ser Ile Ala Leu Ala Leu Ala Ala
            580                 585                 590
Ala Arg Gly Val Thr Ser Gly Leu Gln Val Ala Gly Ala Ser Ala Gly
            595                 600                 605
Ala Ala Ala Gly Ala Leu Ala Ala Leu Ser Pro Met Glu Ile Tyr
            610                 615                 620
Gly Leu Val Gln Gln Ser His Tyr Ala Asp Gln Leu Asp Lys Leu Ala
625                 630                 635                 640
Gln Glu Ser Ser Ala Tyr Gly Tyr Glu Gly Asp Ala Leu Leu Ala Gln
            645                 650                 655
Leu Tyr Arg Asp Lys Thr Ala Ala Glu Gly Ala Val Ala Gly Val Ser
            660                 665                 670
Ala Val Leu Ser Thr Val Gly Ala Ala Val Ser Ile Ala Ala Ala Ala
            675                 680                 685
Ser Val Val Gly Ala Pro Val Ala Val Thr Ser Leu Leu Thr Gly
            690                 695                 700
Ala Leu Asn Gly Ile Leu Arg Gly Val Gln Gln Pro Ile Ile Glu Lys
705                 710                 715                 720
Leu Ala Asn Asp Tyr Ala Arg Lys Ile Asp Glu Leu Gly Gly Pro Gln
            725                 730                 735
Ala Tyr Phe Glu Lys Asn Leu Gln Ala Arg His Glu Gln Leu Ala Asn
            740                 745                 750
Ser Asp Gly Leu Arg Lys Met Leu Ala Asp Leu Gln Ala Gly Trp Asn
            755                 760                 765
Ala Ser Ser Val Ile Gly Val Gln Thr Thr Glu Ile Ser Lys Ser Ala
            770                 775                 780
Leu Glu Leu Ala Ala Ile Thr Gly Asn Ala Asp Asn Leu Lys Ser Val
785                 790                 795                 800
Asp Val Phe Val Asp Arg Phe Val Gln Gly Glu Arg Val Ala Gly Gln
            805                 810                 815
Pro Val Val Leu Asp Val Ala Ala Gly Gly Ile Asp Ile Ala Ser Arg
            820                 825                 830
```

-continued

```
Lys Gly Glu Arg Pro Ala Leu Thr Phe Ile Thr Pro Leu Ala Ala Pro
    835                 840                 845

Gly Glu Glu Gln Arg Arg Thr Lys Thr Gly Lys Ser Glu Phe Thr
850                 855                 860

Thr Phe Val Glu Ile Val Gly Lys Gln Asp Arg Trp Arg Ile Arg Asp
865                 870                 875                 880

Gly Ala Ala Asp Thr Thr Ile Asp Leu Ala Lys Val Val Ser Gln Leu
                885                 890                 895

Val Asp Ala Asn Gly Val Leu Lys His Ser Ile Lys Leu Asp Val Ile
                900                 905                 910

Gly Gly Asp Gly Asp Val Val Leu Ala Asn Ala Ser Arg Ile His
    915                 920                 925

Tyr Asp Gly Gly Ala Gly Thr Asn Thr Val Ser Tyr Ala Ala Leu Gly
    930                 935                 940

Arg Gln Asp Ser Ile Thr Val Ser Ala Asp Gly Glu Arg Phe Asn Val
945                 950                 955                 960

Arg Lys Gln Leu Asn Asn Ala Asn Val Tyr Arg Glu Gly Val Ala Thr
                965                 970                 975

Gln Thr Thr Ala Tyr Gly Lys Arg Thr Glu Asn Val Gln Tyr Arg His
                980                 985                 990

Val Glu Leu Ala Arg Val Gly Gln Val Val Glu Val Asp Thr Leu Glu
                995                 1000                1005

His Val Gln His Ile Ile Gly Gly Ala Gly Asn Asp Ser Ile Thr Gly
    1010                1015                1020

Asn Ala His Asp Asn Phe Leu Ala Gly Gly Ser Gly Asp Asp Arg Leu
1025                1030                1035                1040

Asp Gly Gly Ala Gly Asn Asp Thr Leu Val Gly Gly Glu Gly Gln Asn
                1045                1050                1055

Thr Val Ile Gly Gly Ala Gly Asp Asp Val Phe Leu Gln Asp Leu Gly
                1060                1065                1070

Val Trp Ser Asn Gln Leu Asp Gly Gly Ala Gly Val Asp Thr Val Lys
    1075                1080                1085

Tyr Asn Val His Gln Pro Ser Glu Glu Arg Leu Glu Arg Met Gly Asp
    1090                1095                1100

Thr Gly Ile His Ala Asp Leu Gln Lys Gly Thr Val Glu Lys Trp Pro
1105                1110                1115                1120

Ala Leu Asn Leu Phe Ser Val Asp His Val Lys Asn Ile Glu Asn Leu
                1125                1130                1135

His Gly Ser Arg Leu Asn Asp Arg Ile Ala Gly Asp Asp Gln Asp Asn
                1140                1145                1150

Glu Leu Trp Gly His Asp Gly Asn Asp Thr Ile Arg Gly Arg Gly Gly
    1155                1160                1165

Asp Asp Ile Leu Arg Gly Gly Leu Gly Leu Asp Thr Leu Tyr Gly Glu
    1170                1175                1180

Asp Gly Asn Asp Ile Phe Leu Gln Asp Asp Glu Thr Val Ser Asp Asp
1185                1190                1195                1200

Ile Asp Gly Gly Ala Gly Leu Asp Thr Val Asp Tyr Ser Ala Met Ile
                1205                1210                1215

His Ala Gly Lys Ile Val Ala Pro His Glu Tyr Gly Phe Gly Ile Glu
                1220                1225                1230

Ala Asp Leu Ser Arg Glu Trp Val Arg Lys Ala Ser Ala Leu Gly Val
                1235                1240                1245
```

-continued

```
Asp Tyr Tyr Asp Asn Val Arg Asn Val Glu Asn Val Ile Gly Thr Ser
    1250                1255                1260
Met Lys Asp Val Leu Ile Gly Asp Ala Gln Ala Asn Thr Leu Met Gly
1265            1270                1275                1280
Gln Gly Gly Asp Asp Thr Val Arg Gly Asp Gly Asp Leu Leu
            1285                1290                1295
Phe Gly Gly Asp Gly Asn Asp Met Leu Tyr Gly Asp Ala Gly Asn Asp
            1300                1305                1310
Thr Leu Tyr Gly Gly Leu Gly Asp Asp Thr Leu Glu Gly Gly Ala Gly
            1315                1320                1325
Asn Asp Trp Phe Gly Gln Thr Gln Ala Arg Glu His Asp Val Leu Arg
    1330                1335                1340
Gly Gly Asp Gly Val Asp Thr Val Asp Tyr Ser Gln Thr Gly Ala His
1345            1350                1355                1360
Ala Gly Ile Ala Ala Gly Arg Ile Gly Leu Gly Ile Leu Ala Asp Leu
            1365                1370                1375
Gly Ala Gly Arg Val Asp Lys Leu Gly Glu Ala Gly Ser Ser Ala Tyr
            1380                1385                1390
Asp Thr Val Ser Gly Ile Glu Asn Val Val Gly Thr Glu Leu Ala Asp
            1395                1400                1405
Arg Ile Thr Gly Asp Ala Gln Ala Asn Val Leu Arg Gly Ala Gly Gly
    1410                1415                1420
Ala Asp Val Leu Ala Gly Gly Glu Gly Asp Asp Val Leu Leu Gly Gly
1425            1430                1435                1440
Asp Gly Asp Asp Gln Leu Ser Gly Asp Ala Gly Arg Asp Arg Leu Tyr
            1445                1450                1455
Gly Glu Ala Gly Asp Asp Trp Phe Phe Gln Asp Ala Ala Asn Ala Gly
            1460                1465                1470
Asn Leu Leu Asp Gly Gly Asp Gly Arg Asp Thr Val Asp Phe Ser Gly
    1475                1480                1485
Pro Gly Arg Gly Leu Asp Ala Gly Ala Lys Gly Val Phe Leu Ser Leu
    1490                1495                1500
Gly Lys Gly Phe Ala Ser Leu Met Asp Glu Pro Glu Thr Ser Asn Val
1505            1510                1515                1520
Leu Arg Asn Ile Glu Asn Ala Val Gly Ser Ala Arg Asp Asp Val Leu
            1525                1530                1535
Ile Gly Asp Ala Gly Ala Asn Val Leu Asn Gly Leu Ala Gly Asn Asp
            1540                1545                1550
Val Leu Ser Gly Gly Ala Gly Asp Asp Val Leu Leu Gly Asp Glu Gly
            1555                1560                1565
Ser Asp Leu Leu Ser Gly Asp Ala Gly Asn Asp Leu Phe Gly Gly
    1570                1575                1580
Gln Gly Asp Asp Thr Tyr Leu Phe Gly Val Gly Tyr Gly His Asp Thr
1585            1590                1595                1600
Ile Tyr Glu Ser Gly Gly Gly His Asp Thr Ile Arg Ile Asn Ala Gly
            1605                1610                1615
Ala Asp Gln Leu Trp Phe Ala Arg Gln Gly Asn Asp Leu Glu Ile Arg
    1620                1625                1630
Ile Leu Gly Thr Asp Asp Ala Leu Thr Val His Asp Trp Tyr Arg Asp
            1635                1640                1645
Ala Asp His Arg Val Glu Ile Ile His Ala Ala Asn Gln Ala Val Asp
    1650                1655                1660
Gln Ala Gly Ile Glu Lys Leu Val Glu Ala Met Ala Gln Tyr Pro Asp
```

-continued

```
         1665                1670                1675                1680
Pro Gly Ala Ala Ala Ala Pro Pro Ala Ala Arg Val Pro Asp Thr
                 1685                1690                1695
Leu Met Gln Ser Leu Ala Val Asn Trp Arg
        1700                1705
```

(2) INFORMATION FOR SEQ ID NO: 3:

(i) SEQUENCE CHARACTERISTICS:
        (A) LENGTH: 5118 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..5115
        (D) OTHER INFORMATION:/note= "AMINO ACID SEQUENCE
            CORRESPONDING TO THE NUCLEOTIDE SEQUENCE OF THE GENE
            CODING FOR THE B. Bronchiseptica AC-Hly"

(xi) SEQUENCE DESCRIPTION: SEQ ID NO: 3:

```
ATG CAG CAA TCG CAT CAG GCT GGT TAC GCA AAC GCC GCC GAC CGG GAG          48
Met Gln Gln Ser His Gln Ala Gly Tyr Ala Asn Ala Ala Asp Arg Glu
          1710                1715                1720

TCT GGC ATC CCC GCA GCC GTA CTC GAT GGC ATC AAG GCC GTG GCG AAG          96
Ser Gly Ile Pro Ala Ala Val Leu Asp Gly Ile Lys Ala Val Ala Lys
     1725                1730                1735

GAA AAA AAC GCC ACA TTG ATG TTC CGC CTG GTC AAC CCC CAT TCC ACC         144
Glu Lys Asn Ala Thr Leu Met Phe Arg Leu Val Asn Pro His Ser Thr
 1740                1745                1750

AGC CTG ATT GCC GAA GGG GTG GCC ACC AAA GGA TTG GGC GTG CAC GCC         192
Ser Leu Ile Ala Glu Gly Val Ala Thr Lys Gly Leu Gly Val His Ala
1755                1760                1765                1770

AAG TCG TCC GAT TGG GGG TTG CAG GCG GGC TAC ATT CCC GTC AAC CCG         240
Lys Ser Ser Asp Trp Gly Leu Gln Ala Gly Tyr Ile Pro Val Asn Pro
          1775                1780                1785

AAT CTT TCC AAA CTG TTC GGC CGT GCG CCC GAG GTG ATC GCG CGG GCC         288
Asn Leu Ser Lys Leu Phe Gly Arg Ala Pro Glu Val Ile Ala Arg Ala
     1790                1795                1800

GAC AAC GAC GTC AAC AGC AGC CTG GCG CAT GGC CAT ACC GCG GTC GAC         336
Asp Asn Asp Val Asn Ser Ser Leu Ala His Gly His Thr Ala Val Asp
 1805                1810                1815

CTG ACG CTG TCG AAA GAG CGG CTT GAC TAT CTG CGG CAA GCG GGC CTG         384
Leu Thr Leu Ser Lys Glu Arg Leu Asp Tyr Leu Arg Gln Ala Gly Leu
     1820                1825                1830

GTC ACC GGC ATG GCC GAT GGC GTG GTC GCG AGC AAC CAC GCA GGC TAC         432
Val Thr Gly Met Ala Asp Gly Val Val Ala Ser Asn His Ala Gly Tyr
1835                1840                1845                1850

GAG CAG TTC GAG TTT CGC GTG AAG GAA ACC TCG GAC GGG CGC TAT GCC         480
Glu Gln Phe Glu Phe Arg Val Lys Glu Thr Ser Asp Gly Arg Tyr Ala
          1855                1860                1865

GTG CAG TAT CGC CGC AAG GGC GGC GAC GAT TTC GAG GCG GTC AAG GTG         528
Val Gln Tyr Arg Arg Lys Gly Gly Asp Asp Phe Glu Ala Val Lys Val
     1870                1875                1880

ATC GGC AAT GCC GCC GGT ATT CCA CTG ACG GCG GAT ATC GAC ATG TTC         576
Ile Gly Asn Ala Ala Gly Ile Pro Leu Thr Ala Asp Ile Asp Met Phe
 1885                1890                1895

GCC ATC ATG CCG CAT CTG TCC AAC TTC CGC GAC TCG GCG CGC AGT TCG         624
Ala Ile Met Pro His Leu Ser Asn Phe Arg Asp Ser Ala Arg Ser Ser
     1900                1905                1910
```

-continued

```
GTG ACC AGC GGC GAT TCG GTG ACC GAT TAC CTG GCG CGC ACG CGG CGG      672
Val Thr Ser Gly Asp Ser Val Thr Asp Tyr Leu Ala Arg Thr Arg Arg
1915                1920                1925                1930

GCC GCC AGC GAG GCC ACG GGC GGC CTG GAT CGC GAA CGC ATC GAC TTG      720
Ala Ala Ser Glu Ala Thr Gly Gly Leu Asp Arg Glu Arg Ile Asp Leu
                1935                1940                1945

TTG TGG AAA ATC GCT CGC GCC GGC GCC CGT TCC GCA GTG GGC ACC GAG      768
Leu Trp Lys Ile Ala Arg Ala Gly Ala Arg Ser Ala Val Gly Thr Glu
            1950                1955                1960

GCG CGT CGC CAG TTC CGC TAC GAC GGC GAC ATG AAT ATC GGC GTG ATC      816
 Ala Arg Arg Gln Phe Arg Tyr Asp Gly Asp Met Asn Ile Gly Val Ile
        1965                1970                1975

ACC GAT TTC GAG CTG GAA GTG CGC AAT GCG CTG AAC AGG CGG GCG CAC      864
Thr Asp Phe Glu Leu Glu Val Arg Asn Ala Leu Asn Arg Arg Ala His
    1980                1985                1990

GCG GTC GGC AGG CAG GAC GTG GTC CAG CAT GGC ACT GAG CAG AAC AAT      912
Ala Val Gly Arg Gln Asp Val Val Gln His Gly Thr Glu Gln Asn Asn
1995                2000                2005                2010

CCT TTC CCG GAG GCA GAT GAG AAG ATT TTC GTC GTA TCG GCC ACC GGT      960
Pro Phe Pro Glu Ala Asp Glu Lys Ile Phe Val Val Ser Ala Thr Gly
                2015                2020                2025

GAA AGC CAG ATG CTC ACG CGC GGG CAA CTG AAG GAA TAC ATT GGC CAG     1008
 Glu Ser Gln Met Leu Thr Arg Gly Gln Leu Lys Glu Tyr Ile Gly Gln
            2030                2035                2040

CAG CGC GGC GAG GGC TAT GTC TTC TAC GAG AAC CGT GCG TAC GGC GTG     1056
Gln Arg Gly Glu Gly Tyr Val Phe Tyr Glu Asn Arg Ala Tyr Gly Val
        2045                2050                2055

GCG GGG AAA AGC CTG TTC GAC GAT GGG CTG GGA GCC GCG CCC GGC GTG     1104
Ala Gly Lys Ser Leu Phe Asp Asp Gly Leu Gly Ala Ala Pro Gly Val
    2060                2065                2070

CCG GGG CGA CGT TCG AAG TCC TCG CCG GAT GTA CTG GAA ACG GTG CCG     1152
Pro Gly Arg Arg Ser Lys Ser Ser Pro Asp Val Leu Glu Thr Val Pro
2075                2080                2085                2090

GCG TCA CCC GGA TTG CGG CGG CCG TCG CTG GGC GCA GTG GAA CGC CAG     1200
Ala Ser Pro Gly Leu Arg Arg Pro Ser Leu Gly Ala Val Glu Arg Gln
                2095                2100                2105

GAT TCC GGC TAT GAC AGC CTT GAT GGG GTG GGA TCG CGA TCG TTC TCG     1248
Asp Ser Gly Tyr Asp Ser Leu Asp Gly Val Gly Ser Arg Ser Phe Ser
            2110                2115                2120

TTG GGC GAG GTG TCC GAC ATG GCC GCC GTG GAA GCG GCG GAA CTG GAA     1296
Leu Gly Glu Val Ser Asp Met Ala Ala Val Glu Ala Ala Glu Leu Glu
        2125                2130                2135

ATG ACC CGG CAA GTC TTG CAC GCC GGG GCG CGG CAG GAC GAT GCC GAG     1344
Met Thr Arg Gln Val Leu His Ala Gly Ala Arg Gln Asp Asp Ala Glu
    2140                2145                2150

CCG GGC GTG AGC GGT GCG TCG GCG CAC TGG GGG CAG CGG GCG CTG CAG     1392
Pro Gly Val Ser Gly Ala Ser Ala His Trp Gly Gln Arg Ala Leu Gln
2155                2160                2165                2170

GGC GCC CAG GCG GTG GCG GCG GCG CAG CGG CTG GTT CAT GCC ATT GCC     1440
Gly Ala Gln Ala Val Ala Ala Ala Gln Arg Leu Val His Ala Ile Ala
                2175                2180                2185

CTG ATG ACG CAA TTC GGC CGG GCC GGT TCC ACC AAC ACG CCG CAG GAA     1488
Leu Met Thr Gln Phe Gly Arg Ala Gly Ser Thr Asn Thr Pro Gln Glu
            2190                2195                2200

GCG GCC TCG TTG TCG GCG GCC GTG TTC GGC TTG GGC GAG GCC AGC AGC     1536
Ala Ala Ser Leu Ser Ala Ala Val Phe Gly Leu Gly Glu Ala Ser Ser
        2205                2210                2215

GCC GTG GCC GAA ACC GTG AGC GGT TTT TTC CGC GGG TCT TCG CGC TGG     1584
Ala Val Ala Glu Thr Val Ser Gly Phe Phe Arg Gly Ser Ser Arg Trp
```

```
                     2220                2225                2230
GCC GGC GGT TTC GGC GTG GCT GGC GGC GCG ATG GCG CTG GGA GGC GGC          1632
Ala Gly Gly Phe Gly Val Ala Gly Gly Ala Met Ala Leu Gly Gly Gly
        2235                2240                2245                2250

ATC GGC GCC GTT GGC GCC GGG ATG TCG TTG ACC GAT GAC GCG CCG GCC          1680
Ile Gly Ala Val Gly Ala Gly Met Ser Leu Thr Asp Asp Ala Pro Ala
                2255                2260                2265

GGA CAG AAG GCC GCC GCC GGC GCC GAG ATC GCG CTG CAG TTG ACA GGT          1728
Gly Gln Lys Ala Ala Ala Gly Ala Glu Ile Ala Leu Gln Leu Thr Gly
        2270                2275                2280

GGA ACG GTC GAG CTG GCT TCT TCC ATC GCG TTG GCG CTG GCC GCG GCG          1776
Gly Thr Val Glu Leu Ala Ser Ser Ile Ala Leu Ala Leu Ala Ala Ala
                2285                2290                2295

CGC GGC GTG ACC AGC GGC TTG CAG GTG GCG GGG GCG TCG GCC GGG GCG          1824
Arg Gly Val Thr Ser Gly Leu Gln Val Ala Gly Ala Ser Ala Gly Ala
        2300                2305                2310

GCT GCC GGC GCA TTG GCC GCG GCG CTC AGT CCC ATG GAG ATC TAC GGC          1872
Ala Ala Gly Ala Leu Ala Ala Ala Leu Ser Pro Met Glu Ile Tyr Gly
2315                2320                2325                2330

CTG GTG CAG CAA TCG CAC TAT GCG GAT CAG CTG GAC AAG CTG GCG CAG          1920
Leu Val Gln Gln Ser His Tyr Ala Asp Gln Leu Asp Lys Leu Ala Gln
                2335                2340                2345

GAA TCG AGC GCA TAC GGT TAC GAG GGC GAC GCC TTG CTG GCC CAG CTG          1968
Glu Ser Ser Ala Tyr Gly Tyr Glu Gly Asp Ala Leu Leu Ala Gln Leu
        2350                2355                2360

TAT CGC GAC AAG ACG GCC GCC GAG GGC GCC GTC GCC GGC GTC TCC GCC          2016
Tyr Arg Asp Lys Thr Ala Ala Glu Gly Ala Val Ala Gly Val Ser Ala
                2365                2370                2375

GTC CTG AGC ACG GTG GGG GCT GCG GTG TCG ATC GCC GCG GCG GCC AGC          2064
Val Leu Ser Thr Val Gly Ala Ala Val Ser Ile Ala Ala Ala Ala Ser
        2380                2385                2390

GTG GTA GGC GCC CCG GTG GCG GTG GTC ACT TCC TTG TTG ACC GGG GCT          2112
Val Val Gly Ala Pro Val Ala Val Val Thr Ser Leu Leu Thr Gly Ala
2395                2400                2405                2410

CTC AAC GGC ATC CTG CGC GGC GTG CAG CAG CCC ATC ATC GAA AAG CTG          2160
Leu Asn Gly Ile Leu Arg Gly Val Gln Gln Pro Ile Ile Glu Lys Leu
                2415                2420                2425

GCC AAT GAT TAC GCT CGC AAG ATC GAC GAG CTG GGC GGG CCG CAA GCG          2208
Ala Asn Asp Tyr Ala Arg Lys Ile Asp Glu Leu Gly Gly Pro Gln Ala
        2430                2435                2440

TAC TTC GAG AAA AAC CTG CAG GCG CGT CAC GAA CAA CTG GCC AAT TCG          2256
Tyr Phe Glu Lys Asn Leu Gln Ala Arg His Glu Gln Leu Ala Asn Ser
                2445                2450                2455

GAC GGC CTA CGG AAA ATG CTG GCC GAC CTG CAG GCC GGG TGG AAC GCC          2304
Asp Gly Leu Arg Lys Met Leu Ala Asp Leu Gln Ala Gly Trp Asn Ala
        2460                2465                2470

AGC AGC GTG ATC GGG GTG CAG ACG ACA GAG ATT TCC AAG TCG GCG CTC          2352
Ser Ser Val Ile Gly Val Gln Thr Thr Glu Ile Ser Lys Ser Ala Leu
2475                2480                2485                2490

GAA CTG GCC GCC ATT ACC GGC AAC GCG GAC AAC CTG AAA TCC GCC GAC          2400
Glu Leu Ala Ala Ile Thr Gly Asn Ala Asp Asn Leu Lys Ser Ala Asp
                2495                2500                2505

GTG TTC GTG GAC CGC TTC ATC CAG GGC GAG CGG GTG GCC GGC CAG CCG          2448
Val Phe Val Asp Arg Phe Ile Gln Gly Glu Arg Val Ala Gly Gln Pro
        2510                2515                2520

GTG GTA CTC GAC GTC GCC GCC GGC GGC ATC GAT ATC GCC AGC CGC AAG          2496
Val Val Leu Asp Val Ala Ala Gly Gly Ile Asp Ile Ala Ser Arg Lys
                2525                2530                2535

GGC GAG CGG CCG GCG CTG ACG TTC ATC ACG CCG CTG GCC GCG CCA GGA          2544
```

-continued

```
Gly Glu Arg Pro Ala Leu Thr Phe Ile Thr Pro Leu Ala Ala Pro Gly
        2540                2545                2550

GAA GAG CAG CGC CGG CGC ACG AAA ACG GGC AAG AGC GAA TTC ACC ACA        2592
 Glu Glu Gln Arg Arg Arg Thr Lys Thr Gly Lys Ser Glu Phe Thr Thr
2555                2560                2565                2570

TTC GTC GAG ATC GTG GGC AAG CAG GAC CGC TGG CGC ATC CGG GAC GGC        2640
 Phe Val Glu Ile Val Gly Lys Gln Asp Arg Trp Arg Ile Arg Asp Gly
            2575                2580                2585

GCG GCC GAC ACC ACC ATC GAT CTG GCC AAG GTG GTG TCG CAA CTG GTC        2688
 Ala Ala Asp Thr Thr Ile Asp Leu Ala Lys Val Val Ser Gln Leu Val
            2590                2595                2600

GAC GCC AAT GGC GTG CTC AAG CAC AGC ATC AAA CTG GAG GTG ATC GGC        2736
 Asp Ala Asn Gly Val Leu Lys His Ser Ile Lys Leu Glu Val Ile Gly
            2605                2610                2615

GGA GAT GGC GAT GAT GTC GTG CTT GCC AAT GCT TCG CGC ATC CAT TAC        2784
 Gly Asp Gly Asp Asp Val Val Leu Ala Asn Ala Ser Arg Ile His Tyr
        2620                2625                2630

GAC GGC GGC GCG GGA ACC AAC ACG GTC AGC TAT GCC GCC CTG GGC CGA        2832
 Asp Gly Gly Ala Gly Thr Asn Thr Val Ser Tyr Ala Ala Leu Gly Arg
2635                2640                2645                2650

CAG GAT TCC ATT ACC GTG TCC GCC GAC GGG GAA CGT TTC AAC GTG CGC        2880
 Gln Asp Ser Ile Thr Val Ser Ala Asp Gly Glu Arg Phe Asn Val Arg
            2655                2660                2665

AAG CAG TTG AAC AAC GCC AAC GTG TAT CGC GAA GGC GTG GCT ACC CAG        2928
 Lys Gln Leu Asn Asn Ala Asn Val Tyr Arg Glu Gly Val Ala Thr Gln
            2670                2675                2680

AAA ACC GCC TAC GGC AAG CGC ACG GAG AAT GTC CAA TAC CGC CAT GTC        2976
 Lys Thr Ala Tyr Gly Lys Arg Thr Glu Asn Val Gln Tyr Arg His Val
        2685                2690                2695

GAG CTG GCC CGT GTC GGG CAA CTG GTG GAG GTC GAC ACG CTC GAG CAT        3024
 Glu Leu Ala Arg Val Gly Gln Leu Val Glu Val Asp Thr Leu Glu His
        2700                2705                2710

GTG CAG CAC ATC ATC GGC GGG GCC GGC AAC GAT TCG ATC ACC GGC AAT        3072
 Val Gln His Ile Ile Gly Gly Ala Gly Asn Asp Ser Ile Thr Gly Asn
2715                2720                2725                2730

GCG CAC GAC AAC TTC CTG GCC GGC GGG GCG GGC GAC GAC AGG CTG GAT        3120
 Ala His Asp Asn Phe Leu Ala Gly Gly Ala Gly Asp Asp Arg Leu Asp
            2735                2740                2745

GGC GGC GCC GGC AAC GAC ACA CTG GTC GGC GGC GAG GGC CAC AAC ACG        3168
 Gly Gly Ala Gly Asn Asp Thr Leu Val Gly Gly Glu Gly His Asn Thr
            2750                2755                2760

GTC GTC GGC GGC GCT GGC GAC GAC GTA TTC CTG CAG GAC CTG GGG GTA        3216
 Val Val Gly Gly Ala Gly Asp Asp Val Phe Leu Gln Asp Leu Gly Val
            2765                2770                2775

TGG AGC AAC CAG CTC GAT GGC GGC GCG GGC GTC GAT ACC GTG AAG TAC        3264
 Trp Ser Asn Gln Leu Asp Gly Gly Ala Gly Val Asp Thr Val Lys Tyr
        2780                2785                2790

AAC GTG CAC CAG CCT TCC GAG GAA CGC CTC GAA CGC ATG GGC GAC ACG        3312
 Asn Val His Gln Pro Ser Glu Glu Arg Leu Glu Arg Met Gly Asp Thr
2795                2800                2805                2810

GGC ATC CAT GCC GAT CTT CAA AAG GGC ACG GTC GAG AAG TGG CCG GCC        3360
 Gly Ile His Ala Asp Leu Gln Lys Gly Thr Val Glu Lys Trp Pro Ala
            2815                2820                2825

CTG AAC CTG TTC AGC GTC GAC CAT GTC AAG AAT ATC GAG AAT CTG CAC        3408
 Leu Asn Leu Phe Ser Val Asp His Val Lys Asn Ile Glu Asn Leu His
            2830                2835                2840

GGC TCC AGC CTG AAC GAC AGC ATC GCC GGC GAC GAC CGG GAC AAC GAG        3456
 Gly Ser Ser Leu Asn Asp Ser Ile Ala Gly Asp Asp Arg Asp Asn Glu
            2845                2850                2855
```

-continued

| | | |
|---|---|---|
| CTC TGG GGC GAC GAT GGC AAC GAC ACG ATA CAC GGC CGG GGC GGC GAC<br>Leu Trp Gly Asp Asp Gly Asn Asp Thr Ile His Gly Arg Gly Gly Asp<br>     2860                             2865                        2870 | 3504 |

GAT ATC CTG CGC GGC GGC CTG GGC CTG GAC ACG CTG TAT GGC GAG GAC  3552
Asp Ile Leu Arg Gly Gly Leu Gly Leu Asp Thr Leu Tyr Gly Glu Asp
2875                2880                2885                2890

GGC AAC GAC ATC TTC CTG CAG GAC GAC GAG ACC GTC AGC GAT GAC ATC  3600
Gly Asn Asp Ile Phe Leu Gln Asp Asp Glu Thr Val Ser Asp Asp Ile
         2895                2900                2905

GAC GGT GGC GCG GGA CTG GAC ACC GTC GAC TAT TCC GCC ATG ATC CAT  3648
Asp Gly Gly Ala Gly Leu Asp Thr Val Asp Tyr Ser Ala Met Ile His
     2910                2915                2920

GCA GGC AAG ATC GTT GCG CCG CAT GAA TAC GGC TTC GGG ATC GAG GCG  3696
Ala Gly Lys Ile Val Ala Pro His Glu Tyr Gly Phe Gly Ile Glu Ala
 2925                2930                2935

GAC CTG TCC GAA GGG TGG GTG CGC AAG GCG GCC CGG CGC GGC ATG GAC  3744
Asp Leu Ser Glu Gly Trp Val Arg Lys Ala Ala Arg Arg Gly Met Asp
2940                2945                2950

TAC TAC GAC AGT GTC CGC AGT GTC GAA AAC GTC ATC GGC ACG AGC ATG  3792
Tyr Tyr Asp Ser Val Arg Ser Val Glu Asn Val Ile Gly Thr Ser Met
2955                2960                2965                2970

AAG GAT GTG CTC ATC GGC GAC GCG CAA GCC AAT ACC CTG ATG GGC CAG  3840
Lys Asp Val Leu Ile Gly Asp Ala Gln Ala Asn Thr Leu Met Gly Gln
         2975                2980                2985

GGC GGC GAC GAT ACC GTG CGC GGC GGC GAC GGC GAT GAT CTG CTG TTC  3888
Gly Gly Asp Asp Thr Val Arg Gly Gly Asp Gly Asp Asp Leu Leu Phe
     2990                2995                3000

GGC GGC GAC GGC AAC GAC ATG CTG TAT GGA GAC GCC GGC AAC GAC ACC  3936
Gly Gly Asp Gly Asn Asp Met Leu Tyr Gly Asp Ala Gly Asn Asp Thr
 3005                3010                3015

CTC TAC GGA GGG CTG GGC GAC GAT ACC CTT GAA GGC GGC GCG GGC AAC  3984
Leu Tyr Gly Gly Leu Gly Asp Asp Thr Leu Glu Gly Gly Ala Gly Asn
3020                3025                3030

GAT TGG TTC GGC CAG ACG CCG GCG CGC GAG CAT GAC GTG CTG CGC GGC  4032
Asp Trp Phe Gly Gln Thr Pro Ala Arg Glu His Asp Val Leu Arg Gly
3035                3040                3045                3050

GGG GCT GGG GTG GAT ACC GTG GAT TAC AGC CAG GCG GGC GCG CAT GCC  4080
Gly Ala Gly Val Asp Thr Val Asp Tyr Ser Gln Ala Gly Ala His Ala
         3055                3060                3065

GGC GTT GCC ACG GGT CGC ATC GGG CTG GGT ATT CTG GCG GAC CTG GGC  4128
Gly Val Ala Thr Gly Arg Ile Gly Leu Gly Ile Leu Ala Asp Leu Gly
     3070                3075                3080

GCC GGC CGC GTC GAC AAG CTG GGC GAG GCC GGC AGC AGC GCC TAC GAT  4176
Ala Gly Arg Val Asp Lys Leu Gly Glu Ala Gly Ser Ser Ala Tyr Asp
 3085                3090                3095

ACG GTT TCC GGC ATC GAA AAT GTG GTG GGC ACG GAA CTG GCC GAC CGC  4224
Thr Val Ser Gly Ile Glu Asn Val Val Gly Thr Glu Leu Ala Asp Arg
3100                3105                3110

ATC ACG GGC GAT GCG CAG GCC AAC GTA CTG CGC GGC GCG GGT GGC GCC  4272
Ile Thr Gly Asp Ala Gln Ala Asn Val Leu Arg Gly Ala Gly Gly Ala
3115                3120                3125                3130

GAC GTG CTT GCG GGC GGC GAG GGC GAC GAT GTG CTG CTG GGC GGC GAC  4320
Asp Val Leu Ala Gly Gly Glu Gly Asp Asp Val Leu Leu Gly Gly Asp
         3135                3140                3145

GGC GAC GAC CAG CTG TCG GGC GAC GCC GGA CGC GAC CGC TTG TAC GGC  4368
Gly Asp Asp Gln Leu Ser Gly Asp Ala Gly Arg Asp Arg Leu Tyr Gly
     3150                3155                3160

GAA GCC GGT GAC GAC TGG TTC TTC CAG GAT GCC GCC AAT GCC GGC AAT  4416
Glu Ala Gly Asp Asp Trp Phe Phe Gln Asp Ala Ala Asn Ala Gly Asn
 3165                3170                3175

```
CTG CTC GAC GGT GGT GAC GGC AAC GAT ACC GTG GAT TTC AGC GGC CCG        4464
Leu Leu Asp Gly Gly Asp Gly Asn Asp Thr Val Asp Phe Ser Gly Pro
        3180            3185            3190

GGC CGG GGC CTC GAC GCC GGC GCA AAG GGC GTA TTC CTG AGC CTG GGC        4512
Gly Arg Gly Leu Asp Ala Gly Ala Lys Gly Val Phe Leu Ser Leu Gly
3195            3200            3205                    3210

AAG GGG TTC GCC AGC CTG ATG GAC GAA CCC GAA ACC AGC AAC GTG TTG        4560
Lys Gly Phe Ala Ser Leu Met Asp Glu Pro Glu Thr Ser Asn Val Leu
            3215            3220            3225

CGC CAT ATC GAG AAC GCC GTG GGC AGC GTG CGT GAT GAC GTG CTG ATC        4608
Arg His Ile Glu Asn Ala Val Gly Ser Val Arg Asp Asp Val Leu Ile
                3230            3235            3240

GGC GAC GCA GGC GCC AAC GTC CTC AAT GGC CTG GCG GGC AAC GAC GTG        4656
Gly Asp Ala Gly Ala Asn Val Leu Asn Gly Leu Ala Gly Asn Asp Val
            3245            3250            3255

CTG TCG GCG GCG CCG GCG GAC GAT GTG CTG CTG GGC GAC GAG GGC TCG        4704
Leu Ser Ala Ala Pro Ala Asp Asp Val Leu Leu Gly Asp Glu Gly Ser
        3260            3265            3270

GAC CTG CTC AGC GGC GAT GCG GGC AAC GAC GAT CTG TTC GGC GGG CAG        4752
Asp Leu Leu Ser Gly Asp Ala Gly Asn Asp Asp Leu Phe Gly Gly Gln
3275            3280            3285            3290

GGC GAT GAT ACC TAT CTG TTC GGG GCC GGG TAC GGA CAT GAC ACG ATC        4800
Gly Asp Asp Thr Tyr Leu Phe Gly Ala Gly Tyr Gly His Asp Thr Ile
            3295            3300            3305

TAC GAA TCG GGC GGC GGC CAT GAC ACC ATC CGT ATC AAC GCG GGG GCG        4848
Tyr Glu Ser Gly Gly Gly His Asp Thr Ile Arg Ile Asn Ala Gly Ala
        3310            3315            3320

GAC CAG CTG TGG TTT GCG CGC CAG GGC AAC GAC CTG GAG ATC CGC ATT        4896
Asp Gln Leu Trp Phe Ala Arg Gln Gly Asn Asp Leu Glu Ile Arg Ile
        3325            3330            3335

CTT GGC ACC GAC GAT GCA CTT ACC GTG CAC GAC TGG TAT CGC GAC GCC        4944
Leu Gly Thr Asp Asp Ala Leu Thr Val His Asp Trp Tyr Arg Asp Ala
        3340            3345            3350

GAT CAC CGG GTG GAA GCC ATC CAT GCC GCC AAC CAG GCC ATA GAC CCG        4992
Asp His Arg Val Glu Ala Ile His Ala Ala Asn Gln Ala Ile Asp Pro
3355            3360            3365            3370

GCC GGC ATC GAA AAG CTG GTC GAG GCA ATG GCG CAG TAC CCG GAC CCC        5040
Ala Gly Ile Glu Lys Leu Val Glu Ala Met Ala Gln Tyr Pro Asp Pro
            3375            3380            3385

GGC GCG GCG GCG GCT GCC CCG CCG GCG GCG CGC GTG CCG GAC ACG CTG        5088
Gly Ala Ala Ala Ala Ala Pro Pro Ala Ala Arg Val Pro Asp Thr Leu
        3390            3395            3400

ATG CAG TCC CTG GCT GTC AAC TGG CGC TGA                                5118
Met Gln Ser Leu Ala Val Asn Trp Arg
        3405            3410
```

(2) INFORMATION FOR SEQ ID NO: 4:

(i) SEQUENCE CHARACTERISTICS:
        (A) LENGTH: 1705 amino acids
        (B) TYPE: amino acid
        (C) STRANDEDNESS: single
        (D) TOPOLOGY: linear (ii) MOLECULE TYPE: Protein (xi) SEQUENCE DESCRIPTION: SEQ ID NO: 4:

```
Met Gln Gln Ser His Gln Ala Gly Tyr Ala Asn Ala Ala Asp Arg Glu
1               5                   10                  15

Ser Gly Ile Pro Ala Ala Val Leu Asp Gly Ile Lys Ala Val Ala Lys
            20                  25                  30
```

```
Glu Lys Asn Ala Thr Leu Met Phe Arg Leu Val Asn Pro His Ser Thr
         35                  40                  45

Ser Leu Ile Ala Glu Gly Val Ala Thr Lys Gly Leu Gly Val His Ala
     50                  55                  60

Lys Ser Ser Asp Trp Gly Leu Gln Ala Gly Tyr Ile Pro Val Asn Pro
 65                  70                  75                  80

Asn Leu Ser Lys Leu Phe Gly Arg Ala Pro Glu Val Ile Ala Arg Ala
                 85                  90                  95

Asp Asn Asp Val Asn Ser Ser Leu Ala His Gly His Thr Ala Val Asp
            100                 105                 110

Leu Thr Leu Ser Lys Glu Arg Leu Asp Tyr Leu Arg Gln Ala Gly Leu
        115                 120                 125

Val Thr Gly Met Ala Asp Gly Val Val Ala Ser Asn His Ala Gly Tyr
    130                 135                 140

Glu Gln Phe Glu Phe Arg Val Lys Glu Thr Ser Asp Gly Arg Tyr Ala
145                 150                 155                 160

Val Gln Tyr Arg Arg Lys Gly Gly Asp Phe Glu Ala Val Lys Val
                165                 170                 175

Ile Gly Asn Ala Ala Gly Ile Pro Leu Thr Ala Asp Ile Asp Met Phe
            180                 185                 190

Ala Ile Met Pro His Leu Ser Asn Phe Arg Asp Ser Ala Arg Ser Ser
        195                 200                 205

Val Thr Ser Gly Asp Ser Val Thr Asp Tyr Leu Ala Arg Thr Arg Arg
    210                 215                 220

Ala Ala Ser Glu Ala Thr Gly Gly Leu Asp Arg Glu Arg Ile Asp Leu
225                 230                 235                 240

Leu Trp Lys Ile Ala Arg Ala Gly Ala Arg Ser Ala Val Gly Thr Glu
                245                 250                 255

Ala Arg Arg Gln Phe Arg Tyr Asp Gly Asp Met Asn Ile Gly Val Ile
            260                 265                 270

Thr Asp Phe Glu Leu Glu Val Arg Asn Ala Leu Asn Arg Arg Ala His
        275                 280                 285

Ala Val Gly Arg Gln Asp Val Val Gln His Gly Thr Glu Gln Asn Asn
    290                 295                 300

Pro Phe Pro Glu Ala Asp Glu Lys Ile Phe Val Val Ser Ala Thr Gly
305                 310                 315                 320

Glu Ser Gln Met Leu Thr Arg Gly Gln Leu Lys Glu Tyr Ile Gly Gln
                325                 330                 335

Gln Arg Gly Glu Gly Tyr Val Phe Tyr Glu Asn Arg Ala Tyr Gly Val
            340                 345                 350

Ala Gly Lys Ser Leu Phe Asp Asp Gly Leu Gly Ala Ala Pro Gly Val
        355                 360                 365

Pro Gly Arg Arg Ser Lys Ser Ser Pro Asp Val Leu Glu Thr Val Pro
    370                 375                 380

Ala Ser Pro Gly Leu Arg Arg Pro Ser Leu Gly Ala Val Glu Arg Gln
385                 390                 395                 400

Asp Ser Gly Tyr Asp Ser Leu Asp Gly Val Gly Ser Arg Ser Phe Ser
                405                 410                 415

Leu Gly Glu Val Ser Asp Met Ala Ala Val Glu Ala Ala Glu Leu Glu
            420                 425                 430

Met Thr Arg Gln Val Leu His Ala Gly Ala Arg Gln Asp Asp Ala Glu
        435                 440                 445
```

-continued

```
Pro Gly Val Ser Gly Ala Ser Ala His Trp Gly Gln Arg Ala Leu Gln
    450                 455                 460
Gly Ala Gln Ala Val Ala Ala Gln Arg Leu Val His Ala Ile Ala
465                 470                 475                 480
Leu Met Thr Gln Phe Gly Arg Ala Gly Ser Thr Asn Thr Pro Gln Glu
                485                 490                 495
Ala Ala Ser Leu Ser Ala Ala Val Phe Gly Leu Gly Glu Ala Ser Ser
            500                 505                 510
Ala Val Ala Glu Thr Val Ser Gly Phe Phe Arg Gly Ser Ser Arg Trp
        515                 520                 525
Ala Gly Gly Phe Gly Val Ala Gly Gly Ala Met Ala Leu Gly Gly Gly
    530                 535                 540
Ile Gly Ala Val Gly Ala Gly Met Ser Leu Thr Asp Asp Ala Pro Ala
545                 550                 555                 560
Gly Gln Lys Ala Ala Ala Gly Ala Glu Ile Ala Leu Gln Leu Thr Gly
                565                 570                 575
Gly Thr Val Glu Leu Ala Ser Ser Ile Ala Leu Ala Leu Ala Ala Ala
            580                 585                 590
Arg Gly Val Thr Ser Gly Leu Gln Val Ala Gly Ala Ser Ala Gly Ala
        595                 600                 605
Ala Ala Gly Ala Leu Ala Ala Ala Leu Ser Pro Met Glu Ile Tyr Gly
    610                 615                 620
Leu Val Gln Gln Ser His Tyr Ala Asp Gln Leu Asp Lys Leu Ala Gln
625                 630                 635                 640
Glu Ser Ser Ala Tyr Gly Tyr Glu Gly Asp Ala Leu Leu Ala Gln Leu
                645                 650                 655
Tyr Arg Asp Lys Thr Ala Ala Glu Gly Ala Val Ala Gly Val Ser Ala
            660                 665                 670
Val Leu Ser Thr Val Gly Ala Ala Val Ser Ile Ala Ala Ala Ala Ser
        675                 680                 685
Val Val Gly Ala Pro Val Ala Val Thr Ser Leu Leu Thr Gly Ala
    690                 695                 700
Leu Asn Gly Ile Leu Arg Gly Val Gln Gln Pro Ile Ile Glu Lys Leu
705                 710                 715                 720
Ala Asn Asp Tyr Ala Arg Lys Ile Asp Glu Leu Gly Gly Pro Gln Ala
                725                 730                 735
Tyr Phe Glu Lys Asn Leu Gln Ala Arg His Glu Gln Leu Ala Asn Ser
            740                 745                 750
Asp Gly Leu Arg Lys Met Leu Ala Asp Leu Gln Ala Gly Trp Asn Ala
        755                 760                 765
Ser Ser Val Ile Gly Val Gln Thr Thr Glu Ile Ser Lys Ser Ala Leu
    770                 775                 780
Glu Leu Ala Ala Ile Thr Gly Asn Ala Asp Asn Leu Lys Ser Ala Asp
785                 790                 795                 800
Val Phe Val Asp Arg Phe Ile Gln Gly Glu Arg Val Ala Gly Gln Pro
                805                 810                 815
Val Val Leu Asp Val Ala Ala Gly Gly Ile Asp Ile Ala Ser Arg Lys
            820                 825                 830
Gly Glu Arg Pro Ala Leu Thr Phe Ile Thr Pro Leu Ala Ala Pro Gly
        835                 840                 845
Glu Glu Gln Arg Arg Arg Thr Lys Thr Gly Lys Ser Glu Phe Thr Thr
    850                 855                 860
Phe Val Glu Ile Val Gly Lys Gln Asp Arg Trp Arg Ile Arg Asp Gly
```

```
                865                 870                 875                 880
Ala Ala Asp Thr Thr Ile Asp Leu Ala Lys Val Val Ser Gln Leu Val
                    885                 890                 895
Asp Ala Asn Gly Val Leu Lys His Ser Ile Lys Leu Glu Val Ile Gly
                900                 905                 910
Gly Asp Gly Asp Val Val Leu Ala Asn Ala Ser Arg Ile His Tyr
            915                 920                 925
Asp Gly Gly Ala Gly Thr Asn Thr Val Ser Tyr Ala Ala Leu Gly Arg
            930                 935                 940
Gln Asp Ser Ile Thr Val Ser Ala Asp Gly Glu Arg Phe Asn Val Arg
945                 950                 955                 960
Lys Gln Leu Asn Asn Ala Asn Val Tyr Arg Glu Gly Val Ala Thr Gln
                965                 970                 975
Lys Thr Ala Tyr Gly Lys Arg Thr Glu Asn Val Gln Tyr Arg His Val
                980                 985                 990
Glu Leu Ala Arg Val Gly Gln Leu Val Glu Val Asp Thr Leu Glu His
                995                 1000                1005
Val Gln His Ile Ile Gly Gly Ala Gly Asn Asp Ser Ile Thr Gly Asn
    1010                1015                1020
Ala His Asp Asn Phe Leu Ala Gly Gly Ala Gly Asp Arg Leu Asp
1025                1030                1035                1040
Gly Gly Ala Gly Asn Asp Thr Leu Val Gly Gly Glu Gly His Asn Thr
                1045                1050                1055
Val Val Gly Gly Ala Gly Asp Val Phe Leu Gln Asp Leu Gly Val
    1060                1065                1070
Trp Ser Asn Gln Leu Asp Gly Gly Ala Gly Val Asp Thr Val Lys Tyr
        1075                1080                1085
Asn Val His Gln Pro Ser Glu Glu Arg Leu Glu Arg Met Gly Asp Thr
    1090                1095                1100
Gly Ile His Ala Asp Leu Gln Lys Gly Thr Val Glu Lys Trp Pro Ala
1105                1110                1115                1120
Leu Asn Leu Phe Ser Val Asp His Val Lys Asn Ile Glu Asn Leu His
                1125                1130                1135
Gly Ser Ser Leu Asn Asp Ser Ile Ala Gly Asp Asp Arg Asp Asn Glu
                1140                1145                1150
Leu Trp Gly Asp Asp Gly Asn Asp Thr Ile His Gly Arg Gly Gly Asp
            1155                1160                1165
Asp Ile Leu Arg Gly Gly Leu Gly Leu Asp Thr Leu Tyr Gly Glu Asp
        1170                1175                1180
Gly Asn Asp Ile Phe Leu Gln Asp Asp Glu Thr Val Ser Asp Ile
1185                1190                1195                1200
Asp Gly Gly Ala Gly Leu Asp Thr Val Asp Tyr Ser Ala Met Ile His
                1205                1210                1215
Ala Gly Lys Ile Val Ala Pro His Glu Tyr Gly Phe Gly Ile Glu Ala
                1220                1225                1230
Asp Leu Ser Glu Gly Trp Val Arg Lys Ala Ala Arg Arg Gly Met Asp
                1235                1240                1245
Tyr Tyr Asp Ser Val Arg Ser Val Glu Asn Val Ile Gly Thr Ser Met
        1250                1255                1260
Lys Asp Val Leu Ile Gly Asp Ala Gln Ala Asn Thr Leu Met Gly Gln
1265                1270                1275                1280
Gly Gly Asp Asp Thr Val Arg Gly Gly Asp Gly Asp Asp Leu Leu Phe
                1285                1290                1295
```

```
Gly Gly Asp Gly Asn Asp Met Leu Tyr Gly Asp Ala Gly Asn Asp Thr
            1300                1305                1310
Leu Tyr Gly Gly Leu Gly Asp Asp Thr Leu Glu Gly Gly Ala Gly Asn
        1315                1320                1325
Asp Trp Phe Gly Gln Thr Pro Ala Arg Glu His Asp Val Leu Arg Gly
        1330                1335                1340
Gly Ala Gly Val Asp Thr Val Asp Tyr Ser Gln Ala Gly Ala His Ala
1345                1350                1355                1360
Gly Val Ala Thr Gly Arg Ile Gly Leu Gly Ile Leu Ala Asp Leu Gly
            1365                1370                1375
Ala Gly Arg Val Asp Lys Leu Gly Glu Ala Gly Ser Ser Ala Tyr Asp
            1380                1385                1390
Thr Val Ser Gly Ile Glu Asn Val Val Gly Thr Glu Leu Ala Asp Arg
            1395                1400                1405
Ile Thr Gly Asp Ala Gln Ala Asn Val Leu Arg Gly Ala Gly Gly Ala
            1410                1415                1420
Asp Val Leu Ala Gly Gly Glu Gly Asp Val Leu Leu Gly Gly Asp
1425                1430                1435                1440
Gly Asp Asp Gln Leu Ser Gly Asp Ala Gly Arg Asp Arg Leu Tyr Gly
            1445                1450                1455
Glu Ala Gly Asp Asp Trp Phe Phe Gln Asp Ala Ala Asn Ala Gly Asn
            1460                1465                1470
Leu Leu Asp Gly Gly Asp Gly Asn Asp Thr Val Asp Phe Ser Gly Pro
            1475                1480                1485
Gly Arg Gly Leu Asp Ala Gly Ala Lys Gly Val Phe Leu Ser Leu Gly
            1490                1495                1500
Lys Gly Phe Ala Ser Leu Met Asp Glu Pro Glu Thr Ser Asn Val Leu
1505                1510                1515                1520
Arg His Ile Glu Asn Ala Val Gly Ser Val Arg Asp Asp Val Leu Ile
            1525                1530                1535
Gly Asp Ala Gly Ala Asn Val Leu Asn Gly Leu Ala Gly Asn Asp Val
            1540                1545                1550
Leu Ser Ala Ala Pro Ala Asp Asp Val Leu Leu Gly Asp Glu Gly Ser
            1555                1560                1565
Asp Leu Leu Ser Gly Asp Ala Gly Asn Asp Asp Leu Phe Gly Gly Gln
            1570                1575                1580
Gly Asp Asp Thr Tyr Leu Phe Gly Ala Gly Tyr Gly His Asp Thr Ile
1585                1590                1595                1600
Tyr Glu Ser Gly Gly Gly His Asp Thr Ile Arg Ile Asn Ala Gly Ala
            1605                1610                1615
Asp Gln Leu Trp Phe Ala Arg Gln Gly Asn Asp Leu Glu Ile Arg Ile
            1620                1625                1630
Leu Gly Thr Asp Asp Ala Leu Thr Val His Asp Trp Tyr Arg Asp Ala
            1635                1640                1645
Asp His Arg Val Glu Ala Ile His Ala Ala Asn Gln Ala Ile Asp Pro
            1650                1655                1660
Ala Gly Ile Glu Lys Leu Val Glu Ala Met Ala Gln Tyr Pro Asp Pro
1665                1670                1675                1680
Gly Ala Ala Ala Ala Ala Pro Pro Ala Ala Arg Val Pro Asp Thr Leu
            1685                1690                1695
Met Gln Ser Leu Ala Val Asn Trp Arg
            1700                1705
```

PROTECTIVE EPITOPES OF ADENYL CYCLASE-HAEMOLYSIN (AC-HLY), THEIR APPLICATION TO THE TREATMENT OR TO THE PREVENTION OF BORDETELLA INFECTIONS

This is a division of application Ser. No. 08/669,785, filed Jun. 27, 1996, which is incorporated herein by reference.

BACKGROUND OF THE INVENTION

The present application relates to amino acid sequences comprising epitopes of adenyl cyclase-haemolysin from Bordetella. Adenyl cyclase-haemolysin (AC-Hly) is one of the toxins participating in the Bordetella infectious syndrome. AC-Hly is a bifunctional protein having an adenyl cyclase activity and a haemolytic activity. It is secreted by the bacterium. Its structural gene has been cloned and sequenced (Glaser P. et al., 1988, Molec. Microb. 2, 19–20). It is the case that this protein is part of the family of toxins termed "RTX" for "repeats in toxins" and exhibits homologies with haemolysin from Escherichia coli and Actinobacillus pleuropneumoniae, and the leucotoxins from Pasteurella haemolytica and Actinobacillus actinomycetemcomitans. This protein, like PTX (pertussis toxin), is capable of penetrating into eucaryotic cells such as the macrophages, of being activated by calmodulin, of synthesizing large quantities of cAMP and of disrupting cellular functions (Coote J. 1992. FEMS Microbiol. Rev. 88:137–162).

The inventors have identified, within this sequence, various domains having the capacity to induce the formation of protective antibodies against an infection by Bordetella, in particular by B. pertussis and/or B. parapertussis and/or B. bronchiseptica.

The subject of the invention is therefore amino acid sequences capable of entering into the composition of immunogenic compositions or of protective vaccines against Bordetella infections as well as antibodies directed against these amino acid sequences, capable of being used for example in immunotherapy. Immunotherapy or serotherapy is especially applicable in children, where appropriate in infants infected with B. pertussis, B. parapertussis or B. bronchiseptica. The invention proposes applications in human medicine or in veterinary medicine.

The subject of the present invention is an amino acid sequence derived from the polypeptide sequence of adenyl cyclase-haemolysin (AC-Hly), characterized in that it is capable of inducing the formation of protective antibodies against an infection by B. pertussis and/or B. parapertussis and/or B. bronchiseptica, and in that it is chosen from the following chains:

a) a sequence comprising the chain of amino acids situated approximately between position 910, preferably 913, and the last C-terminal amino acid of the polypeptide sequence of AC-Hly from B. pertussis (SEQ ID NO:2) or of a sequence corresponding to the preceding one in B. parapertussis or in B. bronchiseptica (SEQ ID NO:4), the said sequence comprising a modification by addition of a fatty acid between amino acids 980 approximately and 985 approximately, preferably at the level of amino acid 983;

b) sequence comprising a chain of 6 to 500 amino acids comprising amino acids 385 to 400 of the polypeptide sequence of AC-Hly from B. pertussis (SEQ ID NO:2) or of a sequence corresponding to the preceding one in B. parapertussis or in B. bronchiseptica (SEQ ID NO: 4);

c) a sequence comprising the chains of amino acids defined above in a) and b), the said chains being either contiguous, or combined via the chain of amino acids naturally present between the chains defined above in a) and b) within the AC-Hly from B. pertussis, B. parapertussis or B. bronchiseptica, or combined via an antigenic sequence derived from a protein different from AC-Hly, the amino acid sequence obtained having a three-dimensional conformation identical or analogous to that of the corresponding polypeptide sequence of AC-Hly from B. pertussis, B. parapertussis or B. bronchiseptica.

The expression "amino acid sequence derived from the polypeptide sequence of AC-Hly" is understood to mean, within the framework of the invention, a sequence whose amino acids are identical, by their nature or by their linkage, to those of the polypeptide sequence of AC-Hly or are, for some of them, substituted, deleted or added, in a manner such that the immunological properties of AC-Hly are conserved. In particular, such a sequence, derived from the polypeptide sequence of AC-Hly is recognized by antibodies formed in a patient infected with Bordetella, especially with B. pertussis, B. parapertussis or B. bronchiseptica.

It will be considered, within the framework of the present invention, that the structure or the conformation of AC-Hly is conserved, the amino acid sequence of the invention then having a structure identical or analogous to that of AC-Hly, when the said amino acid sequence is capable, after immunization of a patient or an animal, of inducing a protective immunity against Bordetella infections.

A sequence according to the invention can be obtained by proteolysis of AC-Hly purified from Bordetella. Preferably, this sequence is obtained by chemical synthesis or by genetic engineering techniques.

Thus, to produce an amino acid sequence according to the invention by genetic engineering, plasmids carrying fragments of the CyaA gene will be used.

By way of example, the chemical synthesis may be performed in automatic machines of the Applied Biosystem type. It is also possible to use the technique of Betsou F. et al., 1993, Infect. Immun., 61:3583–3589.

In this manner, it will be possible to prepare a peptide corresponding to the chain of amino acids 385 to 400, or even 385 to 500 of AC-Hly from B. pertussis or to the corresponding chain of AC-Hly from B. parapertussis or from B. bronchiseptica. The amino acid sequence (SEQ ID NO: 2) as well as the nucleotide sequence (SEQ ID NO: 1) of AC-Hly from B. pertussis has been described in Glaser et al, 1988, Molec. Microb. 2-19–30 and is represented in FIG. 5. The amino acid sequence (SEQ ID NO: 4) and the nucleotide sequence (SEQ ID NO: 3) of AC-Hly from B. bronchiseptica is represented in FIG. 6.

The amino acid sequence of AC-Hly from B. parapertussis and the nucleotide sequence encoding AC-Hly can be obtained by conventional techniques from the DNA from a strain of B. parapertussis, for example the strain No. 1 deposited at the CNCM on 2 Dec. 1994 under the No. I-1498.

When amino acid sequence according to the invention is produced by genetic engineering from the DNA of the CyaA genes from B. pertussis, B. parapertussis or B. bronchiseptica, and when it comprises the amino acid in position 983 of AC-Hly from B. pertussis (SEQ ID NO: 2) or a corresponding amino acid of AC-Hly from B. pertussis or B.

*bronchiseptica* (SEQ ID NO: 4), care will be taken to ensure that this sequence is produced in a cellular host also expressing the CyaC gene from the strains identified above. The expression of the CyaC gene allows the modification by addition of a fatty acid necessary to conserve in the amino acid sequence comprising residue 983. The addition of a fatty acid may, by way of example, be a palmitoylation.

Strains which can be used in order to have access to CyaA and CyaC genes are for example *B. pertussis* HAV deposited at the CNCM on 19 Oct. 1994 under the No. I-1485, *B. parapertussis* I-1498 and *B. bronchiseptica* 973S deposited at the CNCM on 12 May 1989 under the No. I-858.

Moreover, the nucleotide sequences encoding AC-Hly from *B. pertussis* and from *B. bronchiseptica* are presented in FIGS. 5 and 6 (SEQ ID NOS: 1 and 3) respectively.

The nucleotide sequence of the CyaC gene which activates the CyaA gene has been described in the publication of Barry E. M. et al. (Journal of Bacteriology, January 1991, p. 720–726).

An advantageous sequence within the framework of the present invention is the sequence corresponding to the regions termed modified region and repeat region of AC-Hly (see FIG. 1).

When an antigenic sequence which is heterologous in relation to the polypeptide sequence of AC-Hly is present, it may be a sequence of a bacterial, viral or parasitic pathogenic organism in particular, against which the formation of protective antibodies, for example, is sought.

The expression "protective antibodies against an infection by *B. pertussis* and/or *B. bronchiseptica*" is understood to mean antibodies which protect against the lethal and sublethal infections induced by these bacteria, that is to say which protect against the disease and the infection.

Advantageously, the amino acid sequences according to the invention, which are capable of inducing the formation of protective antibodies against the infections designated above, are associated with factors involved in the virulence of *Bordetella*, and are used for example in the form of polypeptide preparations or of bacterial extracts having the capacity to induce protection against persistence of the bacteria in the host.

An advantageous amino acid sequence within the framework of the invention is a sequence characterized in that it is in the form of a polypeptide having a three-dimensional conformation identical or analogous to that of the corresponding polypeptide sequence of AC-Hly from *B. pertussis* or from *B. parapertussis* or from *B. bronchiseptica*, in that it comprises the chain of amino acids situated between positions 900 approximately, in particular 910, and the last C-terminal amino acid approximately of the polypeptide sequence of AC-Hly from *B. pertussis* (SEQ ID NO: 2) or of a sequence corresponding to the preceding one in *B. parapertussis* or in *B. bronchiseptica* (SEQ ID NO: 4), the said sequence comprising, in addition, a modification by addition of a fatty acid between amino acids 980 approximately and 985 approximately, in particular at the level of amino acid 983.

This amino acid sequence comprises the modified region and the repeat region of AC-Hly.

Another preferred amino acid sequence according to the invention is a sequence characterized in that it is formed by the chain of amino acids between the amino acid in position 385 approximately and approximately the last C-terminal amino acid of the polypeptide sequence of AC-Hly from *B. pertussis* (SEQ ID NO: 2) or of a sequence corresponding to the preceding one in *B. parapertussis* or in *B. bronchiseptica* (SEQ ID NO: 4), the said sequence comprising a modification by addition of a fatty acid between amino acids 980 approximately and 985 approximately, preferably at the level of amino acid 983.

A subject of the invention is also an amino acid sequence entering within the scope of the definitions given above, formed by the chain of amino acids between the amino acid in position 385 approximately and the amino acid in position 400 approximately of the polypeptide sequence of AC-Hly from *B. pertussis* (SEQ. ID NO: 2) or of a sequence corresponding to the preceding one in *B. parapertussis* or in *B. bronchiseptica* (SEQ. ID NO: 4).

This amino acid sequence advantageously comprises an epitope capable of inducing the formation of protective antibodies against an infection by *Bordetella* of the *B. pertussis, B. parapertussis* and *B. bronchiseptica* types.

According to another embodiment of the invention, the amino acid sequence is characterized in that it is formed by the chain of amino acids between the amino acid in position 385 approximately and the amino acid in position 500 approximately of the polypeptide sequence of AC-Hly from *B. pertussis* (SEQ ID NO: 2) or of a sequence corresponding to the preceding one in *B. parapertussis* or in *B. bronchiseptica* (SEQ ID NO: 4).

Advantageously, this sequence comprising amino acids 385 to 400 or 385 to 500 is presented in a conformation identical or analogous to the conformation which it possesses in the AC-Hly protein from *Bordetella*.

The subject of the invention is also amino acid sequences obtained by deletion of polypeptide fragments from the sequence of AC-Hly from *Bordetella*, whether it is the sequence purified from the bacterium, and in particular from *B. pertussis, B. parapertussis* or *B. bronchiseptica* or whether it is a sequence obtained from a recombinant protein r-AC-Hly.

An amino acid sequence thus obtained is advantageously the sequence called ΔCla corresponding to the AC-Hly chain modified by deletion of an ΔCla fragment represented in FIG. 1, corresponding to the chain of amino acids 827 to 887 of the polypeptide sequence of AC-Hly from *B. pertussis* (SEQ ID NO: 2) or of a sequence corresponding to the preceding one in *B. parapertussis* or in *B. bronchiseptica* (SEQ ID NO: 4), the sequence obtained comprising a modification by addition of a fatty acid between amino acids 980 approximately and 985 approximately, preferably at the level of amino acid 983.

Another fragment may be deleted from the AC-Hly sequence in order to form an amino acid sequence according to the invention; this is the polypeptide fragment AH corresponding to the chain of amino acids 385 to 827 of the polypeptide sequence of AC-Hly from *B. pertussis* (SEQ ID NO: 2) or of a sequence corresponding to the preceding one in *B. parapertussis* or in *B. bronchiseptica* (SEQ ID NO: 4), the sequence obtained comprising a modification by addition of a fatty acid between amino acids 980 approximately and 985 approximately, preferably at the level of amino acid 983.

The subject of the invention is also the amino acid sequence forming the "repeat region" of AC-Hly from *Bordetella*, between the amino acid residues 1000 and 1600 approximately. The repeat region from *B. bronchiseptica* comprises one repeat less compared to the AC-Hly from *B. pertussis*. In this regard, the invention relates, for example, to the sequence comprising amino acids 1552 to 1592 of AC-Hly from *B. pertussis* (SEQ ID NO: 2).

The invention also relates to the nucleotide sequences encoding the amino acid sequences described above.

The genes CyaA, CyaB and partially CyaD from *B. bronchiseptica* were cloned into the plasmid pFBD2 harboured by *E. coli* K12XL1 and deposited at the CNCM on 21 Jun. 1995 under the No. I-1601.

The plasmid pFBD2 is obtained by insertion at the BamHI site of the 8 kb fragment from *B. bronchiseptica* carrying the genes CyaA, CyaB and partially CyaD.

The subject of the invention is moreover polypeptide compositions comprising sequences according to the invention originating from various types of *Bordetella*. For example, an advantageous polypeptide composition comprises a sequence defined above from *B. pertussis* or another sequence or several of these sequences from *B. parapertussis*.

Another polypeptide composition of the invention comprises, in addition, one or more sequences from *B. bronchiseptica*.

According to another embodiment of the invention, a polypeptide composition is characterized in that it comprises one or more sequences defined above from *B. parapertussis* and one or more sequences from *B. bronchiseptica*.

The subject of the invention is also immunogenic compositions characterized in that they comprise one or more sequences defined in the preceding pages.

Advantageously for protection against infection by *Bordetella* and in particular for protection against persistence of the bacteria in the host, an immunogenic composition comprising the amino acid sequences of the invention may be characterized in that it comprises, in addition, a bacterial extract containing the products of expression of the vrg genes from a strain of *Bordetella* chosen from *B. pertussis, B. parapertussis* or *B. bronchiseptica* or a portion of these expression products, sufficient to induce an immune response in a host to which the extract might be administered.

In addition to the presence of various adhesins and toxins, Bordetellae are characterized by regulation of the expression of the factors involved in their virulence. In other words, Bordetellae undergo phase variations and modulations.

Bordetellae, depending on their environment, can become "avirulent", that is to say incapable of inducing lethality, an inflammatory reaction and pulmonary lesions in the murine model of respiratory infection. They undergo either a phase modulation or a phase variation. The phase variation is observed at a frequency ranging from $10^{-3}$ to $10^{-6}$ and is practically reversible. It results in a stoppage of the expression of the toxins and adhesins described above and in the expression of other factors still not well characterized (change of the Phase I "virulent" bacteria to Phase IV "avirulent" bacteria). The phase I and phase IV bacteria have been described by Lacey B. 1960, J. Hyg, 58:57–93. The phase modulation, phenotypically similar to the phase variation, is completely reversible and results in a stoppage of the synthesis of the adhesins and toxins during environmental changes (composition of the culture medium, temperature and the like).

The phase variation and the phase modulation observed in *Bordetella* are under the control of two regulatory genes, bvg A and bvg S (Arico B et al., 1989, Proc. Natl. Acad. Sci. USA, 86:6671–6675).

The bvg S gene encodes a protein sensitive to the external conditions. This protein modulates, by phosphorylation, the activity of the protein encoded by the bvg A gene, which is, on the one hand, a positive activator of the transcription of the genes encoding the factors for virulence (vag genes for "vir activated genes") mentioned above (Uhl M. A. and Miller J, 1994, Proc. Natl. Acad. Sci. USA 91:1163–1167), and on the other hand a repressor of the transcription of certain genes (Beattie D. T. et al., J. of Bacteriology, Jan. 93, p. 159–527). The genes whose expression is repressed are called vrg genes for "vir repressed genes" and are yet poorly characterized. It has however been shown that the vrg 6 gene from *B. pertussis* encodes a protein having a role in the persistence of the bacterium in the host (Beatties D. et al., 1992, Infect. Imm. 60:571–577). In *B. bronchiseptica*, two proteins encoded by the vrg genes have been characterized: they are proteins of the flagella type (*B. bronchiseptica* phase I is an immotile bacterium which does not synthesize flagella but which synthesizes adhesins and toxins, and *B. bronchiseptica* phase IV is a motile bacterium which synthesizes flagella).

The presence, in the immunogenic composition, of a bacterial extract comprising the products of expression of the vrg genes would make it possible to enhance the humoral and/or cellular immune response obtained after infection in vaccinated subjects and would also contribute to the protection against the persistence of the bacterium.

The bacterial extract termed "vrg bacterial extract" which is in question above contains all the constituents of the external membrane of a phase IV bacterium, that is to say of a bacterium not expressing the vag genes, including the LPS endotoxin. This endotoxin may however be eliminated or detoxified.

This extract may be present in the form of a suspension.

The "vrg" bacterial extracts used to carry out the invention are preferably extracts termed "urea extracts".

A "urea extract" is composed of a mixture of proteins expressed at the surface of the bacterium and which are separated from the bacterium after incubation of the latter with 5 M urea. The "vrg" urea extract contains several proteins as yet not characterized, the flagella and the LPS.

The use of urea extracts allows the production of a vaccine which is cheaper compared with a vaccine which would be obtained from the proteins contained in the extracts, in purified form.

In addition, the inventors have observed that the urea extracts used may induce a T type cell immuno response (lymphoproliferation), thus behaving like the cellular vaccine used up until now.

On the contrary, exclusively acellular compositions are thought not to induce a T response, a reaction which nevertheless occurs in the event of infection.

The vrg urea extracts are respectively prepared from phase IV bacteria. Where appropriate, the phase IV bacteria are replaced with bacteria whose bvg S gene is mutated such that the bacteria express only the proteins encoded by the vrg genes.

The preparation of these extracts is described in detail in the experimental part.

Thus, the invention preferably relates to an immunogenic composition comprising both a vag urea extract from *B. pertussis* and a vrg urea extract from *B. pertussis*.

An appropriate *B. pertussis* strain for the preparation of these extracts is the HAV strain entering within the framework of the invention and deposited at the CNCM (Collection Nationale de Cultures de Microorganismes in Paris), on 19 Oct. 1994 under the No. I-1485. To prepare the vag urea extract, the HAV strain can be used directly since it is a phase I strain.

On the other hand, the vrg urea extract is obtained from a phase IV strain derived from the phase I strain for example by mutation of the bvg S gene from the bacterium or by culture of the said phase I strain in a medium containing only magnesium sulphate, so as to obtain the expression of the *B. pertussis* vrg genes alone.

In the same manner and where appropriate to improve the immune response in the host to which the immunogenic composition might be administered, the latter comprises, in addition, one or more adhesins or toxins from *B. pertussis, B. parapertussis* or *B. bronchiseptica*, chosen from FHA, AGGs or PRN and PTX or a portion of these proteins, sufficient to induce an immune response in a host to which the extract might be administered.

Advantageously, the amino acid sequences derived from the AC-Hly toxin and, where appropriate, the proteins expressed by the vrg genes are obtained from the HAV strain deposited at the CNCM under the No. I-1485.

Likewise, the amino acid sequences from *B. parapertussis* used within the framework of the invention are obtained from strain No. 1 deposited at the CNCM under the No. I-1498.

Moreover, the amino acid sequences from the *bronchiseptica* strain which are used within the framework of the invention may be obtained from the strain 9735 deposited at the CNCM under the No. I-858.

The references given above for the various *Bordetella* strains are indicated either to give access to the sequence of the proteins and where appropriate to reproduce this sequence by chemical synthesis, or to obtain the amino acid sequences of the invention by proteolysis of the proteins from *Bordetella*, or to give access to the DNA of the strains and thus to allow the production of the amino acid sequences of the invention by genetic engineering techniques.

The subject of the invention is also a vaccine composition comprising, as active ingredient, an immunogenic composition defined above, in combination with a pharmaceutically acceptable vehicle and, where appropriate, with an adjuvant.

The invention also relates to a process for the preparation of monoclonal antibodies recognizing the AC-Hly from *B. pertussis*, the AC-Hly from *B. parapertussis* and the AC-Hly from *B. bronchiseptica*, comprising the steps of:

immunizing an animal, for example a Balb/c mouse with a peptide comprising the sequence of amino acids 385 to 400 of AC-Hly from *B. pertussis* (SEQ ID NO: 2), the immunization being, where appropriate, carried out by means of repeated administrations of the peptide;

fusing the spleen cells of the immunized animal with myeloma cells to form a hybridoma;

culturing the hybridoma under conditions allowing the production of antibodies;

recovering the antibodies directed against the sequence of amino acids 385 to 400 of the AC-Hly from *B. pertussis*.

The process described above advantageously allows, by using for the immunization an antigen specific for the AC-Hly from *B. pertussis*, monoclonal antibodies to be obtained which recognize both the AC-Hly from *B. pertussis* and those from *B. parapertussis* and from *B. bronchiseptica*. In addition, such monoclonal antibodies advantageously have protective capacities in relation to the infection of a human or animal host by *Bordetella* of the *B. pertussis, B. parapertussis* and/or *B. bronchiseptica* type. Thus, the monoclonal antibodies obtained by using the process described above can be used for the treatment of patients or animals infected with one or more strains of *Bordetella* chosen from *B. pertussis, B. parapertussis* or *B. bronchiseptica*.

In general, the subject of the invention is monoclonal antibodies characterized in that they recognize the sequence of amino acids 385 to 400 of the AC-Hly from *B. pertussis*.

The invention relates, in this regard, to monoclonal antibodies which recognize an epitope comprising the sequence of amino acids 385–400 of the AC-Hly from *B. pertussis*, produced by the hybridoma B5–4 deposited at the CNCM on 19 Jun. 1996 under the No. I-1734.

Other advantageous monoclonal antibodies are produced against the sequence of the last 217 amino acids of the AC-Hly from *B. pertussis* (SEQ ID NO: 2) and are produced by the hybridoma E17-21 deposited at the CNCM on 19 Jun. 1996 under the No. I-1733.

The subject of the invention is also monoclonal antibodies directed against any of the amino acid sequences described above. Monoclonal antibodies directed specifically against the C-terminal sequence of the AC-Hly are among the advantageous antibodies of the invention. Special antibodies are for example directed against a sequence derived from the corresponding chain comprising the last 217 amino acids of the AC-Hly from *B. pertussis* (SEQ ID NO: 2), especially the amino acids 1488 to 1705 of the AC-Hly from *B. pertussis* (SEQ ID NO: 2) or the amino acids 1489 to 1706 of the AC-Hly from *B. bronchiseptica* (SEQ ID NO: 4). These monoclonal antibodies may be prepared by a process analogous to that which is described above for the monoclonal antibodies obtained against the epitope contained in the sequence of amino acids 385 to 400 approximately of the AC-Hly from *B. pertussis* (SEQ ID NO: 2).

The antibodies of the invention may be humanized, for example, by replacing the hypervariable part of a human immunoglobulin, having no antibody function, with a hypervariable region of a monoclonal immunoglobulin obtained by means of the technique described above.

Techniques which make it possible to humanize antibodies have for example been described by Waldmann T., June 1991, Science, vol. 252, p. 1657–1662; Winter G. et al., 1993, Immunology Today, vol. 14, No. 6, p. 243–246; Carter et al., May 1992, Proc. Natl. Acad. Sci. USA, vol. 89, p. 4285–4289; Singer et al., 1 Apr. 1993, Journal of Immunology, vol. 150, No. 7, p. 2844–2857.

The subject of the invention is also polyclonal sera as obtained by immunization of an animal with an amino acid sequence corresponding to the definitions given above and recovering the antibodies formed which are capable of recognizing the sequences used for the immunization.

Where appropriate, the immunization comprises the administration, with the amino acid sequences, of an adjuvant.

According to a specific embodiment of the invention, the immunization is carried out with one or more amino acid sequences and with an immunogenic composition comprising various antigens of AC-Hly.

The invention also relates to a pharmaceutical composition comprising, as active ingredient, monoclonal antibodies according to the invention.

These antibodies, in particular the antibodies directed against the sequence comprising the amino acids 385 to 400 and/or the antibodies directed against the C-terminal part of the AC-Hly protein, can be used as medicinal product in immuotherapy in a host infected with *B. pertussis* and/or *B. parapertussis* and/or *B. bronchiseptica*.

Use will be made for example of the monoclonal antibodies produced by the hydridoma B5-4, deposited on Jun. 19, 1996, under the provision of the Budapest Treaty at the National Collection of Cultures of Microorganisms (C.N.C.M.) in Paris, France, and assigned Accession No. I-1734 or by the hybridoma E17-21 deposited at the CNCM under the No. I-1733.

The antibodies according to the invention may also be used as means for analyzing the *Bordetella* strains collected. The monoclonal antibodies directed against the amino acid sequence 358 to 400 or against the C-terminal sequence of the AC-Hly protein are thus appropriate for the analysis of the *B. pertussis* strains.

Also entering within the framework of the invention is a process for the in vitro detection of an infection by a *Bordetella* especially by *B. pertussis, B. parapertussis* or *B. bronchiseptica*, characterized in that a sample of biological liquid from a patient or from an animal capable of being infected by *Bordetella* is brought into contact with monoclonal antibodies defined above or with a polyclonal serum defined above and in that an immunological reaction is detected between the said monoclonal or polyclonal antibodies and bacteria of the genus *Bordetella* when they are present in the sample.

The detection of infection with a bacterium of the *Bordetella* genus, especially by *B. pertussis, B. parapertussis* and *B. bronchiseptica*, may also be carried out on a sample of a biological fluid from a patient or from an animal by bringing the sample tested into contact with an amino acid sequence corresponding to the definitions above, followed by the detection of an immunological reaction between the said amino acid sequences and the antibodies present in the sample tested.

The invention also relates to a pharmaceutical composition comprising, as active ingredient, nucleotide sequences described above.

The use of the nucleotide sequences in pharmaceutical compositions may be implemented with reference to the technique described by Donnelly et al. (Nature Mèdecine, 1995, vol. 1. No. 6, p. 583–587).

BRIEF DESCRIPTION OF THE DRAWINGS

FIG. 1: Schematic representation of the truncated proteins of the AC-Hly used: the construction of the plasmids and the production of the corresponding truncated proteins has been described in previous publications from Sebo P. et al., 1991, Gene, 104:19–24 and Sebo P. et al., 1993, Mol. Microb. 9:999 1009. The numbers placed in the column "Mr" indicate the relative molecular masses of the toxins, calculated from their deduced amino acid sequences. The numbers which follow the symbol Δ in the name of the plasmid are the numbers for the first and the last amino acid of the parts deleted from the reading frame of cyaA. The numbers which follow the symbol ΔC represent the missing C-terminal residues. The cyaA alleles are coexpressed with the cyaC gene under the control of signals for initiation of transcription and of translation of the lacZ gene identical to that present in the plasmid pCACT3 (Betsou F. et al., 1993, Infect. Immun. 61:3583–3589). ΔC1307 was produced from pDIA5240 (pACTΔC1307) in the presence of the cyaC gene expressed in trans from a compatible plasmid pPS4C (Betsou F. et al., 1993, Infect. Immun. 61:3583–3589 and Sebo P. et al., 1991, Gene, 104:19–24).

FIG. 2: Characterization of *B. pertussis* and of the r-AC-Hly protein: 200 ng of purified *B. pertussis* and of r-AC-Hly were subjected to electrophoresis on an 8–25% SDS-PAGE gel and the proteins were stained with Coomassie blue (A) or transferred to a HYBOND C-Super membrane and incubated with mixed anti-r-AC-Hly sera from 20 mice, 22 days after the vaccination (B) or with monoclonal antibodies specific for the AC-Hly from *B. pertussis* (C) or a mixture of sera from infected children (infections confirmed by culture) (D) or a serum from mice infected with *B. pertussis* 18323 collected two weeks after the infection (E) or a serum from mice infected with *B. pertussis* collected two months after the infection (F). The immunodetection was performed with peroxidase-labelled rabbit anti-mouse antibodies. Line 1: *B. pertussis* AC-Hly; line 2: r-AC-Hly; line 3: ΔHR2; line 4: ΔH; line 5: ΔCla; line 6: ΔC217; line 7: ΔC1307; the numbers indicate the molecular weight markers.

FIG. 3: Inhibition of the adenylate cyclase (A), haemolytic (B) and cytotoxic (C) activities of the AC-Hly from *B. pertussis* by antisera directed against r-AC-Hly fragments obtained in various mice and by sera from mice and children infected with *B. pertussis*: the AC-Hly was incubated with various sera as described in the Materials and Methods part. The bars indicate the standard deviation (n=4).

FIG. 4: Protective activities of r-AC-Hly and of its truncated proteins. 3- to 4-week-old mice were immunized twice, at two week intervals, with 15 μg of r-AC-Hly (Δ-Δ), ΔCla (▲-▲), ΔC1307 (•-•), or ΔHR2 ([ ]-[ ]), ΔC217 (■-■), ΔH (□-□) or *B. pertussis* AC-Hly (○-○) adsorbed onto aluminium hydroxide, or with a buffer containing aluminium hydroxide alone as control (□-[ ]). They are infected via the intranasal route two weeks later with $10^5$ CFU of *B. pertussis* 18323. The curves show the standard geometric deviation (bars) for six mice per point.

FIG. 5: Nucelotide sequence of the gene encoding the AC-Hly from *B. pertussis* (SEQ. ID NO: 2) and the corresponding amino acid sequence (SEQ ID NO: 1).

FIG. 6: Nucelotide sequence of the gene encoding the AC-Hly from *B. bronchiseptica* (SEQ ID NO: 3) and the corresponding amino acid sequence (SEQ ID NO: 4).

EXAMPLES

Materials And Methods

Bacteria Strains, Plasmids and Growth Conditions:

The virulent strain *B. pertussis* 18323 (ATCC 9797) was cultured on a Bordet Gengou agar medium supplemented with 15% defibrinated sheep blood (BG) at 36° C. for 72 hours and again for 24 h. Subcultures in a liquid medium were performed in a Stainer-Scholte medium (Stainer D. W. and Scholte M. J., 1971, J. Gen. Microb., 63:211–220) for 20 h at 36° C. until an optical density at 650 nm of 1.0 is obtained ($OD_{620}$=1.0).

The plasmids used for the production of the recombinant protein r-AC-Hly and its truncated derivatives in *E. coli* have been described in the following publications: (Betsou F., P. Sebo and N. Guiso, 1993, CyaC-mediated activation is important not only for toxic but also for protective activities of *Bordetella pertussis* adenylate cyclase-haemolysin, Infect. Immun. 61:3583–3589; Iwaki M., Ullmann A. and P. Sebo, 1995, "Oligomerization of the adenylate cyclase toxin of *Bordetella pertussis*: Evidence from in vitro complementation of individually inactive mutants". Submitted; and Sebo P., P. Glaser, H. Sakamoto and A. Ullmann, 1991, High level synthesis of adenylate cyclase toxin of *Bordetella pertussis* in a reconstructed *Escherichia coli* system, Gene 104: 19–24.

The plasmids allow the production of the various proteins (FIG. 1) in the presence of the activating protein CyaC. *E. coli* XL-1 Blue strains (Stratagene) comprising the respective plasmids were cultured at 37° C. on a 2xYT medium containing 100 μg/l ampicillin at an optical density $OD_{600}$ of 0.5 to 0.7, and induced in order to obtain the production of AC-Hly by IPTG (1 mM) for four additional hours (Betsou F., P. Sebo, and N. Guiso, 1993, Infect. Immun. 61:3583–3589).

Tests of the Adenylate Cyclase, Haemolytic and Cytotoxic Activities

The adenylate cyclase activity was measured according to the procedure described by Ladant D., C. Brezin, I. Crenon, J. M. Alonso, and N. Guiso, (1987, *Bordetella pertussis* adenylate cyclase: purification, characterization and radio-immunoassay, J. Biol. Chem. 261:16264–16269). One unit (U) of adenylate cyclase activity corresponds to 1 nmol of cAMP formed per minute at 30° C., at pH 8.0. The haemolytic and cytotoxic activities of AC-Hly were determined at 37° C. using washed sheep erythrocytes (10⁹/ml) according to the description of Bellalou J., H. Sakamoto, D. Ladant, C. Geoffroy and A. Ullmann, (1990, Deletions affecting haemolytic and toxin activities of *Bordetella pertussis* adenylate cyclase, infect. Immun. 58: 3242–3247). The protein concentrations were determined by the method of Bradford (A rapid and sensitive method for the quantification of micrograms of protein, utilizing the principle of protein-dye binding. Anal. Biochem. 72:248–257).

Tests of Inhibition of Adenylate Cyclase

The purified AC-Hly from *B. pertussis* was incubated at 100 U/ml in 50 mM Tris-HCl at pH 7.6, with 0.2 mM $CaCl_2$ and 0.1 NP-40 with various sera diluted 100-fold for 18 to 20 h at 4° C.; the post-incubation adenylate cyclase activity (IA) of the samples was measured. The AC (adenylate cyclase) activity after incubation with the serum from mice immunized with aluminium hydroxide alone (CA) was taken as reference for 100% activity (in other words 0% inhibition).

The percentage inhibition of the AC activity was calculated as follows:

% inhibition=100%−(100%×IA/CA).

Tests of Inhibition of the Haemolytic Activity

One unit (U) of toxin and 5 µl of the various sera were mixed in 1 ml of 10 mM Tris-HCl at pH 8, with 2 mM $CaCl_2$, 150 mM NaCl and 1 µM bovine brain calmodulin and preincubated for 20 min. at 4° C. Washed sheep erythrocytes (10⁹) were added and the remaining haemolytic activity was determined after incubation for 3 h at room temperature. The unlysed erythrocytes were recovered in the form of a pellet after centrifugation at 2000 rpm and the optical density of the haemoglobin released (RH) into the supernatants was measured at 541 nm. The haemolytic activity of the toxin incubated with the serum of mice immunized with only aluminium hydroxide (CH) was taken as reference for 100% activity (0% inhibition). The sheep erythrocytes incubated without the toxin were used as control for nonspecific lysis. The percentage inhibition of the haemolytic activity was calculated as follows: % inhibition=100%−(100%×RH/CH).

Tests of Inhibition of the Cytotoxic Activity

One unit (U) of toxin and 5 µl of various sera were preincubated at 4° C. for 20 minutes in a total volume of 1 ml of 10 mM Tris-HCl at pH 8, with 2 mM $CaCl_2$, 150 mM NaCl, 5 mM glucose, 1 mg/ml BSA and 1 µM bovine brain calmodulin. Then 10⁹ washed sheep erythrocytes were added and the incubation was continued at 37° C. for 30 minutes. In order to stop the activity of the toxin, 50 µl of erythrocyte suspension were injected into 1 ml of 50 mM boiling sodium acetate at pH 5.2 and heated at 100° C. for 5 min. The quantity of cAMP formed in the lysed erythrocytes (IT) was determined by a standard ELISA method (Pradelles P. Grassi J. Chabardes D., Guiso N. 1989, Analytical Chemistry, 61:447–450). The toxin incubated at 4° C. was used as negative control of cytotoxicity. The activity of the toxin incubated with the serum of mice immunized with aluminium hydroxide alone (CT) was considered as being the 100% activity (0% inhibition). The percentage inhibition of the cytotoxic activity was calculated as being: % inhibition=100%−(100%×IT/CT).

Electrophoresis and Immunoblotting Methods

An SDS-PAGE electrophoresis was performed on an 8–25% ready-for-use polyacrylamide gel for the PhastSystem (Pharmacia) and the separated proteins were electrotransferred from the polyacrylamide gels to Hybond C-Super membranes (Amersham). After blocking, the membranes were incubated at a dilution of $10^{-3}$ with polyclonal sera at 4° C. overnight. The immunochemical detection was performed using horseradish peroxidase-labelled sheep anti-mouse immunoglobulins and an enhanced chemiluminescence system (ECL-Amersham).

Production and Purification of AC-Hly.

The AC-Hly from *B. pertussis*, the r-AC-Hly (recombinant AC-Hly) produced from *E. coli* and the various recombinant truncated proteins were extracted from bacteria with urea and purified on calmodulin affinity columns according to the method described by Guiso N., M. Szatanik and M. Rocandourt (1991, Protective activity of *Bordetella* adenylate cyclase against bacterial colonization. Microb. Pathog. 11:423–431). The enzymatic preparations were preserved in 8 M urea with 50 mM Tris-HCl at pH 8, with 0.2 mM $CaCl_2$, at −20° C. All the preparations were analysed in order to determine their degree of purity by SDS-polyacrylamide gel electrophoresis (SDS-PAGE).

Active Immunization

The purified preparations of r-AC-Hly and of the truncated proteins were adsorbed at 60 µg/ml on aluminium hydroxide (250 µg/ml). To carry out an active immunization, 3- to 4-week-old female Balb/c mice (CERJ, St Berthevin, France) were treated by subcutaneous injection of 15 µg of protein antigens twice, at two weeks interval. The controls received only buffer with aluminium hydroxide. The mice were then bled one week following the last injection, so as to allow access to the circulating antibodies present. Sublethal respiratory infection was achieved two weeks after the second immunization.

Intranasal Infection of the Mice

The *B. pertussis* strain was cultured on a Bordet Gengou BG medium for 48 h according to the preceding description and the bacteria were resuspended in 1% casamino acids. Sublethal quantities were administered by intranasal injections of 50 µl of the bacterial suspensions. The infected mice were sacrificed by cervical dislocation 1 hour after the exposure (at a time designated by "day 0") and on different days after day 0 (6 mice during each stage). The lungs were collected aseptically and homogenized in salt with a tissue grinder. Dilutions of the homogeneous lung preparations were sampled on a BG medium and colony forming units (cfu) were counted after 3 days of incubation at 36° C. All the experiments were performed at least twice and gave coherent results.

Preparation of the Immune Sera

To obtain the sera from the infected mice, 10 female Balb/c mice (4 weeks old) were infected intranasally with $2 \times 10^5$ virulent *B. pertussis* bacteria according to the technique described by Guiso N. Rocancourt, M. Szatanik and J. M. Alonso, (1989, *Bordetella* adenylate cyclase is a virulence associated factor and a protective antigen, Molec. Pathog. 7:373–380). The mice were bled 14 days after the infection or on different designated days following these 14 days.

The mouse polyclonal sera directed against the truncated derivatives of AC-Hly were collected one week after the second injection given to the mice with each of the antigens considered.

The serum of infected patients was prepared by mixing polyclonal immune sera from 10 selected nonvaccinated children infected with *B. pertussis*. These children were more than 8 months old, so as to exclude the presence of maternal antibodies in them, and less than 2 years old so as to be certain of their clinical history.

RESULTS

Immunological Properties of the r-AC-Hly Protein and of its Truncated Variants

It has been shown in the past that the modification of AC-Hly occurring through the CyaC protein from *B. pertussis* is essential for its protective activity (Betsou et al., CyaC-mediated activation is important not only for toxic but also for protective activities of *Bordetella pertussis* adenylate cyclase-haemolysin, Infect. Immun., 61:3583–3589). It was therefore important to determine if this modification itself contributed to the formation of the protective epitope in its linear form or if this modification induced a conformational modification in the toxin, a modification required for the presentation of the protective epitopes. Consequently, the immunological and protective properties of a number of truncated proteins were examined; the truncated proteins in question are schematically represented in FIG. 1.

Figure 2A:
Figure 2B:
Figure 2C:

These proteins were produced in *E. coli* in the presence of the CyaC protein using the plasmids pCACT or pDIA so as to allow acylation by CyaC by means of fatty acid chains, of the constructs containing the site of modification. As shown in FIG. 2A, the preparations purified from all the proteins contained a major polypeptide corresponding to the expected molecular weight. These proteins were checked by a Western Blot test in order to verify their recognition by various sera. As shown in FIG. 2B, the serum produced against the r-AC-Hly protein recognized the r-AC-Hly protein and also recognized the AC-Hly protein purified from *B. pertussis* as well as all the truncated forms derived from r-AC-Hly. In accordance with FIG. 2A, the purified polypeptide preparations comprising the total length of the protein, in other words the preparations of AC-Hly, r-AC-Hly and the truncated polypeptides ΔCla and ΔC217, also contained several fragments recognized by a polyclonal serum obtained against the purified protein r-AC-Hly (FIG. 2B). Monoclonal antibodies (FIG. 2) prepared specifically against the adenylate cyclase domain of AC-Hly also recognized these fragments of AC-Hly, ΔCla and ΔC217, showing that these fragments were proteolytic fragments truncated in the C-terminal part and containing the AC domain which copurified with AC-Hly on calmoduline-agarose. However, the monoclonal antibody did not recognize the proteins ΔH or ΔHR2 which lacked residues 385 to 828 and 1489 to 1706 respectively, but this antibody recognized the protein ΔC1307. Using these observations in particular, the inventors established that the region of the molecule located between amino acids 385 and 400 participated in the formation of an epitope.

Figure 2D:
Figure 2E:
Figure 2F:
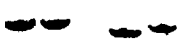

Quite remarkably and contrary to what could happen with the anti-r-AC-Hly serum, the sera obtained from infected children and used in the form of a mixture did not recognize the AC domain of AC-Hly (ΔC1307; line 7), and neither did they recognize the protein lacking the 217 terminal residues of AC-Hly (ΔC217; line 6) nor the protein containing the last 217 residues but lacking hydrophobic regions, which is modifed, and the major part of the repeat region of AC-Hly (ΔHR2, line 3). However, these human sera recognized the AC-Hly from *B. pertussis* and r-AC-Hly (FIG. 2D, lines 1 and 2) and the two truncated proteins possessing modified and repeat regions (last 900 residues) of AC-Hly (FIG. 2D, lines 4 and 5). An identical recognition pattern (FIG. 2F) was obtained with mouse serum infected with *B. pertussis* 18323 (reference strain) and collected rapidly after the infection (14 days). The sera collected long after the infection (35 days) recognized the C-terminal part of AC-Hly present in the protein ΔHR2 (FIG. 2F, line 3), whereas they continued not to recognize the AC domain (FIG. 2F, line 7) and the protein ΔC217 lacking only the last 217 residues (FIG. 2F, line 6). These results strongly suggest that the anti-AC-Hly antibodies synthesized after infection with *B. pertussis* are predominantly directed against the C-terminal region comprising the modification region and the repeat region of AC-Hly (last 900 residues). Furthermore, neither the protein ΔC217 lacking the last 217 residues of AC-Hly, nor the protein ΔHR2 which contained the last 217 residues were recognized by the immune and murine sera, suggesting that these polyclonal sera recognize a specific structure of the repeat region of AC-Hly, which structure is abolished by any of the two nonoverlapping deletions.

It is important to note that the sera from infected patients or mice recognized only the polypeptides stretching over the entire length of the protein (AC-Hly, r-AC-Hly, ΔCla and ΔH) but not their proteolytic fragments. The absence of recognition, by these sera, of the proteolysis products, which contain the AC domain and are cleaved in their C-terminal part (see above FIG. 2C) indicates, in addition, that the region of modification and the repeat region of AC-Hly (last 900 residues) must be intact to be recognized by these sera.

Figure 3A:
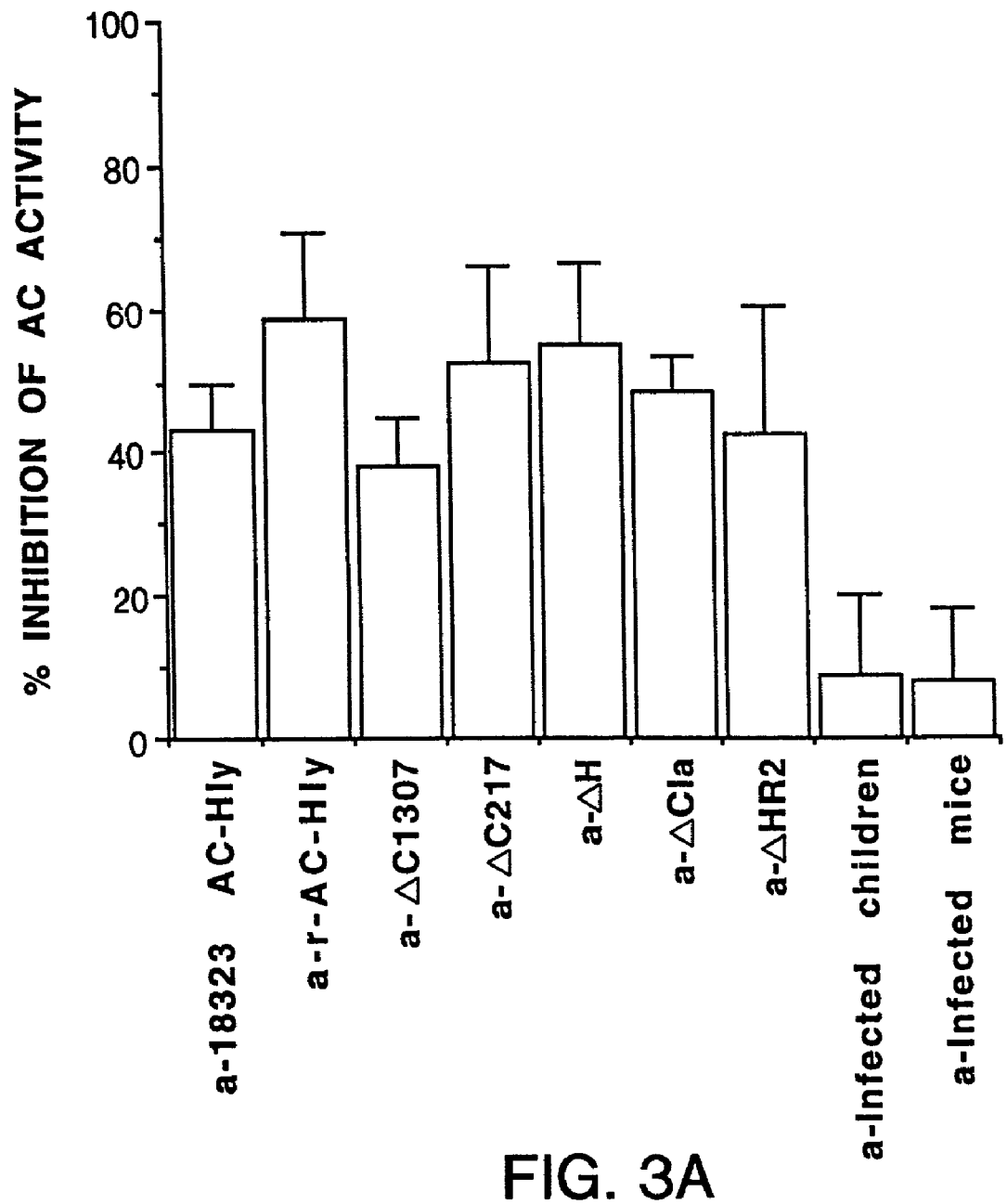
Figure 3B:
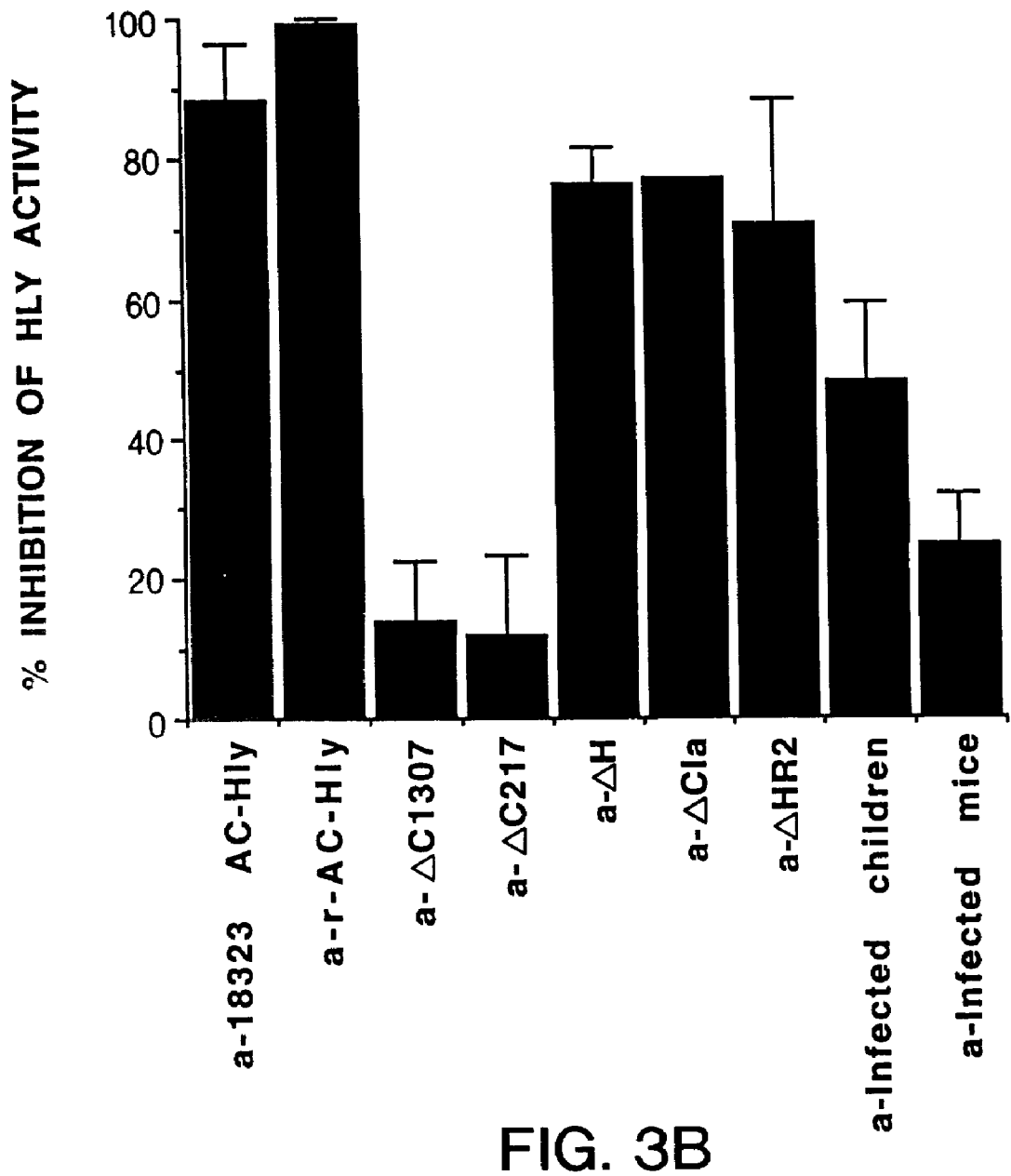
Figure 3C:
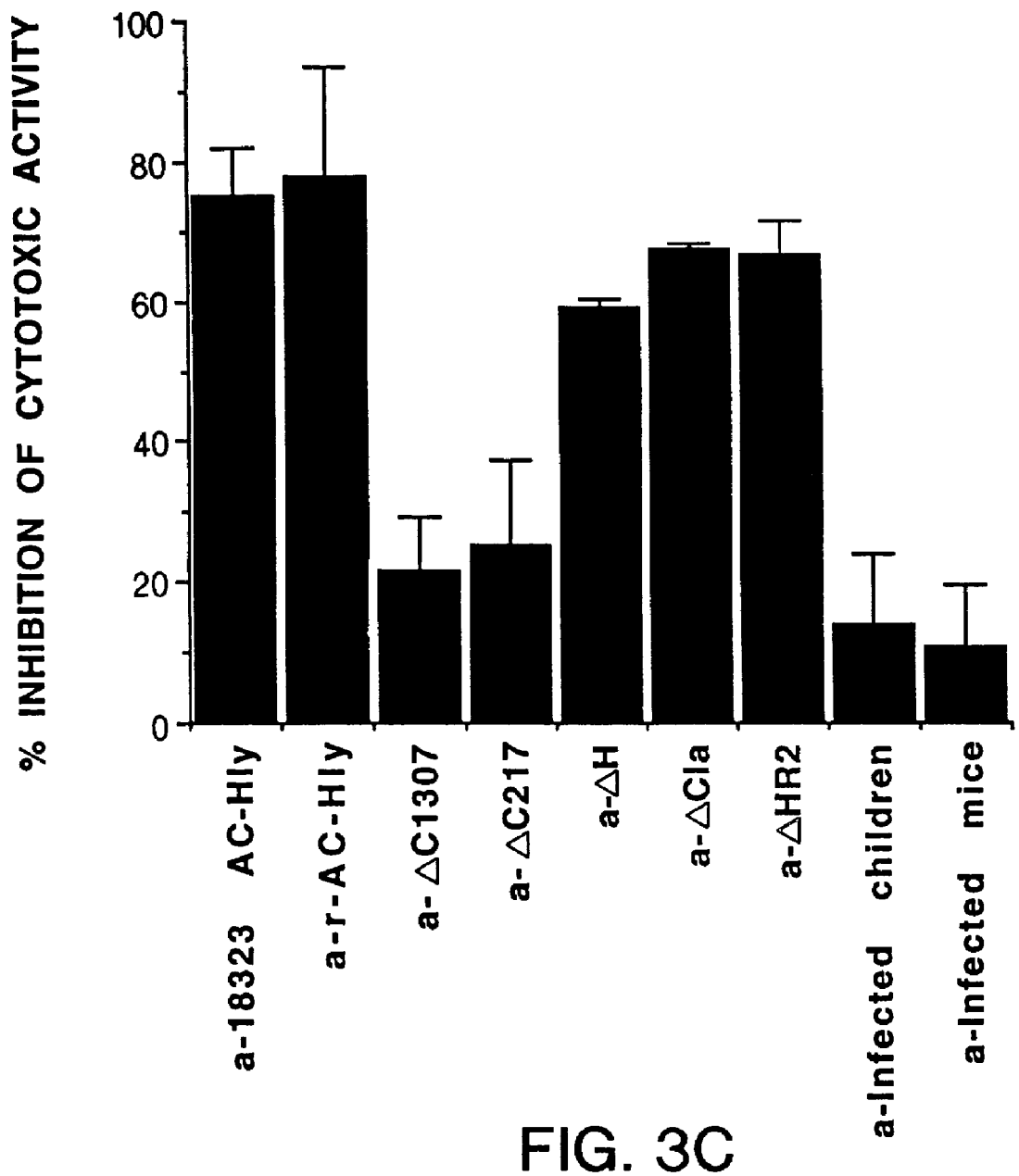
Figure 4B:
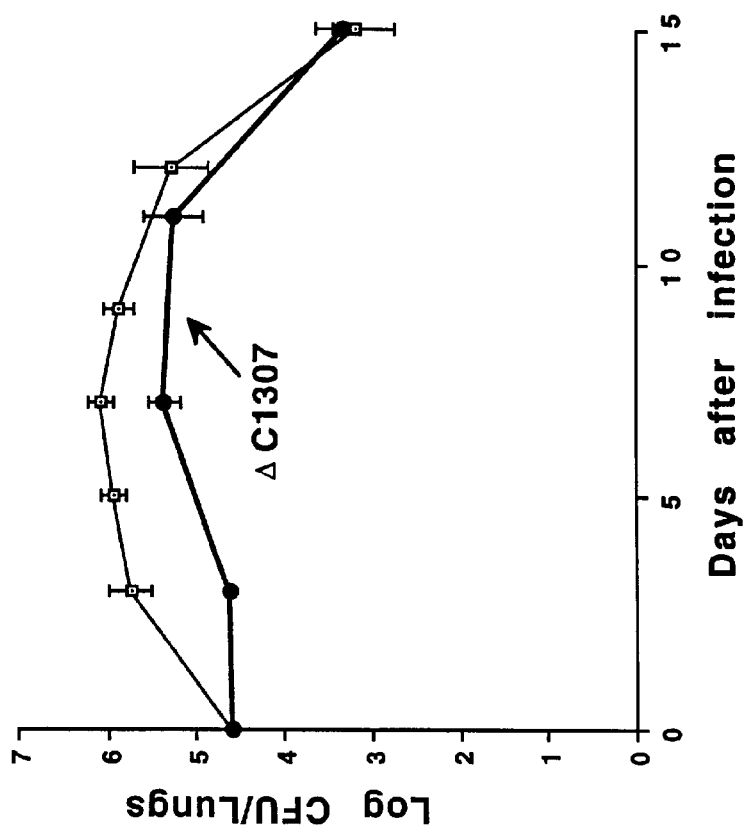
Figure 4A:
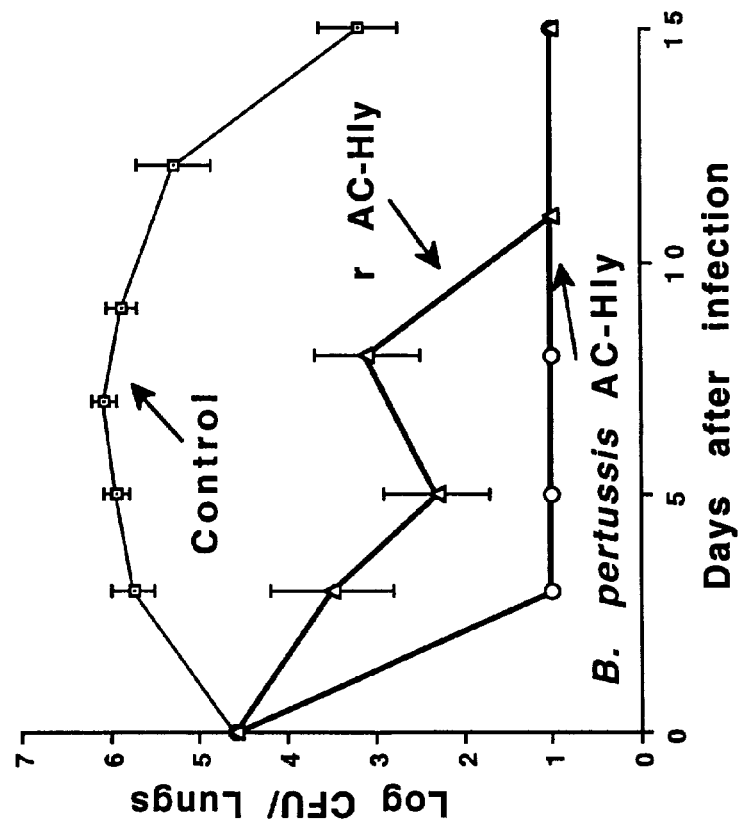
Figure 4D:
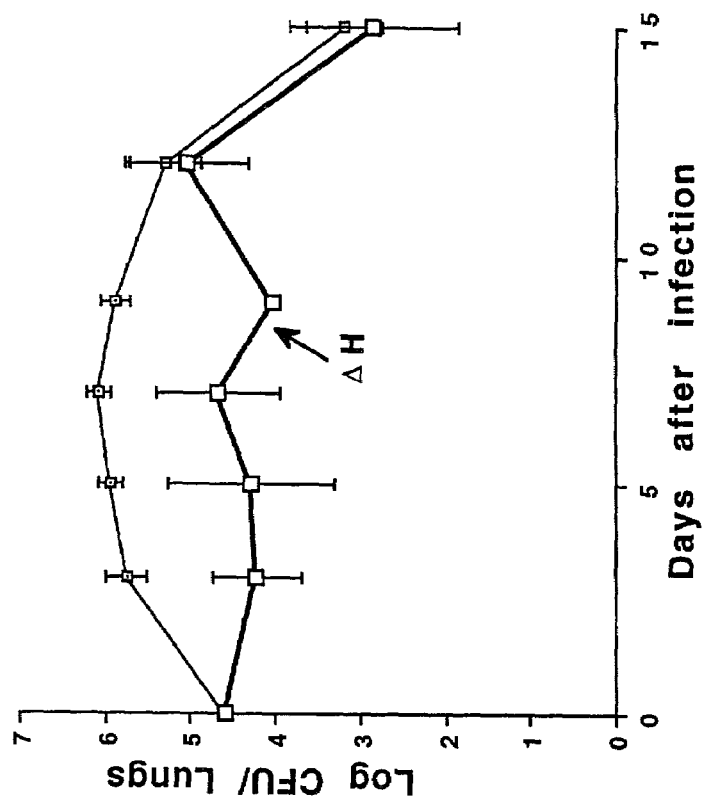
Figure 4C:
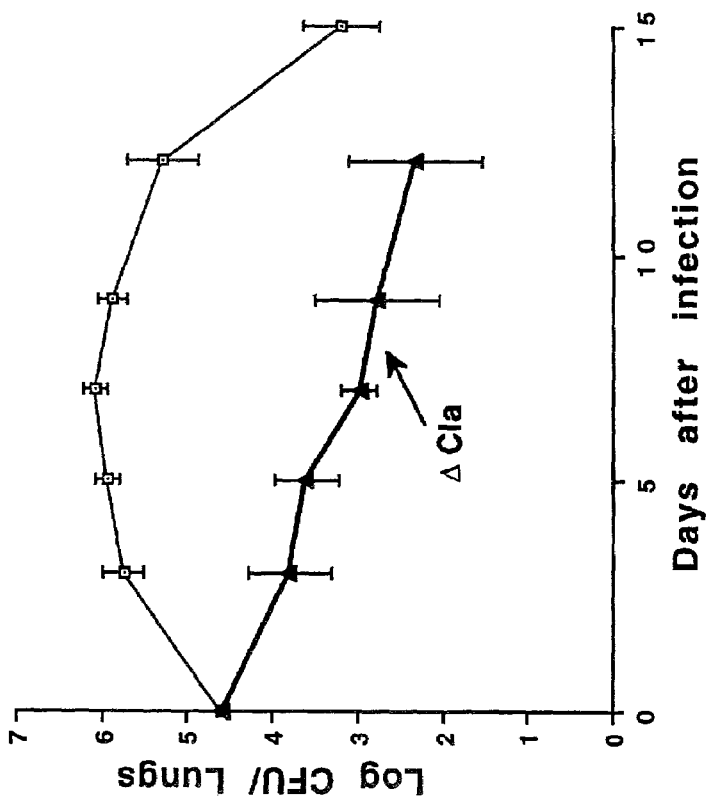
Figure 4F:
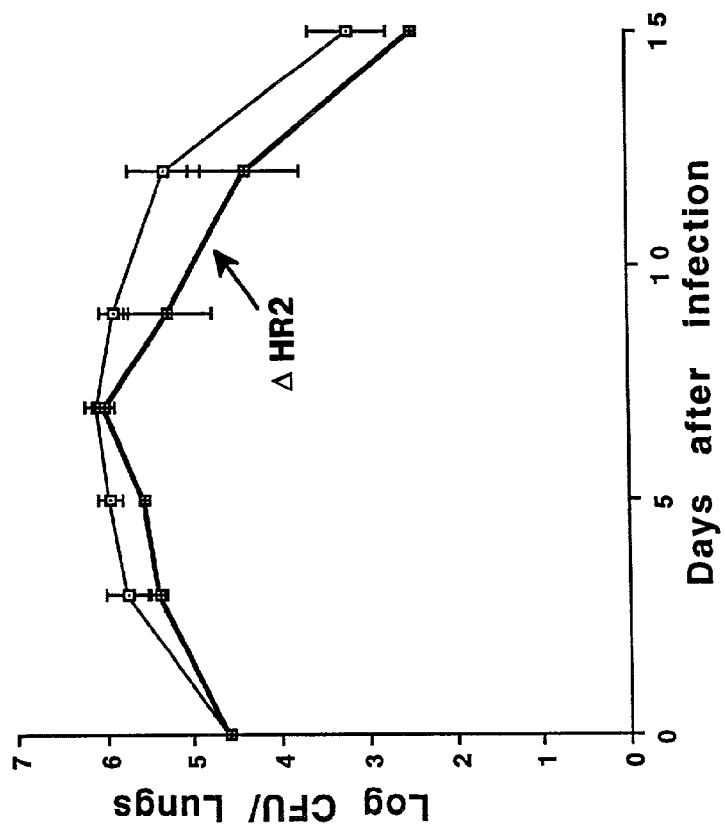
Figure 4E:
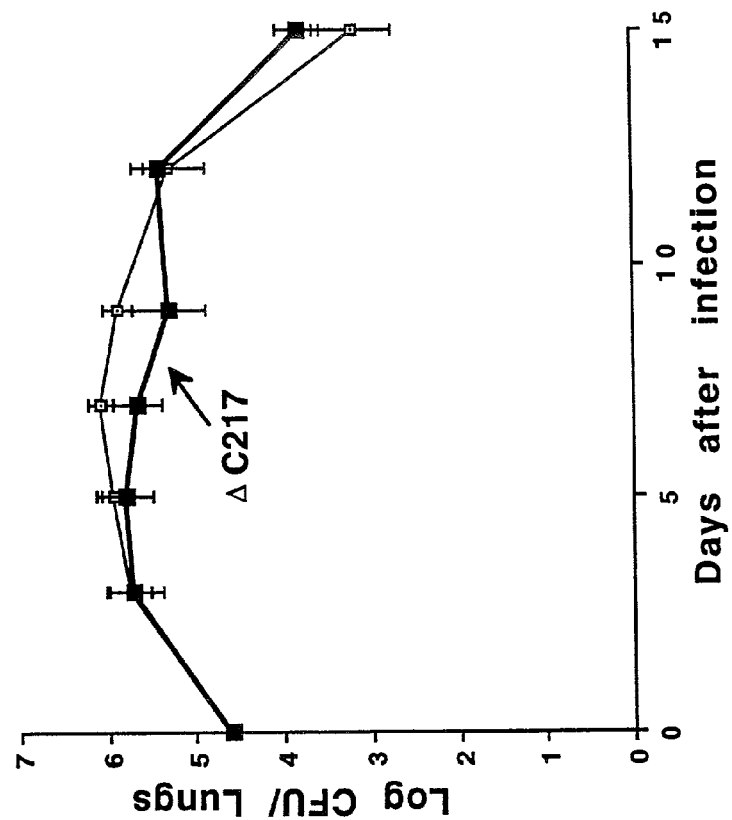

Inhibition of the Adenylate Cyclase, Haemolytic and Cytotoxic Activities by Sera Directed Against Truncated Derivatives of AC-Hly It was examined if sera from mice infected with *B. pertussis* or sera from human patients infected with *B. pertussis* or alternatively polyclonal sera directed against the various truncated forms of r-AC-Hly, obtained by immunization with the purified truncated proteins, could specifically inhibit one of the activities of the toxin. Since a control was necessary prior to these experiments, the ELISA titres of the various sera were determined using the complete r-AC-Hly as coating antigen for these tests. These titres were similar, with the exception of the titre obtained with the anti-ΔC1307 serum which did not recognize AC-Hly in ELISA although it recognized it in a Western Blot test like the other sera. As shown in FIG. 3A, the adenylate cyclase activity was inhibited by all of the sera obtained after immunization of mice with purified r-AC-Hly and with truncated derived proteins. However, none of the sera from the infected mice or from the infected human patients inhibited the AC activity of AC-Hly under identical conditions. This is in agreement with the result obtained by the Western Blot analysis (see above) showing that these sera contain antibodies predominantly directed against the C-terminal part of AC-Hly (last 900 residues) and not against the AC domain. Indeed, the haemolytic activity of the protein AC-Hly was inhibited by the sera from infected children and was less strongly inhibited by the sera from infected mice. However, a strong inhibition of the haemolytic activity was observed with the antisera obtained by immunization with the proteins AC-Hly, r-AC-Hly, ΔH, ΔCla and ΔHR2 from *B. pertussis* (FIG. 3B). This inhibition was probably due to the presence of specific antibodies against the C-terminal part of AC-Hly. Indeed, the anti-ΔC1307 serum directed against the AC domain of AC-Hly which lacked such antibodies did not inhibit the haemolytic activity of AC-Hly. In a completely advantageous manner, the serum directed against the protein ΔC217 lacking only the last 217 residues did not inhibit the haemolytic activity of AC-Hly at a measurable level either. This indicates that the last 217 residues are either the target of the neutralizing antibodies or are involved in the formation of a structure which favours the synthesis of neutralizing antibodies directed against other parts of AC-Hly. Together, these results indicate, in addition, that the antibodies synthesized after infection are mainly directed against the C-terminal haemolysin part of AC-Hly and are capable of neutralizing the haemolytic activity of this protein but not the enzymatic activity of its N-terminal adenylate cyclase domain. As shown in FIG. 3C, a significant inhibition of the cytotoxic activity of AC-Hly was observed with sera obtained against intact AC-Hly and against the truncated proteins ΔH, ΔCla and ΔHR2 which all contain both the AC domain and the last 217 residues. The antisera also neutralized the AC and haemolytic activities. On the contrary, the 2 sera which inhibited either the haemolytic activity alone (for example the sera from infected mice or patients) or the AC activity alone (the anti-ΔC1306 and anti-ΔC217 sera) did not inhibit the cytotoxic activity of AC-Hly. Thus, it appeared that the presence of antibodies against the AC domain and against the last 217 residues of AC-Hly may be required in order to neutralize its cytotoxic activity.

Protective Activity of the Various Recombinant AC-Hly Constructs

In order to locate the epitopes of AC-Hly required to obtain a protective activity, the protective activity of various purified truncated proteins using the murine respiratory model was tested. Groups of mice were immunized twice with aluminium hydroxide alone (control), or with purified truncated proteins adsorbed on aluminium hydroxide and then these mice were brought into contact, via the intranasal route, with sublethal doses of virulent *B. pertussis* 18323 strains. This model reflects the capacity of the bacteria to adhere, colonize, survive and multiply in the respiratory system of mice. As shown in FIG. 4, the bacteria multiply rapidly in the lungs of the control mice for 6 days after infection, and then begin to be eliminated from the lungs. No multiplication of the bacteria was observed in the lungs of mice immunized with the proteins AC-Hly or r-AC-Hly from *B. pertussis* and after 3 days the number of bacteria began to increase (FIG. 4). In agreement with previous observations (Betsou F., Sebo and N. Guiso, 1993, CyaC-mediated activation is important not only for toxic but also for protective activities of *Bordetella pertussis* adenylate cyclase-haemolysin, Infect. Immun. 61:3583–3589), the protective efficacy of *B. pertussis* AC-Hly was higher than that of r-AC-Hly. A protection similar to that induced by r-AC-Hly was also obtained with the protein ΔCla, suggesting that the part deleted in the protein ΔCla between residues 827 and 887 was not essential for the induction of protective immunity. The protein ΔH, missing from residues 385 to 828, exhibited a weaker protective activity than ΔCla. No protection was induced by the protein ΔC1307 lacking the entire haemolysin part of AC-Hly. In a more advantageous manner, the protein ΔC217 lacking the last 217 residues and the protein ΔHR2 containing the last 217 residues of AC-Hly did not make it possible to induce protection. The protective activity is therefore correlated with the pattern of recognition of the individual constructs by the sera from infected patients or from infected mice.

DISCUSSION

The antibodies directed against AC-Hly are usually present in the sera from infected children (Arciniaga J. L., E. L. Hewlett, F. D. Johnson, A. Deforest, S. G. F. Wassilak, I. M. Onorato, C. R. Manclark and D. L. Burns, 1991, J. Infect. Dis. 163:135–142; and Guiso N., E. Grimprel, I. Anjak and P. Bégué, 1993, Eur. J. Clin. Microbiol. and Infect. Dis. In press) and it has in the past been demonstrated that immunization with AC-Hly protects mice against bacterial colonization by *Bordetella* (Khelef, N., H. Sakamoto and N. Guiso, 1992, Microb. Pathog. 12:227–235). The production of a set of truncated forms of recombinant AC-Hly has made it possible to carry out a study of the importance of various domains of the protein in the induction of protective immunity by vaccination with AC-Hly. The results presented above show that the anti-AC-Hly antibodies, synthesized after infection by *B. pertussis*, are predominantly directed against the modified domain and the repeat domain of AC-Hly (about 800 residues). Indeed, only the truncated forms of AC-Hly possessing these in tact regions were recognized by sera from infected mice and patients in a Western-Blot test and these proteins were the only ones to exhibit the capacity of inducing protection in mice. This indicates that at least in the case of mice, a relatively limited set of identical or overlapping epitopes may be advantageous both for inducing the synthesis of anti-AC-Hly antibodies by the infected subjects and for inducing the synthesis of protective antibodies obtained after vaccination with AC-Hly. The experiments reported previously have shown that the elimination of the last 217 residues of AC-Hly which are in the distal position relative to the sites of modification of the protein by the product of expression of the CyaC gene, at the level of the lysine residue 983, abolished the recognition of this protein (ΔC217) by sera from infected mice and patients and also abolished its protective activity. However, this was not due to a defect in modification of the protein ΔC217 since this protein was acylated at the level of the fatty acid chains when it was produced in the presence of the protein CyaC. Furthermore, the 217 residues per se were not recognized by the sera and did not show any protective activity when they were presented in the protein ΔHR2 which, for its part, lacked the modification site (lysine 983) and a large proportion of the repeat region.

This led to the conclusion that both the last 217 residues and the modification region were important for the protective activity of AC-Hly. Thus, interaction between the modified region and the last 217 residues of AC-Hly would be required for the formation or the activity of the protective epitopes of AC-Hly. Surprisingly, neither the protein ΔC217 missing from the last 217 residues of AC-Hly, nor the protein ΔHR2 lacking from the modified region and from a large portion of the repeats but containing the last 217 residues were recognized by the polyclonal sera from infected patients and/or from mice (fresh serum). The antisera could have a narrow specificity against a single epitope, or against a small group of epitopes located at the breakpoint of the repeat regions present in the proteins ΔC217 and ΔHR2 (proline 1489). However, this possibility does not appear highly probable with mixed polyclonal antisera. In addition, the sera from infected human patients and mice recognized most of the full length polypeptides of the various proteins but did not recognize the cleaved C-terminal proteolytic fragments present in these preparations, which fragments were recognized by an anti-AC monoclonal antibody. Taken together, these results suggest that the formation of protective epitopes on AC-Hly and the recognition of AC-Hly by the sera from infected subjects require the presence of a specific structure formed only when the modified and repeat regions of AC-Hly are present. It is conceivable that the formation of this structure could require the modification, by acylation, of the fatty acid chains after the translation of AC-Hly at the level of the lysine residue 983 and could be abolished by the elimination of the C-teminal part of AC-Hly. In this regard, it is important that both the haemolytic and cytotoxic activities of AC-Hly are lost when the last 75 residues of AC-Hly, which contain the unmodified secretory signal, are eliminated, and are not directly involved in the activity of formation of pores (4 and 29). These observations support, in addition, the hypothesis that the extreme part of the C-terminal region of AC-Hly plays an essential role in the overall structure of AC-Hly.

It has already been suggested that major protective epitopes of AC-Hly could be located in the AC portion (Guiso, N., M. Rocancourt, M. Szatanik and J. M. Alonso, 1989, Molec. Pathog. 7:373–380 and Guiso, N.M. Szatanik and M. Rocancourt, 1991, Microb. Pathog. 11:423–431). The results presented here show that contamination by AC-Hly fragments extending over the modified and repeat regions of AC-Hly might enter into the production of a protective activity associated with the fragments of the AC domain present in the preparations described in the prior state of the art. Nevertheless, the capacity of these contaminants in minor quantities to produce a protective activity may be doubtful. Another interpretation might be that, under certain conditions, the region between amino acids 385 and 450 or 500 could also play a role in the protective activity of AC-Hly. The structure of this region could be modified in AC-Hly in the absence of the last 217 amino acid residues or in the absence of acylation. The structure of the N-terminal part of 40–50 kDa and the presentation to the immune system could induce protection when this structure is cleaved in relation to the rest of the AC-Hly molecule in *B. pertussis* culture supernatants. One explanation for this hypothesis could be that a monoclonal antibody directed against the part of the molecule located between amino acids 385 and 400 is a protective antibody.

It was also examined whether a correlation exists between the protective activity of a truncated protein obtained from r-AC-Hly in vivo and its activity in inducing the synthesis of antibodies which could neutralize the toxic activity in vitro. Such a correlation was not established. While all the proteins having a protective activity induced the synthesis of neutralizing antibodies, the protein ΔHR2, which was not at all protective, induced a strongly neutralizing antibody response. This suggests that the presence of neutralizing antibodies in relation to the toxic activity of AC-Hly is not a reliable measure of the induction of protection against infection by *B. pertussis*.

It is moreover important to note that the protein ΔCla, lacking a portion of the hydrophobic domain, exhibited a protective activity. This recombinant protein is a good candidate for inclusion in acellular vaccines against pertussis since it does not exert any residual cytotoxic activity.

Preparation of a Vrg Urea Extract

The vrg urea extracts are prepared from the same 3 phase IV bacterial species, that is to say from bacteria no longer expressing any vag gene but expressing the vrg genes. The products of these genes are not yet well characterized, with the exception of the flagella of *B. bronchiseptica*. The vrg urea extracts are prepared like the vag urea extracts.

| Description of the culture media<br>Dehydrated Bordet Gengou medium | | |
|---|---|---|
| Composition: | 1 liter | 5 liters |
| Bordet Gengou medium | 30 g | 150 g |
| Glycerol | 10 ml | 50 ml |
| Pyrolysed water | 1 liter | 5 liters |
| Adjust the pH to 7.4 | | |
| Heat | | |
| Autoclave for 15 minutes at 120° | | |
| Store at 4° C. | | |

At the time of use:

Bordet Gengou is enriched with 15 to 20% sheep or horse blood. Melt the tubes and keep melted at 54° C. Add 2.5 ml of sheep blood to each tube, in a sterile manner. Pour the contents of the tube into a sterile Petri dish.

Remark

For the identification of *Bordetella pertussis* from a nasopharyngeal sample, use fresh dishes (maximum 7 days at 4° C.)

CSM agar medium

To prepare 2 liters of a 10-fold concentrated solution:

| | | |
|---|---|---|
| Sodium hydrogen glutamate | (Ref. Prolabo No.27872.298) | 107 g |
| L-Proline | (Ref. Merck No.7434) | 2.4 g |
| NaCl | (Ref. Prolabo No.27810.295) | 25 g |
| $H_2PO_4$ | (Ref. Prolabo No.26926.298) | 5 g |
| KCl | (Ref. Prolabo No.26759.291) | 2 g |
| $MgCl_2$ | (Ref. Prolabo No.25108.295) | 1 g |
| Tris-base | (Ref. Merck No.8382.2500) | 15.2 g |
| Casamino acids | (Ref. Difco No.0288-01-2) | 5 g |
| 1% $CaCl_2$ solution in pyrolysed water (Ref. Prolabo No.22317.297 | | 20 ml |
| Pyrolysed water qs | | 1 liter |

Dissolve the various constituents in a portion of the final volume of water. Adjust the pH to 7.4 using hydrochloric acid. Fill to the final volume and store at −20° C.

At the time of use, mix:

100 ml of the 10-fold concentrated solution 900 ml of pyrolysed water 1 g of (2,6-O-dimethyl)cyclodextrin, reference Aldrich No.51166-71-3

15 g of Bacto agar, reference Difco No.0140-01 Distribute, in fractions of 20 ml, into glass tubes. Sterilize and add the sterile complement.

Solution of complement:

Mix:

1 ml of solution of complement concentrated 10-fold 100 mg of glutathion, reference Merck No.4090-

9 ml of pyrolysed water

Filter this solution on a 0.22 μm Millex filter.

Add 200 μl of this solution to 1 tube of 20 ml of medium.

| Stainer culture medium | | |
|---|---|---|
| A. Basal medium | | |
| To prepare 2 liters of a 10-fold concentrated solution: | | |
| Sodium hydrogen glutamate | (Ref. Prolabo No.27872.298) | 214.0 g |
| L-Proline | (Ref. Merck No.7434) | 4.8 g |
| NaCl | (Ref. Prolabo No.27810.295) | 50.0 g |
| H$_2$PO$_4$ | (Ref. Prolabo No.26926.298) | 10.0 g |
| KCl | (Ref. Prolabo No.26759.291) | 4.0 g |
| MgCl$_2$ | (Ref. Prolabo No.25108.295) | 2.0 g |
| Tris-base | (Ref. Merck No.8382.2500) | 30.5 g |
| 1% CaCl$_2$ solution in pyrolysed water (Ref. Prolabo No.22317.297 | | 40 ml |
| Pyrolysed water qs | | 2 liters |

Dissolve the various constituents in a portion of the final volume of water. Adjust the pH to 7.6 using hydrochloric acid. Fill to the final volume and distribute this concentrated solution which may be stored at −20° C. for several weeks.

At the time of use, dilute the medium, sterilize it at 120° C. for 15 minutes and then add the complement sterilized by filtration.

B. Solution of complement
To prepare 200 ml of a 10-fold concentrated solution:
L-cystine (Ref. Prolabo No.23260.184) . . . 8 g
Concentrated HCl 20 ml Dissolve, Over this preparation, pour the following mixture dissolved beforehand:

FeSO$_4$.7H$_2$O (Ref. Prolabo No.24244.232) . . . 2 g

L(+)ascorbic acid (Ref. Prolabo No.20155.237) . . . 4 g

Nicotinic acid (Ref. Merck No.6817) . . . 0.8 g

Pyrolysed water . . . 120 ml

Bring to 200 ml with pyrolysed water, distribute the solution in fractions of 1, 2, 3 or 4 ml and freeze at −200C.

At the time of use, dilute the solution 10-fold in pyrolysed water and add: glutathion (Ref. Merck No.4090) . . . 100 mg/10 ml of diluted complement, sterilize this solution by filtration (0.22 μm Millex filter for single use) and add 1 ml of sterile solution to 100 ml of sterile basal medium.

2.1.2. Preparation of the vrg urea extract

Centrifuge the bacterial suspension for 30 minutes at 5000 g, at 4° C.

Resuspend the bacterial pellet in 5M urea prepared in PBS buffer (described further on) in an amount of a volume equal to 5 times the wet weight of the bacterial pellet.

Leave stirring for 1 hour at 4° C. and then centrifuge for 40 minutes for 40,000 g, at 4° C., Store the supernatant at −80° C. until use.

2.1.3. Inactivation of the vrg urea extract

After removal of the urea by passage over a G25 column, the vrg urea extract is diluted in PBS so as to obtain a protein concentration of 300 μg/ml.

Add dropwise a volume of glutaraldehyde at 2.5% so as to obtain a final concentration of 0.05%.

Leave for 2 hours at room temperature while mixing regularly.

Stop the reaction by addition of lysine (final concentration 0.02M).

After 2 hours at room temperature, the urea extract is adsorbed on aluminium hydroxide prepared in PBS (1 mg/ml), overnight at 4° C., with gentle stirring. The vaccine is then ready for immunization of the animal in an amount of 10 to 20 μg/injection (described further on).

What is claimed is:

1. A monoclonal antibody that binds to an epitope within amino acids 385 to 400 of the adenyl cyclase haemolysin from *B. pertussis* (SEQ ID NO:2), wherein the antibody is produced by hybridoma B5-4 deposited at the CNCM under the No. I-1734.

2. A hybridoma that produces a monoclonal antibody that binds to an epitope within amino acids 385 to 400 of the adenyl cyclase haemolysin from *B. pertussis* (SEQ ID NO:2), wherein the hybridoma is hybridoma B5-4 deposited at the CNCM under the No. I-1734.

3. A pharmaceutical composition comprising:

a monoclonal antibody that binds to an epitope within amino acids 385 to 400 of the adenyl cyclase haemolysin from *B. pertussis* (SEQ ID NO:2), wherein the antibody is produced by hybridoma B5-4 deposited at the CNCM under the No. I-1734; and a pharmaceutically acceptable vehicle.

* * * * *

UNITED STATES PATENT AND TRADEMARK OFFICE
CERTIFICATE OF CORRECTION

PATENT NO. : 6,994,854 B1  
DATED : February 7, 2006  
INVENTOR(S) : Fotini Betsou, Peter Sebo and Nicole Gutso It is certified that error appears in the above-identified patent and that said Letters Patent is hereby corrected as shown below:

<u>Title page, Item [54] and Column 1, line 1,</u>
Title, "ADENYL" should read -- ADENYLATE --;

<u>Title page,</u>
Item [75], Inventors, "Nicole Gutso," should read -- Nicole Guiso, --.

Signed and Sealed this

Eighteenth Day of April, 2006

JON W. DUDAS
*Director of the United States Patent and Trademark Office*